US008597877B2

(12) United States Patent
Tarr

(10) Patent No.: US 8,597,877 B2
(45) Date of Patent: Dec. 3, 2013

(54) **POLYMORPHIC LOCI THAT DIFFERENTIATE *ESCHERICHIA COLI* O157:H7 FROM OTHER STRAINS**

(75) Inventor: Phillip I. Tarr, Seattle, WA (US)

(73) Assignee: Seattle Children's Hospital, Seattle, WA (US)

( * ) Notice: Subject to any disclaimer, the term of this patent is extended or adjusted under 35 U.S.C. 154(b) by 906 days.

(21) Appl. No.: 11/787,195

(22) Filed: Apr. 12, 2007

(65) Prior Publication Data

US 2008/0102458 A1    May 1, 2008

Related U.S. Application Data

(63) Continuation of application No. 09/875,573, filed on Jun. 5, 2001, now abandoned, which is a continuation of application No. PCT/US99/29149, filed on Dec. 8, 1999.

(60) Provisional application No. 60/111,493, filed on Dec. 8, 1998.

(51) Int. Cl.
*C12Q 1/68* (2006.01)
*C12P 19/34* (2006.01)
*C07H 21/02* (2006.01)
*C07H 21/04* (2006.01)

(52) U.S. Cl.
USPC ......... 435/6.1; 435/91.1; 435/91.2; 536/23.1; 536/24.3

(58) Field of Classification Search
None
See application file for complete search history.

(56) References Cited

U.S. PATENT DOCUMENTS

| | | | |
|---|---|---|---|
| 5,082,767 A | 1/1992 | Hatfield et al. | 435/6 |
| 5,126,239 A | 6/1992 | Livak et al. | 435/6 |
| 5,288,707 A | 2/1994 | Metternich | 514/19 |
| 5,474,796 A | 12/1995 | Brennan | 427/2.13 |
| 5,552,534 A | 9/1996 | Hirschmann et al. | 536/17.4 |
| 5,580,703 A | 12/1996 | Kotin et al. | 435/320.1 |
| 5,654,417 A | 8/1997 | Tarr et al. | 536/24.32 |
| 5,738,995 A | 4/1998 | Wu et al. | 435/6 |
| 5,747,257 A | 5/1998 | Jensen | 435/6 |
| 5,758,293 A | 5/1998 | Frasier | 455/556 |
| 5,792,833 A | 8/1998 | Androphy et al. | 530/350 |
| 5,811,515 A | 9/1998 | Grubbs et al. | 530/330 |
| 5,817,626 A | 10/1998 | Findeis et al. | 514/12 |
| 5,817,879 A | 10/1998 | Hirschmann et al. | 568/333 |
| 5,821,231 A | 10/1998 | Arrhenius et al. | 514/18 |
| 5,855,885 A | 1/1999 | Smith et al. | 424/130.1 |
| 5,874,529 A | 2/1999 | Gilon et al. | 530/317 |

FOREIGN PATENT DOCUMENTS

| | | |
|---|---|---|
| EP | 0 332 435 | 9/1989 |
| EP | 587279 | 3/1994 |
| JP | 05276949 | 10/1993 |
| WO | WO 89/06279 | 7/1989 |
| WO | WO 94/10325 | 5/1994 |
| WO | WO 94/28017 | 12/1994 |

OTHER PUBLICATIONS

Nelson; PNAS, vol. 91, pp. 10227-10231; 1994.*
Bisercic; Journal of Bacteriology, vol. 173, pp. 3894-3900; 1991.*
Pupo et al; Infection and Immunity, vol. 65, pp. 2685-2692, Jul. 1997.*
Bilge et al., "Role of the *Escherichia coli* O157:H7 O side chain in adherence and analysis of an *rfb* locus," *Infect. Immun.* 64:4795-4801, 1996.
Bisercic et al., "Nucleotide sequences of the *gnd* genes from nine natural isolates of *Escherichia coli*: evidence of the intragenic recombination as a contributing factor in the evolution of the polymorphic gnd locus," *J. Bacteriol.* 173:3894-3900, 1991.
Bokete et al., "Genetic and phenotypic analysis of *Escherichia coli* with enteropathogenic characteristics isolated from Seattle children," *J. Infect. Dis.* 175:1382-1389, 1997.
Comstock et al., "Cloning and sequence of a region encoding a surface polysaccharide of *Vibrio cholerae* O139 and characterization of the insertion site in the chromosome of *Vibrio cholerae* O1," *Mol. Microbiol.* 19:815-826, 1996.
Desmarchelier et al., "A PCR specific for *Escherichia coli* O157 based on the *rfb* locus encoding O157 lipopolysaccharide," *J. Clin. Microbiol.* 36:1801-1804, 1998.
Dumontier et al., "Structural and functional characterization of IS*1358* from *Vibrio cholerae*," *J. Bacteriol.* 180:6101-6106, 1998.
Dykhuizen et al., "Recombination in *Escherichia coli* and the definition of biological species," *J. Bacteriol.* 173:7257-7268, 1991.
EMBL Database Accession No. M64328, Jul. 10, 1991.
EMBL Database Accession No. M64324, Jul. 21, 1991.
EMBL Database Accession No. U14423, Sep. 21, 1994.
EMBL Database Accession No. U14433, Sep. 21, 1994.
EMBL Database Accession No. U14443, Feb. 18, 1995.
Feng et al., "Genotypic and phenotypic changes in the emergence of *Escherichia coli* O157:H7," *Infect. Dis.* 177:1750-1753, 1998.
GenBank Accession No. A74817, 1994.
GenBank Accession No. AA285441, Apr. 1997.
Gish et al., "Identification of protein coding regions by database similarity search," *Nat. Genet.* 3:266-272, 1993.
Grif et al., "Comparative study of five different techniques for epidemiological typing of *Escherichia coli* O157," *Diag. Microbiol. Infect. Dis.* 32(3):165-176, Nov. 1998.
Grossman et al., "Lipopolysaccharide size and distribution determine serum resistance in *Salmonella montevideo*," *J. Bacteriol.* 169:856-863, 1987.
Gustafson et al., "Mutagenesis of the paracrystalline surface of protein array of *Aeromonas salmonicida* by endogenous insertion elements," *J. Mol. Biol.* 237:452-463, 1994.

(Continued)

*Primary Examiner* — Jehanne Sitton
(74) *Attorney, Agent, or Firm* — Seed IP Law Group PLLC

(57) ABSTRACT

The present invention relates generally to the field of microbiology and food sciences. More particularly, the inventor has discovered several polynucleotide sequences encoding the gnd gene and corresponding 6-phosphogluconate dehydrogenase (6-PGD) proteins from different strains of *Escherichia Coli* and polymorphic sequences therein. Novel biotechnological tools, diagnostics, and food screening techniques are provided.

9 Claims, 3 Drawing Sheets

(56) References Cited

OTHER PUBLICATIONS

Guttman et al., "Detecting selective sweeps in naturally occurring *Escherichia coli*," *Genetics* 138(4): 993-1003, 1994.

Hacker et al., "Pathogenicity islands of virulent bacteria: structure, function and impact on microbial evolution," *Mol. Microbiol.* 23:1089-1097, 1997.

Herzer et al., "Phylogenetic distribution of branched RNA-linked multicopy single-stranded DNA among natural isolates of *Escherichia coli*," *J. Bacteriol.* 172:6175-6181, 1990.

Hill et al., "*Rhs* elements of *Escherichia coli*: a family of genetic composites each encoding a large mosaic protein," *Mol. Microbiol.* 12(6):865-871, 1994.

Karaolis et al., "Sequence of variation in *Shigella sonnei* (Sonnei), a pathogenic clone of *Escherichia coli*, over four continents and 41 years," *J. Clin. Microbiol.* 32(3):796-802, 1994.

Kenne et al., "Structural studies of the O-antigens from *Salmonella greenside* and *Salmonella adelaide*," *Carbohydr. Res.* 111:289-296, 1983.

Kessler et al., "Molecular analysis of the 3,6-Dideoxyhexose pathway genes of *Yersinia pseudotuberculosis* serogroup IIA," *J. Bacteriol.* 175:1412-1422, 1993.

Lawrence et al., "Molecular archaeology of the *Escherichia coli* genome," *Proc. Natl. Acad. Sci. USA* 95:9413-9417, 1998.

Lindberg et al., "Structural studies of the O-specific side-chain of the lipopolysaccharide from *Escherichia coli* O 55," *Carbohydr. Res* 97:105-112, 1981.

Liu et al., "Presence of different O antigen forms in three isolates of one clone of *Escherichia coli*," *Genetics* 138:7-10, 1994.

McGraw et al., "Molecular evolution and mosaic structure of α, β and γ intimins of pathogenic *Escherichia coli*," *Mol. Biol. Evol.* 16:12-22, 1999.

Nelson et al., "Intergeneric transfer and recombination of the 6-phosphogluconate dehydrogenase gene (*gnd*) in enteric bacteria," *Proc. Natl. Acad. Sci. USA* 91:10227-10231, 1994.

Owen et al., "Antigenic architecture of membrane vesicles from *Escherichia coli*," *Biochemistry* 18:1422-1426, 1979.

Paton et al., "Molecular characterization of the locus encoding biosynthesis of the lipopolysaccharide O antigen of *Escherichia coli* serotype O113," *Infect. Immun.* 67:5930-5937, 1999.

Perry et al., "Structure of the O-chain polysaccharide of the phenol-phase soluble lipopolysaccharide of *Escherichia coli* O157:H7," *Biochem. Cell. Biol.* 64:21-28, 1986.

Pupo et al., "Evolutionary relationships among pathogenic and nonpathogenic *Escherichia coli* strains inferred from multilocus enzyme electrophoresis and *mdh* sequence studies," *Infect. Immun.* 65:2685-2692, 1997.

Ramsay, "DNA chips: state-of-the-art," *Nat. Biotechnol.* 16:40-44, 1998.

Reeves, "Role of O-antigen variation in the immune response," *Trends Microbiol.* 3:381-386, 1995.

Reeves et al., "Bacterial polysaccharide synthesis and gene nomenclature," *Trends Microbiol.* 4:495-503, 1996.

Reid et al., "Sequence diversity of flagellin (*filC*) alleles in pathogenic *Escherichia coli*," *J. Bacteriol.* 181:153-160, 1999.

Selander et al., "Methods of multilocus enzyme electrophoresis for bacterial population genetics and systematics," *Appl. Environ. Microbiol.* 51:873-884, 1986.

Sharp, "Determinants of DNA sequence divergence between *Escherichia coli* and *Salmonella typhimurium*: codon usage, map position, and concerted evolution," *J. Mol. Evol.* 33:23-33, 1991.

Shimizu et al., "Analysis of the genes responsible for the O-antigen synthesis in enterohaemorrhagic *Escherichia coli* O157," *Microb. Pathog.* 26:235-247, 1999.

Smith, "Analyzing the mosaic structure of genes," *J. Mol. Evol.* 34:126-129, 1992.

Stroeher et al., "Genetic rearrangements in *rfb* regions of *Vibrio cholerae* O1 and O139," *Proc. Natl. Acad. Sci. USA* 92:10374-10378, 1995.

Stroeher et al., "Novel *Vibrio cholerae* O139 genes involved in lipopolysaccharide biosynthesis," *J. Bacteriol.* 179:2740-2747, 1997.

Supplementary Partial European Search Report for Application No. EP 99965181, dated Aug. 9, 2002.

Tarr et al., "Genotypic variation in pathogenic *Escherichia coli* O157:H7 isolated from patients in Washington 1984-1987," *J. Infect Dis.* 159:344-347, 1989.

Tarr, "*Escherichia coli* O157:H7: clinical, diagnostic and epidemiological aspects of human infection," *Clin. Infect. Dis.* 20:1-8, 1995.

Tarr et al., "Acquisition of the *rfb-gnd* chromosomal region in the divergence of *Escherichia coli* O157:H7 from *E. coli* O55:H7 (abstract and poster)," Annual Meeting of the American Society for Microbiology, 1999.

Tarr et al., "Acquisition of the *rfb-gnd* cluster in evolution of *Escherichia coli* O55 and O157," *J. Bacteriol.* 182(21):6183-6191, Nov. 2000.

Wang et al., "Sequencing of *Escherichia coli* O111 O-antigen gene cluster and identification of O111-specific genes," *J. Clin. Microbiol.* 36:3182-3187, 1998.

Wang et al., "Organization of *Escherichia coli* O157 O antigen gene cluster and identification of its specific genes," *Infect. Immun.* 66:3545-3551, 1998.

Whitfield, "Biosynthesis of lipopolysaccharide O antigens," *Trends Microbiol.* 1:1-8, 1995.

Whittam et al., Genetic evidence of clonal descent of *Escherichia coli* O157:H7 associated with hemorrhagic colitis and hemolytic uremic syndrome, *J. Infect Dis.* 157:1124-1133, 1988.

Whittam et al., "Genetic relationships among pathogenic *Escherichia coli* of serogroup O157," *Infect Immun* 56:2467-2473, 1988.

Whittam et al., "Clonal relationships among *Escherichia coli* strains that cause hemorrhagic colitis and infantile diarrhea," *Infect. Immun.* 61:1619-1629, 1993.

Xiang et al., "Molecular analysis of the *rfb* gene cluster of a group D2 *Salmonella enterica* strain: evidence for its origin from an insertion sequence-medicated recombination event between group E and D1 strains," *J. Bacteriol.* 176:4357-4365, 1994.

Zhao et al., "*Rhs* elements of *Escherichia coli* K-12: complex composites of shared and unique components that have different evolutionary histories," *J. Bacteriol.* 175:2799-2808, 1993.

Alignment for Accession No. AAQ65501 (WO 94/10325), 1994.

Adrianopolous et al., "Identification of the fucose synthetase gene in the colanic acid gene cluster of *Escherichia coli* K-12," *J. Bacteriol.* 180:998-1001, 1998.

Bastin et al., "Sequence and analysis of the O antigen gene (*rfb*) cluster of *Escherichia coli* O111," *Gene* 164:17-23, 1995.

Bik et al., "Genesis of the novel epidemic *Vibrio cholerae* O139 strain: evidence for horizontal transfer of genes involved in polysaccharide synthesis," *EMBO J.* 14:209-216, 1995.

Ackers et al., "An Outbreak of *Escherichia coli* O157:H7 Infections Associated with Leaf Lettuce Consumption" The Journal of Infectious Diseases 177: 1588-1593, 1998.

Altschul et al., "Basic Local Alignment Search Tool" J. Mol. Biol. 215: 403-410, 1990.

Altschul et al., "Gapped BLAST and PSI-BLAST: a new generation of protein database search programs" Nucleic Acids Research 25(17): 3389-3402, 1997.

Anonymous, "Outbreak of *Escherichia coli* O157:H7 Infections Associated with Drinking Unpasteurized Commercial Apple Juice—British Columbia, California, Colorado, and Washington, Oct. 1996" Morbidity and Mortality Weekly Report 45(44): 975-976, 1996.

Barcak et al., "Comparative Nucleotide Sequence Analysis of Growth-Rate-Regulated *gnd* Alleles from Natural Isolates of *Escherichia coli* and from *Salmonella typhimurium* LT-2" Journal of Bacteriology 170(1): 372-379, 1988.

Basta et al., "Sensitive Receptor-Specified Enzyme-Linked Immunosorbent Assay for *Escherichia coli* Verocytotoxin" Journal of Clinical Microbiology 27(7): 1617-1622, 1989.

Bell et al., "A Multistate Outbreak of *Escherichia coli* O157:H7-Associated Bloody Diarrhea and Hemolytic Uremic Syndrome From Hamburgers" JAMA 272(17): 1349-1353, 1994.

(56) References Cited

OTHER PUBLICATIONS

Bell et al., "Predictors of Hemolytic Uremic Syndrome in Children During a Large Outbreak of *Escherichia coli* O157:H7 Infections" Pediatrics 100(1-E12): 1-6, 1997.

Beltran et al., "Toward a population genetic analysis of Salmonella: Genetic diversity and relationships among strains of serotypes *S. choleraesuis, S. derby, S. Dublin, S. enteritidis, S. heidelberg, S. infantis, S. Newport,* and *S. typhimurium*" Proc. Natl. Acad. Sci. USA 85: 7753-7757, 1988.

Bennett et al., "Evaluation of methods for the isolation and detection of *Escherichia coli* O157 in minced beef" Letters in Applied Microbiology 20: 375-379, 1995.

Bennett et al., "The isolation and detection of *Escherichia coli* O157 by use of immunomagnetic separation and immunoassay procedures" Letters in Applied Microbiology 22: 237-243, 1996.

Bielaszewska et al., "Isolation and Characterization of Sorbitol-Fermenting Shiga Toxin (Verocytotoxin)-Producing *Escherichia coli* O157:H-Strains in the Czech Republic" Journal of Clinical Microbiology 36(7): 2135-2137, 1998.

Blanco et al., "Detection of enterohaemorrhagic *Escherichia coli* O157:H7 in minced beef using immunomagnetic separation" Microbiologia 12(3): 385-394, 1996. (Abstract).

Bolton et al., "Isolation of *Escherichia coli* O157 from raw meat products" Letters in Applied Microbiolgy 23: 317-321, 1996.

Boyd et al., "*Salmonella* reference collection B (SARB): strains of 37 serovars of subspecies I" Journal of General Microbiology 139: 1125-1132, 1993.

Brandt et al., "*Escherichia coli* O157:H7-associated hemolytic-uremic syndrome after ingestion of contaminated hamburgers" J. Pediatr. 125: 519-526, 1994.

Cariello et al., "Resolution of a Missense Mutant in Human Genomic DNA by Denaturing Gradient Gel Electrophoresis and Direct Sequencing Using in Vitro DNA Amplification: HPRT $_{Munich}$" Am. J. Hum. Genet. 42: 726-734, 1988.

Carter et al., "A Severe Outbreak of *Escherichia coli* O157:H7-Associated Hemorrhagic Colitis in a Nursing Home" The New England Journal of Medicine 317: 1496-1500, 1987.

Conner et al., "Detection of sickle cell $\beta^S$-globin allele by hybridization with synthetic oligonucleotides" Proc. Natl. Acad. Sci. USA 80: 278-282, 1983.

Cotton et al., "Reactivity of cytosine and thymine in single-base-pair mismatches with hydroxylamine and osmium tetroxide and its application to the study of mutations" Proc. Natl. Acad. Sci. USA 85: 4397-4401, 1988.

Doyle et al., "Isolation of *Escherichia coli* O157:H7 from Retail Fresh Meats and Poultry" Applied and Environmental Microbiology 53(10): 2394-2396, 1987.

Feldsine et al., "Assurance *Escherichia coli* O157:H7: A Comparative Validation Study" Journal of AOAC International 80(1): 37-42, 1997.

Feldsine et al., "*Escherichia coli* O157:H7 Visual Immunoprecipitate Assay: A Comparative Validation Study" Journal of AOAC International 80(1): 43-48, 1997.

Feldsine et al., "Visual Immunoprecipitate Assay (VIP) for Detection of Enterohemorrhagic *Escherichia coli* (EHEC) O157:H7 in Selected Foods: Collaborative Study" Journal of AOAC International 80(3): 517-529, 1997.

Feldsine et al., "Assurance Enzyme Immunoassay for Detection of Enterohemorrhagic *Escherichia coli* O157:H7 in Selected Foods: Collaborative Study" Journal of AOAC International 80(3): 530-543, 1997.

Feng et al., "Identification of a Rough Strain of *Escherichia coli* O157:H7 That Produces No Detectable O157 Antigen" Journal of Clinical Microbiology 36(8): 2339-2341, 1998.

Ferguson et al., "Cell-Surface Anchoring of Proteins Via Glycosyl-Phosphatidylinositol Structures" Ann. Rev. Biochem. 57: 285-320, 1988.

Finkelstein et al., "Use of Denaturing Gradient Gel Electrophoresis for Detection of Mutation and Prospective Diagnosis in Late Onset Ornithine Transcarbamylase Deficiency" Genomics 7: 167-172, 1990.

GenBank Accession No. AB008676, 13 pages, 1999.
GenBank Accession No. AF061251, 6 pages, 1998.
GenBank Accession No. AF093749, 9 pages, 1999.
GenBank Accession No. L02370, 4 pages, 2002.
GenBank Accession No. U13629, 4 pages, 1997.

Grompe et al., "Scanning detection of mutations in human orinthine transcarbamoylase by chemical mismatch cleavage" Proc. Natl. Acad. Sci. USA 86: 5888-5892, 1989.

Grompe, "The rapid detection of unknown mutations in nucleic acids" Nature Genetics 5: 111-117, 1993.

Gunzer et al., "Molecular Detection of Sorbitol-Fermenting *Escherichia coli* O157 in Patients with Hemolytic-Uremic Syndrome" Journal of Clinical Microbiology 30(7): 1807-1810, 1992.

Jinneman et al., "Comparison of Template Preparation Methods from Foods for Amplification of *Escherichia coli* O157 Shiga-Like Toxins Type I and II DNA by Multiplex Polymerase Chain Reaction" Journal of Food Protection 58(7): 722-726, 1995.

Johnson et al., "Detection of *Escherichia coli* O157:H7 in Meat by an Enzyme-Linked Immunosorbent Assay, EHEC-Tek" Applied and Environmental Microbiology 61(1): 386-388, 1995.

Karch et al., "Long-Term Shedding and Clonal Turnover of Enterohemorrahagic *Escherichia coli* O157 in Diarrheal Diseases" Journal of Clinical Microbiology 33(6): 1602-1605, 1995.

Karch et al., "Isolation of Enterohemorrhagic *Escherichia coli* O157 Strains from Patients with Hemolytic-Uremic Syndrome by Using Immunomagnetic Separation, DNA-Based Methods, and Direct Culture" Journal of Clinical Microbiology 34(3): 516-519, 1996.

Karmali et al., "Sporadic Cases of Haemolytic-Uraemic Syndrome Associated With Faecal Cytotoxin and Cytotoxin-Producing *Escherichia coli* in Stools" Lancet 321(8325): 619-620, 1983.

Keene et al., "A Prolonged Outbreak of *Escherichia coli* O157:H7 Infections Caused by Commercially Distributed Raw Milk" The Journal of Infectious Diseases 176: 815-818, 1997.

Keene et al., "A Swimming-Associated Outbreak of Hemorrhagic Colitis Caused by *Escherichia coli* O157:H7 and *Shigella sonnei*" The New England Journal of Medicine 331(9): 579-584, 1994.

Kehl et al., "Evaluation of the Premier EHEC Assay for Detection of Shiga Toxin-Producing *Escherichia coli*" Journal of Clinical Microbiology 35(8): 2051-2054, 1997.

Kim et al., "Dipstick Immunoassay to Detect Enterohemorrhagic *Escherichia coli* O157:H7 in Retail Ground Beef" Applied and Environmental Microbiology 58(5): 1764-1767, 1992.

Kinzler et al., "Identification of a Gene Located at Chromosome 5q21 That is Mutated in Colorectal Cancers" Science 251: 1366-1370, 1991.

LeClerc et al., "High Mutation Frequencies Among *Escherichia coli* and *Salmonella* Pathogens" Science 274: 1208-1211, 1996.

March et al., "Sorbitol-MacConkey Medium for Detection of *Escherichia coli* O157:H7 Associated with Hemorrhagic Colitis" Journal of Clinical Microbiology 23(5): 869-872, 1986.

Martin et al., "The Epidemiology and Clinical Aspects of the Hemolytic Uremic Syndrome in Minnesota" The New England Journal of Medicine 323(17): 1161-1167, 1990.

Mead et al., "Risk Factors for Sporadic Infection With *Escherichia coli* O157:H7" Arch. Inter. Med. 157: 204-208, 1997.

Modrich, "Mechanisms and Biological Effects of Mismatch Repair" Annu. Rev. Genet. 25: 229-253, 1991.

Neill et al., "Hemorrhagic Colitis with *Escherichia coli* O157:H7 Preceding Adult Hemolytic Uremic Syndrome" Arch. Intern. Med. 145: 2215-2217, 1985.

Neill et al., "*Escherichia coli* O157:H7 as the Predominant Pathogen Associated With the Hemolytic Uremia Syndrome: A Prospective Study in the Pacific Northwest" Pediatrics 80: 37-40, 1987.

Newton et al., "Analysis of any point mutation in DNA. The amplification refractory mutation system (ARMS)" Nucleic Acids Research 17(7): 2503-2516, 1989.

(56) References Cited

OTHER PUBLICATIONS

Notermans et al., "DNA hybridization and latex agglutination for detection of heat-labile- and shiga-like toxin-producing *Escherichia coli* in meat" International Journal of Food Microbiology 13: 31-40, 1991.
Novack et al., "Detection of single base-pair mismatches in DNA by chemical modification followed by electrophoresis in 15% polyacrylamide gel" Proc. Natl. Acad. Sci. USA 83: 586-590, 1986.
Okrend et al., "An Improved Screening Method for the Detection and Isolation of *Escherichia coli* O157:H7 From Meat, Incorporating the 3M Petrifilm™ Test Kit—HEC—for Hemorrhagic *Escherichia coli* O157:H7" J. Food Protect 53: 936-940, 1990.
Orita et al., "Detection of polymorphisms of human DNA by gel electrophoresis as single-strand conformation polymorphisms" Proc. Natl. Acad. Sci. USA 86: 2766-2770, 1989.
Padhye et al., "Rapid Procedure for Detecting Enterohemorrhagic *Escherichia coli* O157:H7 in Food" Applied and Environmental Microbiology 57(9): 2693-2698, 1991.
Park et al., "Isolation of Shiga-like Toxin Producing *Escherichia coli* (O157 and non-O157) in a Community Hospital" Diagn. Microbiol. Infect. Dis. 26: 69-72, 1996.
Paton et al., "Detection and Characterization of Shiga Toxigenic *Escherichia coli* by Using Multiplex PCR Assays for $stx_1$, $stx_2$, *eaeA*, Enterohemorrhagic *E. coli hlyA*, $rfb_{O111}$, and $rfb_{O157}$" Journal of Clinical Microbiology 36(2): 598-602, 1998.
Pawelzik, "Pathogenic *Escherichia coli* O157:H7 and their detection" Acta Microbiol. Hung. 38(3-4): 315-320, 1991. (Abstract).
Pearson et al., "Improved tools for biological sequence comparison" Proc. Natl. Acad. Sci. USA 85: 2444-2448, 1988.
Ratnam et al., "Sporadic occurrence of hemorrhagic colitis associated with *Escherichia coli* O157:H7 in Newfoundland" Can. Med. Assoc. J. 134: 43-46, 1986.
Ratnam et al., "Characterization of *Escherichia coli* Serotype O157:H7" Journal of Clinical Microbiology 26(10): 2006-2012, 1988.
Read et al., "Prevalence of verocytotoxigenic *Escherichia coli* in ground beef, pork, and chicken in southwestern Ontario" Epidemiol. Infect. 105: 11-20, 1990.
Reeves, "Biosynthesis and assembly of lipopolysaccharide" New Compr. Biochem. 27: 281-314, 1994.
Riley et al., "Hemorrhagic Colitis Associated with a Rare *Escherichia coli* Serotype" The New England Journal of Medicine 308: 681-685, 1983.
Rodrigue et al., "A University Outbreak of *Escherichia coli* O157:H7 Infections Associated with Roast Beef and an Unusually Benign Clinical Course" J. Infect. Dis. 172: 1122-1125, 1995.
Ruano, "Direct haplotyping of chromosomal segments from multiple heterozygotes via allele-specific PCR amplification" Nucleic Acids Research 17: 8392, 1989.
Ryan et al., "*Escherichia coli* O157:H7 Diarrhea in a Nursing Home: Clinical, Epidemiological, and Pathological Findings" J. Infect. Dis. 154(4): 631-638, 1986.
Sali et al., "Comparative Protein Modelling by Satisfaction of Spatial Restraints" J. Mol. Biol. 234: 779-815, 1993.
Sekla et al., "Verotoxin-producing *Escherichia coli* in ground beef in Manitoba" Can. Med. Assoc. J. 143(6): 519-521, 1990.
Selander et al., "Evolutionary Genetic Relationships of Clones of *Salmonella* Serovars That Cause Human Typhoid and Other Enteric Fevers" Infection and Immunity 58(7): 2262-2275, 1990.
Sheffield et al., "Identification of Novel Rhodopsin Mutations Associated with Retinitis Pigmentosa by GC-clamped Denaturing Gradient Gel Electrophoresis" Am. J. Hum. Genet. 49: 699-706, 1991.
Sheffield et al., "Attachment of a 40-base-pair G+C-rich sequence (GC-clamp) to genomic DNA fragments by the polymerase chain reaction results in improved detection of single-base changes" Proc. Natl. Acad. Sci. USA 86: 232-236, 1989.
Shenk et al., "Biochemical Method for Mapping Mutational Alterations in DNA with S1 Nuclease: The Location of Deletions and Temperature-Sensitive Mutations in Simian Virus 40" Proc. Natl. Acad. Sci. USA 72(3): 989-993, 1975.
Siegler et al., "A 20-Year Population-Based Study of Postdiarrheal Hemolytic Uremic Syndrome in Utah" Pediatrics 94: 35-40, 1994.
Slutsker et al., "*Escherichia coli* O157:H7 Diarrhea in the United States: Clinical and Epidemiologic Features" Ann. Intern. Med. 126: 505-513, 1997.
Strockbine et al., "Overview of detection and subtyping methods" *Escherichia coli* O157:H7 and other Shiga toxin-producing *E. coli* strains Chapter 33, Kaper and O'Brien, Eds., Washington, D.C.: ASM Press, 1998, 331-356.
Swerdlow et al., "A Waterborne Outbreak in Missouri of *Escherichia coli* O157:H7 Associated with Bloody Diarrhea and Death" Annals of Internal Medicine 117: 812-819, 1992.
Tarr et al., "The Increasing Incidence of the Hemolytic-Uremic Syndrome in King County, Washington: Lack of Evidence for Ascertainment Bias" American Journal of Epidemiology 129(3): 582-586, 1989.
Tarr et al., "*Escherichia coli* O157:H7 and the Hemolytic Uremic Syndrome: Importance of Early Cultures in Establishing the Etiology" J. Infect. Dis. 162: 553-556, 1990.
Tarr et al., "Hemolytic Uremic Syndrome Epidemiology: A Population-Based Study in King County, Washington, 1971 to 1980" Pediatrics 80: 41-45, 1987.
Tarr, "Shiga toxin-producing *Escherichia coli* infections: challenges and opportunities" *Escherichia coli O157:H7 and other Shiga toxin-producing E. coli strains* Chapter 39, Kaper and O'Brien, Eds., Washington, D.C.: ASM Press, 1998: 393-402.
Tilden et al., "A New Route of Transmission for *Escherichia coli*: Infection from Dry Fermented Salami" American Journal of Public Health 86(8): 1142-1145, 1996.
Tortorello et al., "Antibody-Direct Epifluorescent Filter Technique for Rapid, Direct Enumeration of *Escherichia coli* O157:H7 in Beef" Applied and Environmental Microbiology 60(10): 3553-3559, 1994.
Vernozy-Rozand et al., "Detection of *Escherichia coli* O157 in French food samples using an immunomagnetic separation method and the VIDAS™ *E. coli* O157" Letters in Applied Microbiology 25: 442-446, 1997.
Vernozy-Rozand et al., "A shorter enrichment culture for the isolation of *Escherichia coli* O157:H7 from raw minced beef" Revue de Medecine Veterinaire 148(11): 879-882, 1997. (Abstract).
Vernozy-Rozand et al., "An improved procedure for the detection of *Escherichia coli* O157 in food using an automated screening method" Revue de Medecine Veterinaire 149(3): 239-244, 1998. (Abstract).
Wartell et al., "Detecting base pair substitutions in DNA fragments by temperature-gradient gel electrophoresis" Nucleic Acids Research 18(9): 2699-2705, 1990.
Wells et al., "Laboratory Investigation of Hemorrhagic Colitis Outbreaks Associated with a Rare *Escherichia coli* Serotype" Journal of Clinical Microbiology 18(3): 512-520, 1983.
White et al., "Detecting Single Base Substitutions as Heteroduplex Polymorphisms" Genomics 12: 301-306, 1992.
Whittam et al., "Genetic Polymorphisms and Recombination in Natural Populations of *Escherichia coli*" *Mechanisms of Molecular Evolution*, Takahata et al., eds. Sinauer Associates, Inc.: Sunderland, MA, 223-245, 1993.
Willshaw et al., "Examination of raw beef products for the presence of Vero cytotoxin producing *Escherichia coli*, particularly those of serogroup O157" Journal of Applied Bacteriology 75: 420-426, 1993.
Wilson et al., "Vero Cytotoxigenic *Escherichia coli* Infection in Dairy Farm Families" J. Infect. Dis. 174: 1021-1027, 1996.
Yu et al., Immunomagnetic-Electrochemiluminescent Detection of *Escherichia coli* O157 and *Salmonella typhimurium* in Foods and Environmental Water Samples Applied and Environmental Microbiology 62(2): 587-592, 1996.

\* cited by examiner

FIG. 1

| | Serotype (strain) |
|---|---|
| gnd polymorphic sites | |
| 5'  3' | |
| | O157:H16 (13A81) |
| | O157:H45 (3584-91) |
| | O157:H3 (3004-89) |
| | O157:H16 (3260-92) |
| | O157:H12 (G5933) |
| | O157:H38 (3005-89) |
| | O157:H43 (DEC7E) |
| | O157:H7 (8507) |
| | O157:H7 (86-24) |
| | O157:H7 (ADAL233) |
| | O157:H7 (H8) |
| | O157:H- (2755) |
| | O157:H7 (87-16) |
| | O55:H7 (TB182A) |
| | O55:H6 (DEC1A) |
| | O55:H6 (DEC1B) |
| | O55:H6 (DEC2A) |
| | O55:H6 (DEC2B) |

```
                        SEQUENCE LISTING

<160> NUMBER OF SEQ ID NOS: 43

<210> SEQ ID NO 1
<211> LENGTH: 29
<212> TYPE: DNA
<213> ORGANISM: Artificial Sequence
<220> FEATURE:
<223> OTHER INFORMATION: Primer

<400> SEQUENCE: 1
cacggatccg atcacacctg acaggagta                                           29

<210> SEQ ID NO 2
<211> LENGTH: 33
<212> TYPE: DNA
<213> ORGANISM: Artificial Sequence
<220> FEATURE:
<223> OTHER INFORMATION: Primer

<400> SEQUENCE: 2
ccggaattcc gggcaaaaaa aagcccggtg caa                                      33

<210> SEQ ID NO 3
<211> LENGTH: 32
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: 24
<223> OTHER INFORMATION: n = A,T,C or G

<400> SEQUENCE: 3
cggaattccg cgctcaacat cganagccgt gg                                       32

<210> SEQ ID NO 4
<211> LENGTH: 29
```

```
<212> TYPE: DNA
<213> ORGANISM: Artificial Sequence
<220> FEATURE:
<223> OTHER INFORMATION: Primer

<400> SEQUENCE: 4
cggaattccg cctggatcag gttagccgg                                    29

<210> SEQ ID NO 5
<211> LENGTH: 36
<212> TYPE: DNA
<213> ORGANISM: Artificial Sequence
<220> FEATURE:
<223> OTHER INFORMATION: Primer

<400> SEQUENCE: 5
cggggtaccc cgtaagggac cagtttctta cctggg                            36

<210> SEQ ID NO 6
<211> LENGTH: 18
<212> TYPE: DNA
<213> ORGANISM: Artificial Sequence
<220> FEATURE:
<223> OTHER INFORMATION: Primer

<400> SEQUENCE: 6
gccctatcta gataaagg                                                18

<210> SEQ ID NO 7
<211> LENGTH: 18
<212> TYPE: DNA
<213> ORGANISM: Artificial Sequence
<220> FEATURE:
<223> OTHER INFORMATION: Primer

<400> SEQUENCE: 7
agttaaagcc ttccgcgg                                                18

<210> SEQ ID NO 8
<211> LENGTH: 18
<212> TYPE: DNA
<213> ORGANISM: Artificial Sequence
<220> FEATURE:
<223> OTHER INFORMATION: Primer

<400> SEQUENCE: 8
tgcccgctac atctcctc                                                18

<210> SEQ ID NO 9
<211> LENGTH: 18
<212> TYPE: DNA
<213> ORGANISM: Artificial Sequence
<220> FEATURE:
<223> OTHER INFORMATION: Primer

<400> SEQUENCE: 9
gttgtactct tcagacgc                                                18

<210> SEQ ID NO 10
<211> LENGTH: 24
<212> TYPE: DNA
<213> ORGANISM: Artificial Sequence
<220> FEATURE:
<223> OTHER INFORMATION: Primer

<400> SEQUENCE: 10
tcgtcgctta tgcggtacag agcg                                         24
```

<210> SEQ ID NO 11
<211> LENGTH: 25
<212> TYPE: DNA
<213> ORGANISM: Artificial Sequence
<220> FEATURE:
<223> OTHER INFORMATION: Primer

<400> SEQUENCE: 11
ccatcagtaa taatgaaaag gaatt                                    25

<210> SEQ ID NO 12
<211> LENGTH: 24
<212> TYPE: DNA
<213> ORGANISM: Artificial Sequence
<220> FEATURE:
<223> OTHER INFORMATION: Primer

<400> SEQUENCE: 12
atcattagct cctcttaaga tcgc                                     24

<210> SEQ ID NO 13
<211> LENGTH: 20
<212> TYPE: DNA
<213> ORGANISM: Artificial Sequence
<220> FEATURE:
<223> OTHER INFORMATION: Primer

<400> SEQUENCE: 13
gcgttcttaa agagtcctgc                                          20

<210> SEQ ID NO 14
<211> LENGTH: 11
<212> TYPE: DNA
<213> ORGANISM: Artificial Sequence
<220> FEATURE:
<223> OTHER INFORMATION: Primer

<400> SEQUENCE: 14
agcttgccct g                                                   11

<210> SEQ ID NO 15
<211> LENGTH: 10
<212> TYPE: DNA
<213> ORGANISM: Artificial Sequence
<220> FEATURE:
<223> OTHER INFORMATION: Primer

<400> SEQUENCE: 15
cagggaagat                                                     10

<210> SEQ ID NO 16
<211> LENGTH: 1407
<212> TYPE: DNA
<213> ORGANISM: Escherichia coli
<220> FEATURE:
<221> NAME/KEY: CDS
<222> LOCATION: (1)...(1407)

<400> SEQUENCE: 16

```
atg tca aag caa cag atc ggc gta gtc ggt atg gca gtg atg ggg cgc     48
Met Ser Lys Gln Gln Ile Gly Val Val Gly Met Ala Val Met Gly Arg
1               5                   10                  15 aac ctt gcg ctc aac atc gaa agc cgt ggt tat acc gtc tct att ttc     96
Asn Leu Ala Leu Asn Ile Glu Ser Arg Gly Tyr Thr Val Ser Ile Phe
            20                  25                  30
```

```
aac cgt tcc cgt gaa aag acg gaa gaa gtg att gcc gaa aat cca ggc      144
Asn Arg Ser Arg Glu Lys Thr Glu Glu Val Ile Ala Glu Asn Pro Gly
        35                  40                  45 aag aaa ctg gtt cct tac tat acg gtg aaa gaa ttt gtt gaa tct ctg      192
Lys Lys Leu Val Pro Tyr Tyr Thr Val Lys Glu Phe Val Glu Ser Leu
 50                  55                  60 gaa acg cct cgt cgc atc ttg tta atg gtg aaa gca ggt gca ggc acg      240
Glu Thr Pro Arg Arg Ile Leu Leu Met Val Lys Ala Gly Ala Gly Thr
 65                  70                  75                  80 gat gct gct att gat tcc ctt aag cca tac ctc gat aaa ggt gac atc      288
Asp Ala Ala Ile Asp Ser Leu Lys Pro Tyr Leu Asp Lys Gly Asp Ile
                 85                  90                  95 atc att gat ggt ggt aat acc ttc ttc cag gac acc att cgt cgt aac      336
Ile Ile Asp Gly Gly Asn Thr Phe Phe Gln Asp Thr Ile Arg Arg Asn
            100                 105                 110 cgt gag ctt tct gca gaa ggc ttt aac ttc atc ggt acc ggt gtt tcc      384
Arg Glu Leu Ser Ala Glu Gly Phe Asn Phe Ile Gly Thr Gly Val Ser
            115                 120                 125 ggt ggt gag gag ggc gca cta aaa ggt cct tcc att atg cct ggt ggg      432
Gly Gly Glu Glu Gly Ala Leu Lys Gly Pro Ser Ile Met Pro Gly Gly
130                 135                 140 cag aaa gaa gcc tat gaa cta gtt gcg ccg atc ctg acc aaa atc gcc      480
Gln Lys Glu Ala Tyr Glu Leu Val Ala Pro Ile Leu Thr Lys Ile Ala
145                 150                 155                 160 gca gtg gct gaa gac ggt gag cca tgc gtt acc tat att ggt gcc gat      528
Ala Val Ala Glu Asp Gly Glu Pro Cys Val Thr Tyr Ile Gly Ala Asp
                165                 170                 175 ggc gca ggt cac tat gtg aag atg gtt cac aac ggt att gaa tac ggc      576
Gly Ala Gly His Tyr Val Lys Met Val His Asn Gly Ile Glu Tyr Gly
            180                 185                 190 gat atg cag ctg att gct gaa gcc tat tct ctg ctt aaa ggt ggt ctg      624
Asp Met Gln Leu Ile Ala Glu Ala Tyr Ser Leu Leu Lys Gly Gly Leu
            195                 200                 205 aac ctc acc aac gaa gaa ctg gcg cag atc ttt acc gag tgg aat aac      672
Asn Leu Thr Asn Glu Glu Leu Ala Gln Ile Phe Thr Glu Trp Asn Asn
210                 215                 220 ggt gaa ctg agc agc tac ctg atc gac att acc aaa gac atc ttc act      720
Gly Glu Leu Ser Ser Tyr Leu Ile Asp Ile Thr Lys Asp Ile Phe Thr
225                 230                 235                 240 aaa aaa gat gaa gac ggt aac tac ctg gtt gat gtg atc ctg gat gaa      768
Lys Lys Asp Glu Asp Gly Asn Tyr Leu Val Asp Val Ile Leu Asp Glu
                245                 250                 255 gcg gca aac aaa ggt acg ggc aaa tgg acc agc cag agc gca ctg gat      816
Ala Ala Asn Lys Gly Thr Gly Lys Trp Thr Ser Gln Ser Ala Leu Asp
            260                 265                 270 ctc ggc gaa ccg ctg tcg ctg att acc gag tct gtg ttt gca cga tac      864
Leu Gly Glu Pro Leu Ser Leu Ile Thr Glu Ser Val Phe Ala Arg Tyr
            275                 280                 285 atc tct tct ctg aaa gat cag cgc gtt gct gcg tct aaa gtt ctc tct      912
Ile Ser Ser Leu Lys Asp Gln Arg Val Ala Ala Ser Lys Val Leu Ser
            290                 295                 300 ggc cca caa gcg cag cca gct ggc gac aag gct gag ttc atc gaa aaa      960
Gly Pro Gln Ala Gln Pro Ala Gly Asp Lys Ala Glu Phe Ile Glu Lys
305                 310                 315                 320 gtt cgc cgt gca ctg tat ctg ggc aaa atc gtt tct tac gct cag ggg     1008
Val Arg Arg Ala Leu Tyr Leu Gly Lys Ile Val Ser Tyr Ala Gln Gly
                325                 330                 335 ttc tct caa ctg cgt gcg gcg tct gaa gag tac aac tgg gat ctg aac     1056
Phe Ser Gln Leu Arg Ala Ala Ser Glu Glu Tyr Asn Trp Asp Leu Asn
            340                 345                 350
```

```
tac ggc gaa atc gcg aag att ttc cgt gct ggc tgc atc atc cgt gcg     1104
Tyr Gly Glu Ile Ala Lys Ile Phe Arg Ala Gly Cys Ile Ile Arg Ala
            355                 360                 365 cag ttc ctg cag aaa atc acc gat gct tat gcc gaa aat ccg cag atc     1152
Gln Phe Leu Gln Lys Ile Thr Asp Ala Tyr Ala Glu Asn Pro Gln Ile
370                 375                 380 gct aac ctg ctg ctg gct cct tac ttc aag caa att gcc gat gac tac     1200
Ala Asn Leu Leu Leu Ala Pro Tyr Phe Lys Gln Ile Ala Asp Asp Tyr
385                 390                 395                 400 cag cag gcg ctg cgc gat gtc gtc gct tat gcg gta cag aac ggt atc     1248
Gln Gln Ala Leu Arg Asp Val Val Ala Tyr Ala Val Gln Asn Gly Ile
                405                 410                 415 ccg gtt ccg acc ttc gcc gct gcg gtt gcc tat tat gac agc tac cgc     1296
Pro Val Pro Thr Phe Ala Ala Ala Val Ala Tyr Tyr Asp Ser Tyr Arg
            420                 425                 430 gcc gct gtt ctg cct gcg aac ctg atc cag gca cag cgt gac tat ttc     1344
Ala Ala Val Leu Pro Ala Asn Leu Ile Gln Ala Gln Arg Asp Tyr Phe
                435                 440                 445 ggt gcg cat act tat aag cgc att gat aaa gaa ggt gtg ttc cat acc     1392
Gly Ala His Thr Tyr Lys Arg Ile Asp Lys Glu Gly Val Phe His Thr
450                 455                 460 gaa tgg ctg gat taa                                                 1407
Glu Trp Leu Asp  *
465

<210> SEQ ID NO 17
<211> LENGTH: 467
<212> TYPE: PRT
<213> ORGANISM: Escherichia coli

<400> SEQUENCE: 17

Ser Lys Gln Gln Ile Gly Val Val Gly Met Ala Val Met Gly Arg Asn
1               5                   10                  15

Leu Ala Leu Asn Ile Glu Ser Arg Gly Tyr Thr Val Ser Ile Phe Asn
            20                  25                  30

Arg Ser Arg Glu Lys Thr Glu Glu Val Ile Ala Glu Asn Pro Gly Lys
        35                  40                  45

Lys Leu Val Pro Tyr Tyr Thr Val Lys Glu Phe Val Glu Ser Leu Glu
    50                  55                  60

Thr Pro Arg Arg Ile Leu Leu Met Val Lys Ala Gly Ala Gly Thr Asp
65                  70                  75                  80

Ala Ala Ile Asp Ser Leu Lys Pro Tyr Leu Asp Lys Gly Asp Ile Ile
                85                  90                  95

Ile Asp Gly Gly Asn Thr Phe Phe Gln Asp Thr Ile Arg Arg Asn Arg
            100                 105                 110

Glu Leu Ser Ala Glu Gly Phe Asn Phe Ile Gly Thr Gly Val Ser Gly
        115                 120                 125

Gly Glu Glu Gly Ala Leu Lys Gly Pro Ser Ile Met Pro Gly Gly Gln
    130                 135                 140

Lys Glu Ala Tyr Glu Leu Val Ala Pro Ile Leu Thr Lys Ile Ala Ala
145                 150                 155                 160

Val Ala Glu Asp Gly Glu Pro Cys Val Thr Tyr Ile Gly Ala Asp Gly
                165                 170                 175

Ala Gly His Tyr Val Lys Met Val His Asn Gly Ile Glu Tyr Gly Asp
            180                 185                 190

Met Gln Leu Ile Ala Glu Ala Tyr Ser Leu Leu Lys Gly Gly Leu Asn
        195                 200                 205

Leu Thr Asn Glu Glu Leu Ala Gln Ile Phe Thr Glu Trp Asn Asn Gly
```

```
                 210                 215                 220
Glu Leu Ser Ser Tyr Leu Ile Asp Ile Thr Lys Asp Ile Phe Thr Lys
225                 230                 235                 240

Lys Asp Glu Asp Gly Asn Tyr Leu Val Asp Val Ile Leu Asp Glu Ala
                245                 250                 255

Ala Asn Lys Gly Thr Gly Lys Trp Thr Ser Gln Ser Ala Leu Asp Leu
            260                 265                 270

Gly Glu Pro Leu Ser Leu Ile Thr Glu Ser Val Phe Ala Arg Tyr Ile
        275                 280                 285

Ser Ser Leu Lys Asp Gln Arg Val Ala Ala Ser Lys Val Leu Ser Gly
290                 295                 300

Pro Gln Ala Gln Pro Ala Gly Asp Lys Ala Glu Phe Ile Glu Lys Val
305                 310                 315                 320

Arg Arg Ala Leu Tyr Leu Gly Lys Ile Val Ser Tyr Ala Gln Gly Phe
                325                 330                 335

Ser Gln Leu Arg Ala Ala Ser Glu Glu Tyr Asn Trp Asp Leu Asn Tyr
            340                 345                 350

Gly Glu Ile Ala Lys Ile Phe Arg Ala Gly Cys Ile Ile Arg Ala Gln
        355                 360                 365

Phe Leu Gln Lys Ile Thr Asp Ala Tyr Ala Glu Asn Pro Gln Ile Ala
370                 375                 380

Asn Leu Leu Leu Ala Pro Tyr Phe Lys Gln Ile Ala Asp Tyr Gln
385                 390                 395                 400

Gln Ala Leu Arg Asp Val Val Ala Tyr Ala Val Gln Asn Gly Ile Pro
                405                 410                 415

Val Pro Thr Phe Ala Ala Ala Val Ala Tyr Tyr Asp Ser Tyr Arg Ala
            420                 425                 430

Ala Val Leu Pro Ala Asn Leu Ile Gln Ala Gln Arg Asp Tyr Phe Gly
        435                 440                 445

Ala His Thr Tyr Lys Arg Ile Asp Lys Glu Gly Val Phe His Thr Glu
450                 455                 460

Trp Leu Asp
465

<210> SEQ ID NO 18
<211> LENGTH: 1407
<212> TYPE: DNA
<213> ORGANISM: Escherichia coli
<220> FEATURE:
<221> NAME/KEY: CDS
<222> LOCATION: (1)...(1407)

<400> SEQUENCE: 18 atg tca aag caa cag atc ggc gta gtc ggt atg gca gtg atg ggg cgc     48
Met Ser Lys Gln Gln Ile Gly Val Val Gly Met Ala Val Met Gly Arg
1               5                   10                  15 aac ctt gcg ctc aac atc gaa agc cgt ggt tat acc gtc tct att ttc     96
Asn Leu Ala Leu Asn Ile Glu Ser Arg Gly Tyr Thr Val Ser Ile Phe
            20                  25                  30 aac cgt tcc cgt gaa aag acg gaa gaa gtg att gcc gaa aat cca ggc    144
Asn Arg Ser Arg Glu Lys Thr Glu Glu Val Ile Ala Glu Asn Pro Gly
        35                  40                  45 aag aaa ctg gtt cct tac tat acg gtg aaa gaa ttt gtt gaa tct ctg    192
Lys Lys Leu Val Pro Tyr Tyr Thr Val Lys Glu Phe Val Glu Ser Leu
    50                  55                  60 gaa acg cct cgt cgc atc ttg tta atg gtg aaa gca ggt gca ggc acg    240
Glu Thr Pro Arg Arg Ile Leu Leu Met Val Lys Ala Gly Ala Gly Thr
65                  70                  75                  80
```

-continued

| | | |
|---|---|---|
| gat gct gct att gat tcc ctt aag cca tac ctc gat aaa ggt gac atc<br>Asp Ala Ala Ile Asp Ser Leu Lys Pro Tyr Leu Asp Lys Gly Asp Ile<br>                      85                        90                    95 | 288 |
| atc att gat ggt ggt aat acc ttc ttc cag gac acc att cgt cgt aac<br>Ile Ile Asp Gly Gly Asn Thr Phe Phe Gln Asp Thr Ile Arg Arg Asn<br>               100                      105                    110 | 336 |
| cgt gag ctt tct gca gaa ggc ttt aac ttc atc ggt acc ggt gtt tcc<br>Arg Glu Leu Ser Ala Glu Gly Phe Asn Phe Ile Gly Thr Gly Val Ser<br>               115                      120                    125 | 384 |
| ggt ggt gag gag ggc gca cta aaa ggt cct tcc att atg cct ggt ggg<br>Gly Gly Glu Glu Gly Ala Leu Lys Gly Pro Ser Ile Met Pro Gly Gly<br>130                        135                      140 | 432 |
| cag aaa gaa gcc tat gaa cta gtt gcg ccg atc ctg acc aaa atc gcc<br>Gln Lys Glu Ala Tyr Glu Leu Val Ala Pro Ile Leu Thr Lys Ile Ala<br>145                        150                      155                    160 | 480 |
| gca gtg gct gaa gac ggt gag cca tgc gtt acc tat att ggt gcc gat<br>Ala Val Ala Glu Asp Gly Glu Pro Cys Val Thr Tyr Ile Gly Ala Asp<br>               165                      170                    175 | 528 |
| ggc gca ggt cac tat gtg aag atg gtt cac aac ggt att gaa tac ggc<br>Gly Ala Gly His Tyr Val Lys Met Val His Asn Gly Ile Glu Tyr Gly<br>               180                      185                    190 | 576 |
| gat atg cag ctg att gct gaa gcc tat tct ctg ctt aaa ggt ggt ctg<br>Asp Met Gln Leu Ile Ala Glu Ala Tyr Ser Leu Leu Lys Gly Gly Leu<br>               195                      200                    205 | 624 |
| aac ctc acc aac gaa gaa ctg gcg cag atc ttt acc gag tgg aat aac<br>Asn Leu Thr Asn Glu Glu Leu Ala Gln Ile Phe Thr Glu Trp Asn Asn<br>               210                      215                    220 | 672 |
| ggt gaa ctg agc agc tac ctg atc gac att acc aaa gac atc ttc act<br>Gly Glu Leu Ser Ser Tyr Leu Ile Asp Ile Thr Lys Asp Ile Phe Thr<br>225                        230                      235                    240 | 720 |
| aaa aaa gat gaa gac ggt aac tac ctg gtt gat gtg atc ctg gat gaa<br>Lys Lys Asp Glu Asp Gly Asn Tyr Leu Val Asp Val Ile Leu Asp Glu<br>                        245                      250                    255 | 768 |
| gcg gca aac aaa ggt acg ggc aaa tgg acc agc cag agc gca ctg gat<br>Ala Ala Asn Lys Gly Thr Gly Lys Trp Thr Ser Gln Ser Ala Leu Asp<br>               260                      265                    270 | 816 |
| ctc ggc gaa ccg ctg tcg ctg att acc gag tct gtg ttt gca cga tac<br>Leu Gly Glu Pro Leu Ser Leu Ile Thr Glu Ser Val Phe Ala Arg Tyr<br>               275                      280                    285 | 864 |
| atc tct tct ctg aaa gat cag cgc gtt gct gcg tct aaa gtt ctc tct<br>Ile Ser Ser Leu Lys Asp Gln Arg Val Ala Ala Ser Lys Val Leu Ser<br>               290                      295                    300 | 912 |
| ggc cca caa gcg cag cca gct ggc gac aag gct gag ttc atc gaa aaa<br>Gly Pro Gln Ala Gln Pro Ala Gly Asp Lys Ala Glu Phe Ile Glu Lys<br>305                        310                      315                    320 | 960 |
| gtt cgc cgt gca ctg tat ctg ggc aaa atc gtt tct tac gct cag ggg<br>Val Arg Arg Ala Leu Tyr Leu Gly Lys Ile Val Ser Tyr Ala Gln Gly<br>               325                      330                    335 | 1008 |
| ttc tct caa ctg cgt gcg gcg tct gaa gag tac aac tgg gat ctg aac<br>Phe Ser Gln Leu Arg Ala Ala Ser Glu Glu Tyr Asn Trp Asp Leu Asn<br>               340                      345                    350 | 1056 |
| tac ggc gaa atc gcg aag att ttc cgt gct ggc tgc atc atc cgt gcg<br>Tyr Gly Glu Ile Ala Lys Ile Phe Arg Ala Gly Cys Ile Ile Arg Ala<br>               355                      360                    365 | 1104 |
| cag ttc ctg cag aaa atc acc gat gct tat gcc gaa aat ccg cag atc<br>Gln Phe Leu Gln Lys Ile Thr Asp Ala Tyr Ala Glu Asn Pro Gln Ile<br>               370                      375                    380 | 1152 |
| gct aac ctg ctg ctg gct cct tac ttc aag caa att gcc gat gac tac<br>Ala Asn Leu Leu Leu Ala Pro Tyr Phe Lys Gln Ile Ala Asp Asp Tyr<br>385                        390                      395                    400 | 1200 |

```
cag cag gcg ctg cgc gat gtc gtc gct tat gcg gta cag aac ggt atc          1248
Gln Gln Ala Leu Arg Asp Val Val Ala Tyr Ala Val Gln Asn Gly Ile
            405                 410                 415 ccg gtt ccg acc ttc gcc gct gcg gtt gcc tat tat gac agc tac cgc          1296
Pro Val Pro Thr Phe Ala Ala Ala Val Ala Tyr Tyr Asp Ser Tyr Arg
            420                 425                 430 gcc gct gtt ctg cct gcg aac ctg atc cag gca cag cgt gac tat ttc          1344
Ala Ala Val Leu Pro Ala Asn Leu Ile Gln Ala Gln Arg Asp Tyr Phe
            435                 440                 445 ggt gcg cat act tat aag cgc att gat aaa gaa ggt gtg ttc cat acc          1392
Gly Ala His Thr Tyr Lys Arg Ile Asp Lys Glu Gly Val Phe His Thr
        450                 455                 460 gaa tgg ctg gat taa                                                      1407
Glu Trp Leu Asp *
465

<210> SEQ ID NO 19
<211> LENGTH: 467
<212> TYPE: PRT
<213> ORGANISM: Escherichia coli

<400> SEQUENCE: 19

Ser Lys Gln Gln Ile Gly Val Val Gly Met Ala Val Met Gly Arg Asn
1               5                   10                  15

Leu Ala Leu Asn Ile Glu Ser Arg Gly Tyr Thr Val Ser Ile Phe Asn
                20                  25                  30

Arg Ser Arg Glu Lys Thr Glu Glu Val Ile Ala Glu Asn Pro Gly Lys
            35                  40                  45

Lys Leu Val Pro Tyr Tyr Thr Val Lys Glu Phe Val Glu Ser Leu Glu
        50                  55                  60

Thr Pro Arg Arg Ile Leu Leu Met Val Lys Ala Gly Ala Gly Thr Asp
65                  70                  75                  80

Ala Ala Ile Asp Ser Leu Lys Pro Tyr Leu Asp Lys Gly Asp Ile Ile
                85                  90                  95

Ile Asp Gly Gly Asn Thr Phe Phe Gln Asp Thr Ile Arg Arg Asn Arg
            100                 105                 110

Glu Leu Ser Ala Glu Gly Phe Asn Phe Ile Gly Thr Gly Val Ser Gly
        115                 120                 125

Gly Glu Glu Gly Ala Leu Lys Gly Pro Ser Ile Met Pro Gly Gly Gln
    130                 135                 140

Lys Glu Ala Tyr Glu Leu Val Ala Pro Ile Leu Thr Lys Ile Ala Ala
145                 150                 155                 160

Val Ala Glu Asp Gly Glu Pro Cys Val Thr Tyr Ile Gly Ala Asp Gly
                165                 170                 175

Ala Gly His Tyr Val Lys Met Val His Asn Gly Ile Glu Tyr Gly Asp
            180                 185                 190

Met Gln Leu Ile Ala Glu Ala Tyr Ser Leu Leu Lys Gly Gly Leu Asn
        195                 200                 205

Leu Thr Asn Glu Glu Leu Ala Gln Ile Phe Thr Glu Trp Asn Asn Gly
    210                 215                 220

Glu Leu Ser Ser Tyr Leu Ile Asp Ile Thr Lys Asp Ile Phe Thr Lys
225                 230                 235                 240

Lys Asp Glu Asp Gly Asn Tyr Leu Val Asp Val Ile Leu Asp Glu Ala
                245                 250                 255

Ala Asn Lys Gly Thr Gly Lys Trp Thr Ser Gln Ser Ala Leu Asp Leu
            260                 265                 270
```

```
Gly Glu Pro Leu Ser Leu Ile Thr Glu Ser Val Phe Ala Arg Tyr Ile
            275                 280                 285

Ser Ser Leu Lys Asp Gln Arg Val Ala Ala Ser Lys Val Leu Ser Gly
290                 295                 300

Pro Gln Ala Gln Pro Ala Gly Asp Lys Ala Glu Phe Ile Glu Lys Val
305                 310                 315                 320

Arg Arg Ala Leu Tyr Leu Gly Lys Ile Val Ser Tyr Ala Gln Gly Phe
                325                 330                 335

Ser Gln Leu Arg Ala Ala Ser Glu Glu Tyr Asn Trp Asp Leu Asn Tyr
                340                 345                 350

Gly Glu Ile Ala Lys Ile Phe Arg Ala Gly Cys Ile Ile Arg Ala Gln
            355                 360                 365

Phe Leu Gln Lys Ile Thr Asp Ala Tyr Ala Glu Asn Pro Gln Ile Ala
370                 375                 380

Asn Leu Leu Leu Ala Pro Tyr Phe Lys Gln Ile Ala Asp Asp Tyr Gln
385                 390                 395                 400

Gln Ala Leu Arg Asp Val Val Ala Tyr Ala Val Gln Asn Gly Ile Pro
                405                 410                 415

Val Pro Thr Phe Ala Ala Val Ala Tyr Tyr Asp Ser Tyr Arg Ala
                420                 425                 430

Ala Val Leu Pro Ala Asn Leu Ile Gln Ala Gln Arg Asp Tyr Phe Gly
            435                 440                 445

Ala His Thr Tyr Lys Arg Ile Asp Lys Glu Gly Val Phe His Thr Glu
        450                 455                 460

Trp Leu Asp
465

<210> SEQ ID NO 20
<211> LENGTH: 1407
<212> TYPE: DNA
<213> ORGANISM: Escherichia coli
<220> FEATURE:
<221> NAME/KEY: CDS
<222> LOCATION: (1)...(1407)

<400> SEQUENCE: 20 atg tca aag caa cag atc ggc gta gtc ggt atg gca gtg atg ggg cgc     48
Met Ser Lys Gln Gln Ile Gly Val Val Gly Met Ala Val Met Gly Arg
1               5                   10                  15 aac ctt gcg ctc aac atc gaa agc cgt ggt tat acc gtc tct att ttc     96
Asn Leu Ala Leu Asn Ile Glu Ser Arg Gly Tyr Thr Val Ser Ile Phe
                20                  25                  30 aac cgt tcc cgt gaa aag acg gaa gaa gtg att gcc gaa aat cca ggc    144
Asn Arg Ser Arg Glu Lys Thr Glu Glu Val Ile Ala Glu Asn Pro Gly
        35                  40                  45 aag aaa ctg gtt cct tac tat acg gtg aaa gaa ttt gtt gaa tct ctg    192
Lys Lys Leu Val Pro Tyr Tyr Thr Val Lys Glu Phe Val Glu Ser Leu
50                  55                  60 gaa acg cct cgt cgc atc ttg tta atg gtg aaa gca ggt gca ggc acg    240
Glu Thr Pro Arg Arg Ile Leu Leu Met Val Lys Ala Gly Ala Gly Thr
65                  70                  75                  80 gat gct gct att gat tcc ctt aag cca tac ctc gat aaa ggt gac atc    288
Asp Ala Ala Ile Asp Ser Leu Lys Pro Tyr Leu Asp Lys Gly Asp Ile
                85                  90                  95 atc att gat ggt ggt aat acc ttc ttc cag gac acc att cgt cgt aac    336
Ile Ile Asp Gly Gly Asn Thr Phe Phe Gln Asp Thr Ile Arg Arg Asn
            100                 105                 110 cgt gag ctt tct gca gaa ggc ttt aac ttc atc ggt acc ggt gtt tcc    384
Arg Glu Leu Ser Ala Glu Gly Phe Asn Phe Ile Gly Thr Gly Val Ser
```

```
              115                 120                 125
ggt ggt gag gag ggc gca cta aaa ggt cct tcc att atg cct ggt ggg      432
Gly Gly Glu Glu Gly Ala Leu Lys Gly Pro Ser Ile Met Pro Gly Gly
130                 135                 140 cag aaa gaa gcc tat gaa cta gtt gcg ccg atc ctg acc aaa atc gcc      480
Gln Lys Glu Ala Tyr Glu Leu Val Ala Pro Ile Leu Thr Lys Ile Ala
145                 150                 155                 160 gca gtg gct gaa gac ggt gag cca tgc gtt acc tat att ggt gcc gat      528
Ala Val Ala Glu Asp Gly Glu Pro Cys Val Thr Tyr Ile Gly Ala Asp
                165                 170                 175 ggc gca ggt cac tat gtg aag atg gtt cac aac ggt att gaa tac ggc      576
Gly Ala Gly His Tyr Val Lys Met Val His Asn Gly Ile Glu Tyr Gly
            180                 185                 190 gat atg cag ctg att gct gaa gcc tat tct ctg ctt aaa ggt ggt ctg      624
Asp Met Gln Leu Ile Ala Glu Ala Tyr Ser Leu Leu Lys Gly Gly Leu
        195                 200                 205 aac ctc acc aac gaa gaa ctg gcg cag atc ttt acc gag tgg aat aac      672
Asn Leu Thr Asn Glu Glu Leu Ala Gln Ile Phe Thr Glu Trp Asn Asn
210                 215                 220 ggt gaa ctg agc agc tac ctg atc gac att acc aaa gac atc ttc act      720
Gly Glu Leu Ser Ser Tyr Leu Ile Asp Ile Thr Lys Asp Ile Phe Thr
225                 230                 235                 240 aaa aaa gat gaa gac ggt aac tac ctg gtt gat gtg atc ctg gat gaa      768
Lys Lys Asp Glu Asp Gly Asn Tyr Leu Val Asp Val Ile Leu Asp Glu
                245                 250                 255 gcg gca aac aaa ggt acg ggc aaa tgg acc agc cag agc gca ctg gat      816
Ala Ala Asn Lys Gly Thr Gly Lys Trp Thr Ser Gln Ser Ala Leu Asp
            260                 265                 270 ctc ggc gaa ccg ctg tcg ctg att acc gag tct gtg ttt gca cga tac      864
Leu Gly Glu Pro Leu Ser Leu Ile Thr Glu Ser Val Phe Ala Arg Tyr
        275                 280                 285 atc tct tct ctg aaa gat cag cgc gtt gct gcg tct aaa gtt ctc tct      912
Ile Ser Ser Leu Lys Asp Gln Arg Val Ala Ala Ser Lys Val Leu Ser
290                 295                 300 ggc cca caa gcg cag cca gct ggc gac aag gct gag ttc atc gaa aaa      960
Gly Pro Gln Ala Gln Pro Ala Gly Asp Lys Ala Glu Phe Ile Glu Lys
305                 310                 315                 320 gtt cgc cgt gca ctg tat ctg ggc aaa atc gtt tct tac gct cag ggg     1008
Val Arg Arg Ala Leu Tyr Leu Gly Lys Ile Val Ser Tyr Ala Gln Gly
                325                 330                 335 ttc tct caa ctg cgt gcg gcg tct gaa gag tac aac tgg gat ctg aac     1056
Phe Ser Gln Leu Arg Ala Ala Ser Glu Glu Tyr Asn Trp Asp Leu Asn
            340                 345                 350 tac ggc gaa atc gcg aag att ttc cgt gct ggc tgc atc atc cgt gcg     1104
Tyr Gly Glu Ile Ala Lys Ile Phe Arg Ala Gly Cys Ile Ile Arg Ala
        355                 360                 365 cag ttc ctg cag aaa atc acc gat gct tat gcc gaa aat ccg cag atc     1152
Gln Phe Leu Gln Lys Ile Thr Asp Ala Tyr Ala Glu Asn Pro Gln Ile
370                 375                 380 gct aac ctg ctg ctg gct cct tac ttc aag caa att gcc gat gac tac     1200
Ala Asn Leu Leu Leu Ala Pro Tyr Phe Lys Gln Ile Ala Asp Asp Tyr
385                 390                 395                 400 cag cag gcg ctg cgc gat gtc gtc gct tat gcg gta cag aac ggt atc     1248
Gln Gln Ala Leu Arg Asp Val Val Ala Tyr Ala Val Gln Asn Gly Ile
                405                 410                 415 ccg gtt ccg acc ttc gcc gct gcg gtt gcc tat tat gac agc tac cgc     1296
Pro Val Pro Thr Phe Ala Ala Ala Val Ala Tyr Tyr Asp Ser Tyr Arg
            420                 425                 430 gcc gct gtt ctg cct gcg aac ctg atc cag gca cag cgt gac tat ttc     1344
Ala Ala Val Leu Pro Ala Asn Leu Ile Gln Ala Gln Arg Asp Tyr Phe
```

```
                 435                 440                 445
ggt gcg cat act tat aag cgc att gat aaa gaa ggt gtg ttc cat acc    1392
Gly Ala His Thr Tyr Lys Arg Ile Asp Lys Glu Gly Val Phe His Thr
    450                 455                 460 gaa tgg ctg gat taa                                                1407
Glu Trp Leu Asp *
465

<210> SEQ ID NO 21
<211> LENGTH: 467
<212> TYPE: PRT
<213> ORGANISM: Escherichia coli

<400> SEQUENCE: 21

Ser Lys Gln Gln Ile Gly Val Gly Met Ala Val Met Gly Arg Asn
1               5                   10                  15

Leu Ala Leu Asn Ile Glu Ser Arg Gly Tyr Thr Val Ser Ile Phe Asn
            20                  25                  30

Arg Ser Arg Glu Lys Thr Glu Val Ile Ala Glu Asn Pro Gly Lys
        35                  40                  45

Lys Leu Val Pro Tyr Tyr Thr Val Lys Glu Phe Val Glu Ser Leu Glu
    50                  55                  60

Thr Pro Arg Arg Ile Leu Leu Met Val Lys Ala Gly Ala Gly Thr Asp
65                  70                  75                  80

Ala Ala Ile Asp Ser Leu Lys Pro Tyr Leu Asp Lys Gly Asp Ile Ile
                85                  90                  95

Ile Asp Gly Gly Asn Thr Phe Phe Gln Asp Thr Ile Arg Arg Asn Arg
            100                 105                 110

Glu Leu Ser Ala Glu Gly Phe Asn Phe Ile Gly Thr Gly Val Ser Gly
        115                 120                 125

Gly Glu Glu Gly Ala Leu Lys Gly Pro Ser Ile Met Pro Gly Gly Gln
130                 135                 140

Lys Glu Ala Tyr Glu Leu Val Ala Pro Ile Leu Thr Lys Ile Ala Ala
145                 150                 155                 160

Val Ala Glu Asp Gly Glu Pro Cys Val Thr Tyr Ile Gly Ala Asp Gly
                165                 170                 175

Ala Gly His Tyr Val Lys Met Val His Asn Gly Ile Glu Tyr Gly Asp
            180                 185                 190

Met Gln Leu Ile Ala Glu Ala Tyr Ser Leu Leu Lys Gly Gly Leu Asn
        195                 200                 205

Leu Thr Asn Glu Glu Leu Ala Gln Ile Phe Thr Glu Trp Asn Asn Gly
    210                 215                 220

Glu Leu Ser Ser Tyr Leu Ile Asp Ile Thr Lys Asp Ile Phe Thr Lys
225                 230                 235                 240

Lys Asp Glu Asp Gly Asn Tyr Leu Val Asp Val Ile Leu Asp Glu Ala
                245                 250                 255

Ala Asn Lys Gly Thr Gly Lys Trp Thr Ser Gln Ser Ala Leu Asp Leu
            260                 265                 270

Gly Glu Pro Leu Ser Leu Ile Thr Glu Ser Val Phe Ala Arg Tyr Ile
        275                 280                 285

Ser Ser Leu Lys Asp Gln Arg Val Ala Ala Ser Lys Val Leu Ser Gly
    290                 295                 300

Pro Gln Ala Gln Pro Ala Gly Asp Lys Ala Glu Phe Ile Glu Lys Val
305                 310                 315                 320

Arg Arg Ala Leu Tyr Leu Gly Lys Ile Val Ser Tyr Ala Gln Gly Phe
                325                 330                 335
```

```
Ser Gln Leu Arg Ala Ala Ser Glu Glu Tyr Asn Trp Asp Leu Asn Tyr
            340                 345                 350

Gly Glu Ile Ala Lys Ile Phe Arg Ala Gly Cys Ile Ile Arg Ala Gln
        355                 360                 365

Phe Leu Gln Lys Ile Thr Asp Ala Tyr Ala Glu Asn Pro Gln Ile Ala
    370                 375                 380

Asn Leu Leu Ala Pro Tyr Phe Lys Gln Ile Ala Asp Asp Tyr Gln
385                 390                 395                 400

Gln Ala Leu Arg Asp Val Val Ala Tyr Ala Val Gln Asn Gly Ile Pro
                405                 410                 415

Val Pro Thr Phe Ala Ala Ala Val Ala Tyr Tyr Asp Ser Tyr Arg Ala
            420                 425                 430

Ala Val Leu Pro Ala Asn Leu Ile Gln Ala Gln Arg Asp Tyr Phe Gly
        435                 440                 445

Ala His Thr Tyr Lys Arg Ile Asp Lys Glu Gly Val Phe His Thr Glu
    450                 455                 460

Trp Leu Asp
465

<210> SEQ ID NO 22
<211> LENGTH: 1407
<212> TYPE: DNA
<213> ORGANISM: Escherichia coli

<400> SEQUENCE: 22
atgtcaaagc aacagatcgg cgtagtcggt atggcagtga tggggcgcaa ccttgcgctc      60
aacatcgaaa gccgtggtta taccgtctct attttcaacc gttcccgtga aaagacggaa     120
gaagtgattg ccgaaaatcc aggcaagaaa ctggttcctt actatacggt gaaagaattt     180
gttgaatctc tggaaacgcc tcgtcgcatc ttgttaatgg tgaaagcagg tgcaggcacg     240
gatgctgcta ttgattccct taagccatac ctcgataaag gtgacatcat cattgatggt     300
ggtaatacct tcttccagga caccattcgt cgtaaccgtg agctttctgc agaaggcttt     360
aacttcatcg gtaccggtgt ttccggtggt gaggagggcg cactaaaagg tccttccatt     420
atgcctggtg ggcagaaaga agcctatgaa ctagttgcgc cgatcctgac caaaatcgcc     480
gcagtggctg aagacggtga gccatgcgtt acctatattg tgccgatggc gcaggtcac      540 tatgtgaaga tggttcacaa cggtattgaa tacggcgata tgcagctgat tgctgaagcc     600
tattctctgc ttaaaggtgg tctgaacctc accaacgaag aactggcgca gatctttacc     660
gagtggaata cggtgaact gagcagctac ctgatcgaca ttaccaaaga catcttcact     720
aaaaaagatg aagacggtaa ctacctggtt gatgtgatcc tggatgaagc ggcaaacaaa     780
ggtacgggca atggaccag ccagagcgca ctggatctcg gcgaaccgct gtcgctgatt     840
accgagtctg tgtttgcacg atacatctct tctctgaaag atcagcgcgt tgctgcgtct     900
aaagttctct ctggcccaca agcgcagcca gctggcgaca ggctgagtt catcgaaaaa     960 gttcgccgtg cactgtatct ggcaaaaatc gtttcttacg ctcagggtt ctctcaactg    1020 cgtgcggcgt ctgaagagta caactgggat ctgaactacg gcgaaatcgc gaagattttc    1080
cgtgctggct gcatcatccg tgcgcagttc ctgcagaaaa tcaccgatgc ttatgccgaa    1140
aatccgcaga tcgctaacct gctgctggct ccttacttca gcaaattgc cgatgactac    1200 cagcaggcgc tgcgcgatgt cgtcgcttat gcggtacaga acggtatccc ggttccgacc    1260
ttcgccgctg cggttgccta ttatgacagc taccgcgccg ctgttctgcc tgcgaacctg    1320
```

```
atccaggcac agcgtgacta tttcggtgcg catacttata agcgcattga taaagaaggt    1380
gtgttccata ccgaatggct ggattaa                                        1407
```

<210> SEQ ID NO 23
<211> LENGTH: 468
<212> TYPE: PRT
<213> ORGANISM: Escherichia coli

<400> SEQUENCE: 23

| | | | | | | | | | | | | | | | |
|---|---|---|---|---|---|---|---|---|---|---|---|---|---|---|---|
| Met | Ser | Lys | Gln | Gln | Ile | Gly | Val | Val | Gly | Met | Ala | Val | Met | Gly | Arg |
| 1 | | | | 5 | | | | | 10 | | | | | 15 | |
| Asn | Leu | Ala | Leu | Asn | Ile | Glu | Ser | Arg | Gly | Tyr | Thr | Val | Ser | Ile | Phe |
| | | | 20 | | | | | 25 | | | | | 30 | | |
| Asn | Arg | Ser | Arg | Glu | Lys | Thr | Glu | Glu | Val | Ile | Ala | Glu | Asn | Pro | Gly |
| | | 35 | | | | | 40 | | | | | 45 | | | |
| Lys | Lys | Leu | Val | Pro | Tyr | Tyr | Thr | Val | Lys | Glu | Phe | Val | Glu | Ser | Leu |
| | 50 | | | | | 55 | | | | | 60 | | | | |
| Glu | Thr | Pro | Arg | Arg | Ile | Leu | Leu | Met | Val | Lys | Ala | Gly | Ala | Gly | Thr |
| 65 | | | | | 70 | | | | | 75 | | | | | 80 |
| Asp | Ala | Ala | Ile | Asp | Ser | Leu | Lys | Pro | Tyr | Leu | Asp | Lys | Gly | Asp | Ile |
| | | | | 85 | | | | | 90 | | | | | 95 | |
| Ile | Ile | Asp | Gly | Gly | Asn | Thr | Phe | Phe | Gln | Asp | Thr | Ile | Arg | Arg | Asn |
| | | | 100 | | | | | 105 | | | | | 110 | | |
| Arg | Glu | Leu | Ser | Ala | Glu | Gly | Phe | Asn | Phe | Ile | Gly | Thr | Gly | Val | Ser |
| | | 115 | | | | | 120 | | | | | 125 | | | |
| Gly | Gly | Glu | Glu | Gly | Ala | Leu | Lys | Gly | Pro | Ser | Ile | Met | Pro | Gly | Gly |
| | 130 | | | | | 135 | | | | | 140 | | | | |
| Gln | Lys | Glu | Ala | Tyr | Glu | Leu | Val | Ala | Pro | Ile | Leu | Thr | Lys | Ile | Ala |
| 145 | | | | | 150 | | | | | 155 | | | | | 160 |
| Ala | Val | Ala | Glu | Asp | Gly | Glu | Pro | Cys | Val | Thr | Tyr | Ile | Gly | Ala | Asp |
| | | | | 165 | | | | | 170 | | | | | 175 | |
| Gly | Ala | Gly | His | Tyr | Val | Lys | Met | Val | His | Asn | Gly | Ile | Glu | Tyr | Gly |
| | | | 180 | | | | | 185 | | | | | 190 | | |
| Asp | Met | Gln | Leu | Ile | Ala | Glu | Ala | Tyr | Ser | Leu | Leu | Lys | Gly | Gly | Leu |
| | | 195 | | | | | 200 | | | | | 205 | | | |
| Asn | Leu | Thr | Asn | Glu | Glu | Leu | Ala | Gln | Ile | Phe | Thr | Glu | Trp | Asn | Asn |
| | 210 | | | | | 215 | | | | | 220 | | | | |
| Gly | Glu | Leu | Ser | Ser | Tyr | Leu | Ile | Asp | Ile | Thr | Lys | Asp | Ile | Phe | Thr |
| 225 | | | | | 230 | | | | | 235 | | | | | 240 |
| Lys | Lys | Asp | Glu | Asp | Gly | Asn | Tyr | Leu | Val | Asp | Val | Ile | Leu | Asp | Glu |
| | | | | 245 | | | | | 250 | | | | | 255 | |
| Ala | Ala | Asn | Lys | Gly | Thr | Gly | Lys | Trp | Thr | Ser | Gln | Ser | Ala | Leu | Asp |
| | | | 260 | | | | | 265 | | | | | 270 | | |
| Leu | Gly | Glu | Pro | Leu | Ser | Leu | Ile | Thr | Glu | Ser | Val | Phe | Ala | Arg | Tyr |
| | | 275 | | | | | 280 | | | | | 285 | | | |
| Ile | Ser | Ser | Leu | Lys | Asp | Gln | Arg | Val | Ala | Ala | Ser | Lys | Val | Leu | Ser |
| | 290 | | | | | 295 | | | | | 300 | | | | |
| Gly | Pro | Gln | Ala | Gln | Pro | Ala | Gly | Asp | Lys | Ala | Glu | Phe | Ile | Glu | Lys |
| 305 | | | | | 310 | | | | | 315 | | | | | 320 |
| Val | Arg | Arg | Ala | Leu | Tyr | Leu | Gly | Lys | Ile | Val | Ser | Tyr | Ala | Gln | Gly |
| | | | | 325 | | | | | 330 | | | | | 335 | |
| Phe | Ser | Gln | Leu | Arg | Ala | Ala | Ser | Glu | Glu | Tyr | Asn | Trp | Asp | Leu | Asn |
| | | | 340 | | | | | 345 | | | | | 350 | | |
| Tyr | Gly | Glu | Ile | Ala | Lys | Ile | Phe | Arg | Ala | Gly | Cys | Ile | Ile | Arg | Ala |
| | | 355 | | | | | 360 | | | | | 365 | | | |

Gln Phe Leu Gln Lys Ile Thr Asp Ala Tyr Ala Glu Asn Pro Gln Ile
    370                 375                 380

Ala Asn Leu Leu Leu Ala Pro Tyr Phe Lys Gln Ile Ala Asp Asp Tyr
385                 390                 395                 400

Gln Gln Ala Leu Arg Asp Val Val Ala Tyr Ala Val Gln Asn Gly Ile
                405                 410                 415

Pro Val Pro Thr Phe Ala Ala Val Ala Tyr Tyr Asp Ser Tyr Arg
            420                 425                 430

Ala Ala Val Leu Pro Ala Asn Leu Ile Gln Ala Gln Arg Asp Tyr Phe
            435                 440                 445

Gly Ala His Thr Tyr Lys Arg Ile Asp Lys Glu Gly Val Phe His Thr
    450                 455                 460

Glu Trp Leu Asp
465

<210> SEQ ID NO 24
<211> LENGTH: 1407
<212> TYPE: DNA
<213> ORGANISM: Escherichia coli

<400> SEQUENCE: 24
atgtcaaagc aacagatcgg cgtagtcggt atggcagtga tggggcgcaa ccttgcgccc      60
aacatcgaaa gccgtggtta ccgtctctct attttcaacc gttcccgtga aaagacggaa     120
gaagtgattg ccgaaaatcc aggcaagaaa ctggttcctt actatacggt gaaagaattt     180
gttgaatctc tggaaacgcc tcgtcgcatc ttgttaatgg tgaaagcagg tgcaggcacg     240
gatgctgcta ttgattccct taagccatac ctcgataaag gtgacatcat cattgatagt     300
ggtaatacct tcttccagga caccattcgt cgtaaccgtg agctttctgc agaaggcttt     360
aacttcatcg gtaccggtgt ttccggtggt gaggagggcg cactaaaagg tccttccatt     420
atgcctggtg gcagaaaaga agcctatgaa ctagttgcgc cgatcctgac caaaatcgcc     480
gcagtggctg aagacggtga gccatgcgtt acctatattg gtgccgatgg cgcaggtcac     540
tatgtgaaga tggttcacaa cggtattgaa tacggcgata tgcagctgat tgctgaagcc     600
tattctctgc ttaaaggtgg tctgaacctc accaacgaag aactggcgca gatctttacc     660
gagtggaata cggtgaact gagcagctac ctgatcgaca ttaccaaaga catcttcact     720
aaaaaagatg aagacggtaa ctacctggtt gatgtgatcc tggatgaagc ggcaaacaaa     780
ggtacgggca atggaccag ccagagcgca ctggatctcg cgaaccgct gtcgctgatt     840 accgagtctg tgtttgcacg atacatctct tctctgaaag atcagcgcgt tgctgcgtct     900
aaagttctct ctggcccaca agcgcagcca gctggcgaca aggctgagtt catcgaaaaa     960
gttcgccgtg cactgtatct gggcaaaatc gtttcttacg ctcagggggtt ctctcaactg    1020 cgtgcggcgt ctgaagagta aactgggat ctgaactacg cgaaatcgc gaagattttc    1080 cgtgctggct gcatcatccg tgcgcagttc ctgcagaaaa tcaccgatgc ttatgccgaa    1140
aatccgcaga tcgctaacct gctgctggct ccttacttca gcaaattgc cgatgactac    1200 cagcaggcgc tgcgcgatgt cgtcgcttat gcggtacaga acggtatccc ggttccgacc    1260
ttcgccgctg cggttgccta ttatgacagc taccgcgccg ctgttctgcc tgcgaacctg    1320
atccaggcac agcgtgacta tttcggtgcg catacttata agcgcattga taagaaggt    1380 gtgttccata ccgaatggct ggattaa                                         1407

<210> SEQ ID NO 25

```
<211> LENGTH: 468
<212> TYPE: PRT
<213> ORGANISM: Escherichia coli

<400> SEQUENCE: 25

Met Ser Lys Gln Gln Ile Gly Val Val Met Ala Val Met Gly Arg
1               5                   10                  15

Asn Leu Ala Pro Asn Ile Glu Ser Arg Gly Tyr Thr Val Ser Ile Phe
                20                  25                  30

Asn Arg Ser Arg Glu Lys Thr Glu Glu Val Ile Ala Glu Asn Pro Gly
            35                  40                  45

Lys Lys Leu Val Pro Tyr Tyr Thr Val Lys Glu Phe Val Glu Ser Leu
50                  55                  60

Glu Thr Pro Arg Arg Ile Leu Leu Met Val Lys Ala Gly Ala Gly Thr
65                  70                  75                  80

Asp Ala Ala Ile Asp Ser Leu Lys Pro Tyr Leu Asp Lys Gly Asp Ile
                85                  90                  95

Ile Ile Asp Ser Gly Asn Thr Phe Phe Gln Asp Thr Ile Arg Arg Asn
            100                 105                 110

Arg Glu Leu Ser Ala Glu Gly Phe Asn Phe Ile Gly Thr Gly Val Ser
            115                 120                 125

Gly Gly Glu Glu Gly Ala Leu Lys Gly Pro Ser Ile Met Pro Gly Gly
130                 135                 140

Gln Lys Glu Ala Tyr Glu Leu Val Ala Pro Ile Leu Thr Lys Ile Ala
145                 150                 155                 160

Ala Val Ala Glu Asp Gly Glu Pro Cys Val Thr Tyr Ile Gly Ala Asp
                165                 170                 175

Gly Ala Gly His Tyr Val Lys Met Val His Asn Gly Ile Glu Tyr Gly
            180                 185                 190

Asp Met Gln Leu Ile Ala Glu Ala Tyr Ser Leu Leu Lys Gly Gly Leu
            195                 200                 205

Asn Leu Thr Asn Glu Glu Leu Ala Gln Ile Phe Thr Glu Trp Asn Asn
210                 215                 220

Gly Glu Leu Ser Ser Tyr Leu Ile Asp Ile Thr Lys Asp Ile Phe Thr
225                 230                 235                 240

Lys Lys Asp Glu Asp Gly Asn Tyr Leu Val Asp Val Ile Leu Asp Glu
                245                 250                 255

Ala Ala Asn Lys Gly Thr Gly Lys Trp Thr Ser Gln Ser Ala Leu Asp
            260                 265                 270

Leu Gly Glu Pro Leu Ser Leu Ile Thr Glu Ser Val Phe Ala Arg Tyr
            275                 280                 285

Ile Ser Ser Leu Lys Asp Gln Arg Val Ala Ala Ser Lys Val Leu Ser
290                 295                 300

Gly Pro Gln Ala Gln Pro Ala Gly Asp Lys Ala Glu Phe Ile Glu Lys
305                 310                 315                 320

Val Arg Arg Ala Leu Tyr Leu Gly Lys Ile Val Ser Tyr Ala Gln Gly
                325                 330                 335

Phe Ser Gln Leu Arg Ala Ala Ser Glu Glu Tyr Asn Trp Asp Leu Asn
            340                 345                 350

Tyr Gly Glu Ile Ala Lys Ile Phe Arg Ala Gly Cys Ile Ile Arg Ala
            355                 360                 365

Gln Phe Leu Gln Lys Ile Thr Asp Ala Tyr Ala Glu Asn Pro Gln Ile
370                 375                 380

Ala Asn Leu Leu Leu Ala Pro Tyr Phe Lys Gln Ile Ala Asp Asp Tyr
385                 390                 395                 400
```

Gln Gln Ala Leu Arg Asp Val Val Ala Tyr Ala Val Gln Asn Gly Ile
            405                 410                 415

Pro Val Pro Thr Phe Ala Ala Ala Val Ala Tyr Tyr Asp Ser Tyr Arg
        420                 425                 430

Ala Ala Val Leu Pro Ala Asn Leu Ile Gln Ala Gln Arg Asp Tyr Phe
            435                 440                 445

Gly Ala His Thr Tyr Lys Arg Ile Asp Lys Glu Gly Val Phe His Thr
        450                 455                 460

Glu Trp Leu Asp
465

<210> SEQ ID NO 26
<211> LENGTH: 1407
<212> TYPE: DNA
<213> ORGANISM: Escherichia coli

<400> SEQUENCE: 26

| | |
|---|---|
| atgtcaaagc aacagatcgg cgtagtcggt atggcagtga tggggcgcaa ccttgcgctc | 60 |
| aacatcgaaa gccgtggtta taccgtctct attttcaacc gttcccgtga aaagacggaa | 120 |
| gaagtgattg ccgaaaatcc aggcaagaaa ctggttcctt actatacggt gaaagaattt | 180 |
| gttgaatctc tggaaacgcc tcgtcgcatc ttgttaatgg tgaaagcagg tgcaggcacg | 240 |
| gatgctgcta ttgattccct taagccatac ctcgataaag gtgacatcat cattgatggt | 300 |
| ggtaataccc tcttccagga caccattcgt cgtaaccgtg agctttctgc agaaggcttt | 360 |
| aacttcatcg gtaccggtgt ttccggtggt gaggagggcg cactaaaagg tccttccatt | 420 |
| atgcctggtg ggcagaaaga agcctatgaa ctagttgcgc cgatcctgac caaaatcgcc | 480 |
| gcagtggctg aagacggtga gccatgcgtt acctatattg gtgccgatgg cgcaggtcac | 540 |
| tatgtgaaga tggttcacaa cggtattgaa tacggcgata tgcagctgat tgctgaagcc | 600 |
| tattctctgc ttaaaggtgg tctgaacctc accaacgaag aactggcgca gatctttacc | 660 |
| gagtggaata cggtgaact gagcagctac ctgatcgaca ttaccaaaga catcttcact | 720 |
| aaaaaagatg aagacggtaa ctacctggtt gatgtgatcc tggatgaggc ggcaaacaaa | 780 |
| ggtacgggca atggaccag ccagagcgca ctggatctcg cgaaccgct gtcgctgatt | 840 |
| accgagtctg tgtttgcacg atacatctct tctctgaaag atcagcgcgt tgctgcgtct | 900 |
| aaagttctct ctggcccaca agcgcagcca gctggcgaca aggctgagtt catcgaaaaa | 960 |
| gttcgccgtg cactgtatct gggcaaaatc gtttcttacg ctcagggtt ctctcaactg | 1020 |
| cgtgcggcgt ctgaagagta caactgggat ctgaactacg gcgaaatcgc gaagattttc | 1080 |
| cgtgctggct gcatcatccg tgcgcagttc ctgcagaaaa tcaccgatgc ttatgccgaa | 1140 |
| aatccgcaga tcgctaacct gctgctggct ccttacttca gcaaattgc cgatgactac | 1200 |
| cagcaggcgc tgcgcgatgt cgtcgcttat gcggtacaga acgtatccc ggttccgacc | 1260 |
| ttcgccgctg cggttgccta ttatgacagc taccgcgccg ctgttctgcc tgcgaacctg | 1320 |
| atccaggcac agcgtgacta tttcggtgcg catacttata gcgcgttga taagaaggt | 1380 |
| gtgttccata ccgaatggct ggattaa | 1407 |

<210> SEQ ID NO 27
<211> LENGTH: 468
<212> TYPE: PRT
<213> ORGANISM: Escherichia coli

<400> SEQUENCE: 27

-continued

```
Met Ser Lys Gln Gln Ile Gly Val Val Gly Met Ala Val Met Gly Arg
1               5                   10                  15

Asn Leu Ala Leu Asn Ile Glu Ser Arg Gly Tyr Thr Val Ser Ile Phe
            20                  25                  30

Asn Arg Ser Arg Glu Lys Thr Glu Glu Val Ile Ala Glu Asn Pro Gly
        35                  40                  45

Lys Lys Leu Val Pro Tyr Tyr Thr Val Lys Glu Phe Val Glu Ser Leu
50                      55                  60

Glu Thr Pro Arg Arg Ile Leu Leu Met Val Lys Ala Gly Ala Gly Thr
65                      70                  75                  80

Asp Ala Ala Ile Asp Ser Leu Lys Pro Tyr Leu Asp Lys Gly Asp Ile
                85                  90                  95

Ile Ile Asp Gly Gly Asn Thr Phe Phe Gln Asp Thr Ile Arg Arg Asn
            100                 105                 110

Arg Glu Leu Ser Ala Glu Gly Phe Asn Phe Ile Gly Thr Gly Val Ser
        115                 120                 125

Gly Gly Glu Glu Gly Ala Leu Lys Gly Pro Ser Ile Met Pro Gly Gly
    130                 135                 140

Gln Lys Glu Ala Tyr Glu Leu Val Ala Pro Ile Leu Thr Lys Ile Ala
145                 150                 155                 160

Ala Val Ala Glu Asp Gly Glu Pro Cys Val Thr Tyr Ile Gly Ala Asp
                165                 170                 175

Gly Ala Gly His Tyr Val Lys Met Val His Asn Gly Ile Glu Tyr Gly
            180                 185                 190

Asp Met Gln Leu Ile Ala Glu Ala Tyr Ser Leu Leu Lys Gly Gly Leu
        195                 200                 205

Asn Leu Thr Asn Glu Glu Leu Ala Gln Ile Phe Thr Glu Trp Asn Asn
    210                 215                 220

Gly Glu Leu Ser Ser Tyr Leu Ile Asp Ile Thr Lys Asp Ile Phe Thr
225                 230                 235                 240

Lys Lys Asp Glu Asp Gly Asn Tyr Leu Val Asp Val Ile Leu Asp Glu
                245                 250                 255

Ala Ala Asn Lys Gly Thr Gly Lys Trp Thr Ser Gln Ser Ala Leu Asp
            260                 265                 270

Leu Gly Glu Pro Leu Ser Leu Ile Thr Glu Ser Val Phe Ala Arg Tyr
        275                 280                 285

Ile Ser Ser Leu Lys Asp Gln Arg Val Ala Ala Ser Lys Val Leu Ser
    290                 295                 300

Gly Pro Gln Ala Gln Pro Ala Gly Asp Lys Ala Glu Phe Ile Glu Lys
305                 310                 315                 320

Val Arg Arg Ala Leu Tyr Leu Gly Lys Ile Val Ser Tyr Ala Gln Gly
                325                 330                 335

Phe Ser Gln Leu Arg Ala Ala Ser Glu Glu Tyr Asn Trp Asp Leu Asn
            340                 345                 350

Tyr Gly Glu Ile Ala Lys Ile Phe Arg Ala Gly Cys Ile Ile Arg Ala
        355                 360                 365

Gln Phe Leu Gln Lys Ile Thr Asp Ala Tyr Ala Glu Asn Pro Gln Ile
    370                 375                 380

Ala Asn Leu Leu Leu Ala Pro Tyr Phe Lys Gln Ile Ala Asp Asp Tyr
385                 390                 395                 400

Gln Gln Ala Leu Arg Asp Val Val Ala Tyr Ala Val Gln Asn Gly Ile
                405                 410                 415

Pro Val Pro Thr Phe Ala Ala Ala Val Ala Tyr Tyr Asp Ser Tyr Arg
            420                 425                 430
```

Ala Ala Val Leu Pro Ala Asn Leu Ile Gln Ala Gln Arg Asp Tyr Phe
        435                 440                 445

Gly Ala His Thr Tyr Lys Arg Val Asp Lys Glu Gly Val Phe His Thr
    450                 455                 460

Glu Trp Leu Asp
465

<210> SEQ ID NO 28
<211> LENGTH: 1407
<212> TYPE: DNA
<213> ORGANISM: Escherichia coli

<400> SEQUENCE: 28

```
atgtcaaagc aacagatcgg cgtagtcggt atggcagtga tggggcgcaa cctagcgctc      60
aacatcgaaa gccgtggtta ccgtctctct attttcaacc gccccgtga agaagacggaa     120
gaagtgattg ccgaaaatcc aggcaagaaa ctggttcctt actatacggt gaaagagttt     180
gttgaatctc tggaaacgcc tcgccgcatc ctgttaatgg tgaaagcagg tgcaggcacg     240
gatgctgcta ttgattccct caggccgtac ctcgataaag gtgacatcat cattgatggt     300
ggtaacacct tcttccagga caccattcgt cgtaaccgtg agctttctgc cgaaggcttt     360
aacttcatcg gtaccggtgt ttccggcgga gaagaaggcg cgctgaaagg tccttccatt     420
atgcctggtg ggcagaaaga agcctatgaa ctggttgcgc cgatcctgac caaaatcgcc     480
gcagtggctg aagacggtga gccatgcgtt acctatattg gtgccgatgg cgcaggtcac     540
tatgtgaaga tggttcacaa cggtattgaa acggagata tgcaactgat tgctgaagcc      600
tattctctgc ttaaaggtgg cctgaacctc accaacgaag aactggcgca gacgtttacc     660
gagtggaata cggtgaact gagcagctac ctgatcgaca tcaccaaaga tatcttcacc      720
aaaaagatg aagacggtaa ctacctggtt gatgtgatcc tggatgaagc ggctaacaaa     780
ggtaccggta atggaccag ccagagcgca ctggatctcg cgaaccgct gtcgctgatt      840
accgagtctg tgtttgcacg ttatatctct tctctgaaag atcagcgtgt tgccgcatct     900
aaagttctct ctggcccgca agcacagcca gcaggcgaca ggctgagtt catcgaaaaa     960
gttcgccgtg cgctgtatct gggcaaaatc gtttcttacg cccagggctt ctctcagctg    1020
cgtgctgcgt ctgaagagtt caactgggat ctgaactacg cgaaatcgc gaagattttc    1080
cgtgctggct gcatcattcg tgcgcagttc ctgcagaaaa ttaccgatgc ttatgccgaa    1140
aatccgcaga tcgctaacct gctgctggct ccgtacttca gcaaattgc cgatgattac    1200
cagcaggcgc tgcgtgatgt cgttgcttat gcggtacaga acggtatccc ggttccgacc    1260
ttcgccgctg cggttgccta ttacgatagc taccgtgccg ctgttctgcc tgcgaacctg    1320
atccaggcac agcgtgacta tttcggtgca catacttata gcgcattga taagaaggt     1380
gtgttccata ctgaatggct ggattaa                                        1407
```

<210> SEQ ID NO 29
<211> LENGTH: 468
<212> TYPE: PRT
<213> ORGANISM: Escherichia coli

<400> SEQUENCE: 29

Met Ser Lys Gln Gln Ile Gly Val Val Gly Met Ala Val Met Gly Arg
1               5                   10                  15

Asn Leu Ala Leu Asn Ile Glu Ser Arg Gly Tyr Thr Val Ser Ile Phe
            20                  25                  30

```
Asn Arg Pro Arg Glu Lys Thr Glu Val Ile Ala Glu Asn Pro Gly
     35                  40                  45

Lys Lys Leu Val Pro Tyr Tyr Thr Val Lys Glu Phe Val Glu Ser Leu
50                  55                  60

Glu Thr Pro Arg Arg Ile Leu Leu Met Val Lys Ala Gly Ala Gly Thr
65                  70                  75                  80

Asp Ala Ala Ile Asp Ser Leu Arg Pro Tyr Leu Asp Lys Gly Asp Ile
                 85                  90                  95

Ile Ile Asp Gly Gly Asn Thr Phe Phe Gln Asp Thr Ile Arg Arg Asn
             100                 105                 110

Arg Glu Leu Ser Ala Glu Gly Phe Asn Phe Ile Gly Thr Gly Val Ser
         115                 120                 125

Gly Gly Glu Glu Gly Ala Leu Lys Gly Pro Ser Ile Met Pro Gly Gly
130                 135                 140

Gln Lys Glu Ala Tyr Glu Leu Val Ala Pro Ile Leu Thr Lys Ile Ala
145                 150                 155                 160

Ala Val Ala Glu Asp Gly Glu Pro Cys Val Thr Tyr Ile Gly Ala Asp
                 165                 170                 175

Gly Ala Gly His Tyr Val Lys Met Val His Asn Gly Ile Glu Tyr Gly
             180                 185                 190

Asp Met Gln Leu Ile Ala Glu Ala Tyr Ser Leu Leu Lys Gly Gly Leu
         195                 200                 205

Asn Leu Thr Asn Glu Glu Leu Ala Gln Thr Phe Thr Glu Trp Asn Asn
210                 215                 220

Gly Glu Leu Ser Ser Tyr Leu Ile Asp Ile Thr Lys Asp Ile Phe Thr
225                 230                 235                 240

Lys Lys Asp Glu Asp Gly Asn Tyr Leu Val Asp Val Ile Leu Asp Glu
                 245                 250                 255

Ala Ala Asn Lys Gly Thr Gly Lys Trp Thr Ser Gln Ser Ala Leu Asp
             260                 265                 270

Leu Gly Glu Pro Leu Ser Leu Ile Thr Glu Ser Val Phe Ala Arg Tyr
         275                 280                 285

Ile Ser Ser Leu Lys Asp Gln Arg Val Ala Ala Ser Lys Val Leu Ser
290                 295                 300

Gly Pro Gln Ala Gln Pro Ala Gly Asp Lys Ala Glu Phe Ile Glu Lys
305                 310                 315                 320

Val Arg Arg Ala Leu Tyr Leu Gly Lys Ile Val Ser Tyr Ala Gln Gly
                 325                 330                 335

Phe Ser Gln Leu Arg Ala Ala Ser Glu Glu Phe Asn Trp Asp Leu Asn
             340                 345                 350

Tyr Gly Glu Ile Ala Lys Ile Phe Arg Ala Gly Cys Ile Ile Arg Ala
         355                 360                 365

Gln Phe Leu Gln Lys Ile Thr Asp Ala Tyr Ala Glu Asn Pro Gln Ile
370                 375                 380

Ala Asn Leu Leu Leu Ala Pro Tyr Phe Lys Gln Ile Ala Asp Asp Tyr
385                 390                 395                 400

Gln Gln Ala Leu Arg Asp Val Val Ala Tyr Ala Val Gln Asn Gly Ile
                 405                 410                 415

Pro Val Pro Thr Phe Ala Ala Val Ala Tyr Tyr Asp Ser Tyr Arg
             420                 425                 430

Ala Ala Val Leu Pro Ala Asn Leu Ile Gln Ala Gln Arg Asp Tyr Phe
         435                 440                 445

Gly Ala His Thr Tyr Lys Arg Ile Asp Lys Glu Gly Val Phe His Thr
450                 455                 460
```

Glu Trp Leu Asp
465

<210> SEQ ID NO 30
<211> LENGTH: 1407
<212> TYPE: DNA
<213> ORGANISM: Escherichia coli

<400> SEQUENCE: 30

| | | |
|---|---|---|
| atgtcaaagc aacagatcgg cgtagtcggt atggcagtga tggggcgcaa cctagcgctc | 60 |
| aacatcgaaa gccgtggtta taccgtctct attttcaacc gctcccgtga aagacggaa | 120 |
| gaagtgattg ccgaaaatcc aggcaagaaa ctggttcctt actatacggt gaaagagttt | 180 |
| gttgaatctc tggaaacgcc tcgccgcatc ctgttaatgg tgaaagcagg tgcaggcacg | 240 |
| gatgctgcta ttgattccct caagccgtac ctcgataaag gtgacatcat tattgatggt | 300 |
| ggtaacacct tcttccagga caccattcgt cgtaaccgtg agctttctgc cgaaggcttt | 360 |
| aacttcatcg gtaccggtgt ttccggcgga gaagaaggcg cgctgaaagg tccttccatt | 420 |
| atgcctggtg gcagaaaga agcctatgaa ctggttgcgc cgatcctgac caaaatcgcc | 480 |
| gcagtggctg aagacggtga gccatgcgtt acctatattg gtgccgatgg cgcaggtcac | 540 |
| tatgtgaaga tggttcacaa cggtattgaa tacggagata tgcaactgat tgctgaagcc | 600 |
| tattctctgc ttaaaggtgg cctgaacctc accaacgaag aactggcgca gacgtttacc | 660 |
| gagtggaata cggtgaact gagcagctac ctgatcgaca tcaccaaaga tatcttcacc | 720 |
| aaaaaagatg aagacggtaa ctacctggtt gatgtgatcc tggatgaagc ggctaacaaa | 780 |
| ggtaccggta atggaccag ccagagcgca ctggatctcg cgaaccgct gtcgctgatt | 840 |
| accgagtctg tgtttgcacg ttatatctct tctctgaaag atcagcgtgt tgccgcatct | 900 |
| aaagttctct ctggcccgca agcacagcca gcaggcgaca aggctgagtt catcgaaaaa | 960 |
| gttcgccgtg cgctgtatct gggcaaaatc gtttcttacg cccagggctt ctctcagctg | 1020 |
| cgtgctgcgt ctgaagagta caactggat ctgaactacg gcgaaatcgc gaagatttc | 1080 |
| cgtgctggct gcatcattcg tgcgcagttc ctgcagaaaa ttaccgatgc ttatgccgaa | 1140 |
| aatccgcaga tcgctaacct gctgctggct ccgtacttca gcaaattgc gatgattac | 1200 |
| cagcaggcgc tgcgtgatgt cgttgcttat gcggtacaga acggtatccc ggttccgacc | 1260 |
| ttcgccgctg cggttgccta ttacgatagc taccgtgccg ctgttctgcc tgcgaacctg | 1320 |
| atccaggcac agcgtgacta tttcggtgca catacttata agcgcattga taaagaaggt | 1380 |
| gtgttccata ctgaatggct ggattaa | 1407 |

<210> SEQ ID NO 31
<211> LENGTH: 468
<212> TYPE: PRT
<213> ORGANISM: Escherichia coli

<400> SEQUENCE: 31

Met Ser Lys Gln Gln Ile Gly Val Val Gly Met Ala Val Met Gly Arg
1               5                   10                  15

Asn Leu Ala Leu Asn Ile Glu Ser Arg Gly Tyr Thr Val Ser Ile Phe
            20                  25                  30

Asn Arg Ser Arg Glu Lys Thr Glu Glu Val Ile Ala Glu Asn Pro Gly
        35                  40                  45

Lys Lys Leu Val Pro Tyr Tyr Thr Val Lys Glu Phe Val Glu Ser Leu
    50                  55                  60

Glu Thr Pro Arg Arg Ile Leu Leu Met Val Lys Ala Gly Ala Gly Thr
 65                  70                  75                  80

Asp Ala Ala Ile Asp Ser Leu Lys Pro Tyr Leu Asp Lys Gly Asp Ile
                 85                  90                  95

Ile Ile Asp Gly Gly Asn Thr Phe Phe Gln Asp Thr Ile Arg Arg Asn
            100                 105                 110

Arg Glu Leu Ser Ala Glu Gly Phe Asn Phe Ile Gly Thr Gly Val Ser
        115                 120                 125

Gly Gly Glu Glu Gly Ala Leu Lys Gly Pro Ser Ile Met Pro Gly Gly
    130                 135                 140

Gln Lys Glu Ala Tyr Glu Leu Val Ala Pro Ile Leu Thr Lys Ile Ala
145                 150                 155                 160

Ala Val Ala Glu Asp Gly Glu Pro Cys Val Thr Tyr Ile Gly Ala Asp
                165                 170                 175

Gly Ala Gly His Tyr Val Lys Met Val His Asn Gly Ile Glu Tyr Gly
            180                 185                 190

Asp Met Gln Leu Ile Ala Glu Ala Tyr Ser Leu Leu Lys Gly Gly Leu
        195                 200                 205

Asn Leu Thr Asn Glu Gly Leu Ala Gln Thr Phe Thr Glu Trp Asn Asn
    210                 215                 220

Gly Glu Leu Ser Ser Tyr Leu Ile Asp Ile Thr Lys Asp Ile Phe Thr
225                 230                 235                 240

Lys Lys Asp Glu Asp Gly Asn Tyr Leu Val Asp Val Ile Leu Asp Glu
                245                 250                 255

Ala Ala Asn Lys Gly Thr Gly Lys Trp Thr Ser Gln Ser Ala Leu Asp
            260                 265                 270

Leu Gly Glu Pro Leu Ser Leu Ile Thr Glu Ser Val Phe Ala Arg Tyr
        275                 280                 285

Ile Ser Ser Leu Lys Asp Gln Arg Val Ala Ala Ser Lys Val Leu Ser
    290                 295                 300

Gly Pro Gln Ala Gln Pro Ala Gly Asp Lys Ala Glu Phe Ile Glu Lys
305                 310                 315                 320

Val Arg Arg Ala Leu Tyr Leu Gly Lys Ile Val Ser Tyr Ala Gln Gly
                325                 330                 335

Phe Ser Gln Leu Arg Ala Ala Ser Glu Glu Tyr Asn Trp Asp Leu Asn
            340                 345                 350

Tyr Gly Glu Ile Ala Lys Ile Phe Arg Ala Gly Cys Ile Ile Arg Ala
        355                 360                 365

Gln Phe Leu Gln Lys Ile Thr Asp Ala Tyr Ala Glu Asn Pro Gln Ile
    370                 375                 380

Ala Asn Leu Leu Leu Ala Pro Tyr Phe Lys Gln Ile Ala Asp Asp Tyr
385                 390                 395                 400

Gln Gln Ala Leu Arg Asp Val Val Ala Tyr Ala Val Gln Asn Gly Ile
                405                 410                 415

Pro Val Pro Thr Phe Ala Ala Ala Val Ala Tyr Tyr Asp Ser Tyr Arg
            420                 425                 430

Ala Ala Val Leu Pro Ala Asn Leu Ile Gln Ala Gln Arg Asp Tyr Phe
        435                 440                 445

Gly Ala His Thr Tyr Lys Arg Ile Asp Lys Glu Gly Val Phe His Thr
    450                 455                 460

Glu Trp Leu Asp
465

<210> SEQ ID NO 32

<211> LENGTH: 1407
<212> TYPE: DNA
<213> ORGANISM: Escherichia coli

<400> SEQUENCE: 32

```
atgtcaaagc aacagatcgg cgtcgtcggt atggctgtga tgggacgcaa tcttgcgctc      60
aacatcgaaa gccgtggtta taccgtctct attttcaacc gttcccgtga aaaaacggaa     120
gaagtgattg ccgaaaatcc aggcaagaaa ctggttcctt actatacggt gaaagagttt     180
gttgaatctc tggaaacgcc tcgtcgcatc ctgttaatgg tgaaagcagg tgcaggcacg     240
gatgctgcta ttgattccct caagccttac ctcgataaag gtgacatcat cattgatggt     300
ggtaacaccct tcttcctgga caccattcgt cgtaaccgtg agctttctgc agaaggcttt     360
aacttcattg gtaccggtgt ttccggcggt aagggggggg cgctgaaagg ccttccatc      420
atgcctggtg ggcagaaaga agcctatgaa ctggttgctc cgatcttgac caaaatcgcc     480
gccgttgctg aagacggcga accgtgtgtt acctatattg gtgccgatgg cgcgggtcac     540
tatgtggaga tggttcacaa tggtattgaa tacggtgata tgcaactgat tgctgaagcc     600
tattctctgc ttaaaggcgg cctgaatctc tctaacgaag aactggcaca gacctttacc     660
gagtggaata acggtgaact gagcagctac ctgatcgaca tcaccaaaga tatcttcacc     720
aaaaaagatg aagacggtaa ctacctggtt gatgtgattc tggatgaagc ggctaacaag     780
ggtaccggta atggaccag ccagagcgcg ctggatctcg gcgaaccgct gtcactgatt      840
accgagtctg tgtttgcacg ttatatctct tctctgaaag atcagcgcgt tgccgcgtct     900
aaagttctca ctggcccgaa agcgcagcca gcaggcgata ggctgagtt tatcgagaaa      960
gttcgtcgtg cgctgtatct gggcaaaatc gtttcttacg ctcagggctt ctctcagctg    1020
cgtgcggcgt ctgaagagta caactgggat ctgaactacg gcgaaatcgc gaagattttc    1080
cgtgctggct gcatcatccg tgcgcagttc ctgcagaaaa tcaccgatgc atatgccgaa    1140
aatccgcaga tcgctaacct gctgctggct ccgtacttca gcaaattgc cgatgactac     1200
cagcaggcgc tgcgtgatgt cgttgcttat gcagtacaga acggtatccc ggttccgacc    1260
ttcgcggctg cggttgccta ttatgacagc taccgcgccg cagttctgcc tgcaaacctg    1320
atccaggcac agcgtgacta tttcggtgcg catacttata gcgcattga taaagaaggt     1380
gtgttccata ctgaatggct ggattaa                                         1407
```

<210> SEQ ID NO 33
<211> LENGTH: 468
<212> TYPE: PRT
<213> ORGANISM: Escherichia coli

<400> SEQUENCE: 33

```
Met Ser Lys Gln Gln Ile Gly Val Val Gly Met Ala Val Met Gly Arg
1               5                   10                  15

Asn Leu Ala Leu Asn Ile Glu Ser Arg Gly Tyr Thr Val Ser Ile Phe
            20                  25                  30

Asn Arg Ser Arg Glu Lys Thr Glu Glu Val Ile Ala Glu Asn Pro Gly
        35                  40                  45

Lys Lys Leu Val Pro Tyr Tyr Thr Val Lys Glu Phe Val Glu Ser Leu
    50                  55                  60

Glu Thr Pro Arg Arg Ile Leu Leu Met Val Lys Ala Gly Ala Gly Thr
65                  70                  75                  80

Asp Ala Ala Ile Asp Ser Leu Lys Pro Tyr Leu Asp Lys Gly Asp Ile
                85                  90                  95
```

Ile Ile Asp Gly Gly Asn Thr Phe Phe Leu Asp Thr Ile Arg Arg Asn
            100                 105                 110

Arg Glu Leu Ser Ala Glu Gly Phe Asn Phe Ile Gly Thr Gly Val Ser
        115                 120                 125

Gly Gly Glu Gly Ala Leu Lys Gly Pro Ser Ile Met Pro Gly Gly
130                 135                 140

Gln Lys Glu Ala Tyr Glu Leu Val Ala Pro Ile Leu Thr Lys Ile Ala
145                 150                 155                 160

Ala Val Ala Glu Asp Gly Glu Pro Cys Val Thr Tyr Ile Gly Ala Asp
                165                 170                 175

Gly Ala Gly His Tyr Val Glu Met Val His Asn Gly Ile Glu Tyr Gly
            180                 185                 190

Asp Met Gln Leu Ile Ala Glu Ala Tyr Ser Leu Leu Lys Gly Gly Leu
            195                 200                 205

Asn Leu Ser Asn Glu Glu Leu Ala Gln Thr Phe Thr Glu Trp Asn Asn
210                 215                 220

Gly Glu Leu Ser Ser Tyr Leu Ile Asp Ile Thr Lys Asp Ile Phe Thr
225                 230                 235                 240

Lys Lys Asp Glu Asp Gly Asn Tyr Leu Val Asp Val Ile Leu Asp Glu
                245                 250                 255

Ala Ala Asn Lys Gly Thr Gly Lys Trp Thr Ser Gln Ser Ala Leu Asp
                260                 265                 270

Leu Gly Glu Pro Leu Ser Leu Ile Thr Glu Ser Val Phe Ala Arg Tyr
            275                 280                 285

Ile Ser Ser Leu Lys Asp Gln Arg Val Ala Ala Ser Lys Val Leu Thr
            290                 295                 300

Gly Pro Lys Ala Gln Pro Ala Gly Asp Lys Ala Glu Phe Ile Glu Lys
305                 310                 315                 320

Val Arg Arg Ala Leu Tyr Leu Gly Lys Ile Val Ser Tyr Ala Gln Gly
                325                 330                 335

Phe Ser Gln Leu Arg Ala Ala Ser Glu Glu Tyr Asn Trp Asp Leu Asn
            340                 345                 350

Tyr Gly Glu Ile Ala Lys Ile Phe Arg Ala Gly Cys Ile Ile Arg Ala
            355                 360                 365

Gln Phe Leu Gln Lys Ile Thr Asp Ala Tyr Ala Glu Asn Pro Gln Ile
370                 375                 380

Ala Asn Leu Leu Leu Ala Pro Tyr Phe Lys Gln Ile Ala Asp Asp Tyr
385                 390                 395                 400

Gln Gln Ala Leu Arg Asp Val Val Ala Tyr Ala Val Gln Asn Gly Ile
                405                 410                 415

Pro Val Pro Thr Phe Ala Ala Val Ala Tyr Tyr Asp Ser Tyr Arg
            420                 425                 430

Ala Ala Val Leu Pro Ala Asn Leu Ile Gln Ala Gln Arg Asp Tyr Phe
            435                 440                 445

Gly Ala His Thr Tyr Lys Arg Ile Asp Lys Glu Gly Val Phe His Thr
            450                 455                 460

Glu Trp Leu Asp
465

<210> SEQ ID NO 34
<211> LENGTH: 1407
<212> TYPE: DNA
<213> ORGANISM: Escherichia coli

<400> SEQUENCE: 34

-continued

```
atgtcaaagc aacagatcgg cgtcgtcggt atggctgtga tgggacgcaa tcttgcgctc    60
aacatcgaaa gccgtggtta taccgtctct attttcaacc gttcccgtga aaaaacggaa   120
gaagtgattg ccgaaaatcc aggcaagaaa ctggttcctt actatacggt gaaagagttt   180
gttgaatctc tggaaacgcc tcgtcgcatc ctgttaatgg tgaaagcagg tgcaggcacg   240
gatgctgcta ttgattccct caagccttac ctcgataaag gtgacatcat cattgatggt   300
ggtaacacct tcttcctgga caccattcgt cgtaaccgtg agctttctgc agaaggcttt   360
aacttcattg gtaccggtgt tccggcggt gaagagggg cgctgaaagg ccttccatc     420
atgcctggtg gcagaaaga agcctatgaa ctggttgctc cgatcttgac aaaatcgcc    480
gccgttgctg aagacggcga accgtgtgtt acctatattg gtgccgatgg cgcgggtcac   540
tatgtgaaga tggttcacaa tggtattgaa tacggtgata tgcaactgat tgctgaagcc   600
tattctctgc ttaaaggcgg cctgaatctc tctaacgaag aactggcaca gacctttacc   660
gagtggaata cggtgaact gagcagctac ctgatcgaca tcaccaaaga tatcttcacc    720
aaaaaagatg aagacggtaa ctacctggtt gatgtgattc tggatgaggc ggctaacaag   780
ggtaccggta atggaccag ccagagcgcg ctggatctcg cgaaccgct gtcactgatt     840
accgagtctg tgtttgcacg ttatatctct tctctgaaag atcagcgcgt tgccgcgtct   900
aaagttctca ctggcccgaa agcgcagcca gcaggcgata aggctgagtt tatcgagaaa   960
gttcgtcgtg cgctgtatct gggcaaaatc gtttcttacg ctcagggctt ctctcagctg  1020
cgtgcggcgt ctgaagagta caactgggat ctgaactacg cgaaatcgc gaagattttc   1080
cgtgctggct gcatcatccg tgcgcagttc ctgcagaaaa tcaccgatgc atatgccgaa   1140
aatccgcaga tcgctaacct gctgctggct ccgtacttca gcaaattgc cgatgactac   1200
cagcaggcgc tgcgtgatgt cgttgcttat gcagtacaga acggtatccc ggttccgacc   1260
ttcgcggctg cggttgccta ttatgacagc taccgcgccg cagttctgcc tgcaaacctg  1320
atccaggcac agcgtgacta tttcggtgcg catacttata agcgcattga taaagaaggt  1380
gtgttccata ctgaatggct ggattaa                                      1407
```

<210> SEQ ID NO 35
<211> LENGTH: 468
<212> TYPE: PRT
<213> ORGANISM: Escherichia coli

<400> SEQUENCE: 35

```
Met Ser Lys Gln Gln Ile Gly Val Val Gly Met Ala Val Met Gly Arg
1               5                   10                  15

Asn Leu Ala Leu Asn Ile Glu Ser Arg Gly Tyr Thr Val Ser Ile Phe
            20                  25                  30

Asn Arg Ser Arg Glu Lys Thr Glu Glu Val Ile Ala Glu Asn Pro Gly
        35                  40                  45

Lys Lys Leu Val Pro Tyr Tyr Thr Val Lys Glu Phe Val Glu Ser Leu
    50                  55                  60

Glu Thr Pro Arg Arg Ile Leu Leu Met Val Lys Ala Gly Ala Gly Thr
65                  70                  75                  80

Asp Ala Ala Ile Asp Ser Leu Lys Pro Tyr Leu Asp Lys Gly Asp Ile
                85                  90                  95

Ile Ile Asp Gly Gly Asn Thr Phe Phe Leu Asp Thr Ile Arg Arg Asn
            100                 105                 110

Arg Glu Leu Ser Ala Glu Gly Phe Asn Phe Ile Gly Thr Gly Val Ser
        115                 120                 125
```

```
Gly Gly Glu Glu Gly Ala Leu Lys Gly Pro Ser Ile Met Pro Gly Gly
            130                 135                 140

Gln Lys Glu Ala Tyr Glu Leu Val Ala Pro Ile Leu Thr Lys Ile Ala
145                 150                 155                 160

Ala Val Ala Glu Asp Gly Glu Pro Cys Val Thr Tyr Ile Gly Ala Asp
                165                 170                 175

Gly Ala Gly His Tyr Val Lys Met Val His Asn Gly Ile Glu Tyr Gly
                180                 185                 190

Asp Met Gln Leu Ile Ala Glu Ala Tyr Ser Leu Leu Lys Gly Gly Leu
                195                 200                 205

Asn Leu Ser Asn Glu Glu Leu Ala Gln Thr Phe Thr Glu Trp Asn Asn
            210                 215                 220

Gly Glu Leu Ser Ser Tyr Leu Ile Asp Ile Thr Lys Asp Ile Phe Thr
225                 230                 235                 240

Lys Lys Asp Glu Asp Gly Asn Tyr Leu Val Asp Val Ile Leu Asp Glu
                245                 250                 255

Ala Ala Asn Lys Gly Thr Gly Lys Trp Thr Ser Gln Ser Ala Leu Asp
                260                 265                 270

Leu Gly Glu Pro Leu Ser Leu Ile Thr Glu Ser Val Phe Ala Arg Tyr
            275                 280                 285

Ile Ser Ser Leu Lys Asp Gln Arg Val Ala Ala Ser Lys Val Leu Thr
290                 295                 300

Gly Pro Lys Ala Gln Pro Ala Gly Asp Lys Ala Glu Phe Ile Glu Lys
305                 310                 315                 320

Val Arg Arg Ala Leu Tyr Leu Gly Lys Ile Val Ser Tyr Ala Gln Gly
                325                 330                 335

Phe Ser Gln Leu Arg Ala Ala Ser Glu Glu Tyr Asn Trp Asp Leu Asn
            340                 345                 350

Tyr Gly Glu Ile Ala Lys Ile Phe Arg Ala Gly Cys Ile Ile Arg Ala
            355                 360                 365

Gln Phe Leu Gln Lys Ile Thr Asp Ala Tyr Ala Glu Asn Pro Gln Ile
            370                 375                 380

Ala Asn Leu Leu Leu Ala Pro Tyr Phe Lys Gln Ile Ala Asp Asp Tyr
385                 390                 395                 400

Gln Gln Ala Leu Arg Asp Val Val Ala Tyr Ala Val Gln Asn Gly Ile
                405                 410                 415

Pro Val Pro Thr Phe Ala Ala Ala Val Ala Tyr Tyr Asp Ser Tyr Arg
                420                 425                 430

Ala Ala Val Leu Pro Ala Asn Leu Ile Gln Ala Gln Arg Asp Tyr Phe
            435                 440                 445

Gly Ala His Thr Tyr Lys Arg Ile Asp Lys Glu Gly Val Phe His Thr
            450                 455                 460

Glu Trp Leu Asp
465

<210> SEQ ID NO 36
<211> LENGTH: 1407
<212> TYPE: DNA
<213> ORGANISM: Escherichia coli

<400> SEQUENCE: 36
atgtcaaagc aacagatcgg cgtagtcggt atggcagtga tggggcgcaa cctagcgctc      60
aacatcgaaa gccgtggtta taccgtctct attttcaacc gctcccgtga agacggaa       120 gaagtgattg ccgaaaatcc aggcaagaaa ctggttcctt actatacggt gaaagagttt     180
```

-continued

```
gttgaatctc tggaaacgcc tcgtcgcatc ctgttaatgg tgaaagcagg tgcaggcacg    240
gatgctgcta ttgattccct caagccgtac ctcgataaag gtgacatcat cattgatggt    300
ggtaacacct tcttccagga caccattcgt cgtaaccgtg agctttctgc cgaaggcttt    360
aacttcatcg gtaccggtgt tccggcggga aagaaggcg cgctgaaagg tccttccatt    420
atgcctggtg gcagaaaga agcctatgaa ctggttgcgc cgatcctgac caaaatcgcc    480
gcagtggctg aagacggtga gccatgcgtt acctatattg gtgccgatgg cgcaggtcac    540
tatgtgaaga tggttcacaa cggtattgaa tacggagata tgcaactgat tgctgaagcc    600
tattctctgc ttaaaggtgg cctgaacctc accaacgaag aactggcgca acgtttacc     660
gagtggaata acggtgaact gagcagctac ctgatcgaca tcaccaaaga tatcttcacc    720
aaaaaagatg aagacggtaa ctacctggtt gatgtgatcc tggatgaagc ggctaacaaa    780
ggtaccggta atggaccag ccagagcgca ctggatctcg gcgaaccgct gtcgctgatt     840
accgagtctg tgtttgcacg ttatatctct tctctgaaag atcagcgtgt tgccgcatct    900
aaagttctct ctggcccgca agcacagcca gcaggcgaca aggctgagtt catcgaaaaa    960
gttcgccgtg cgctgtatct gggcaaaatc gtttcttacg cccagggctt ctctcagctg    1020
cgtgctgcgt ctgaagagta caactgggat ctgaactacg cgaaatcgc gaagattttc    1080
cgtgctggct gcatcattcg tgcgcagttc ctgcagaaaa ttaccgatgc ttatgccgaa    1140
aatccgcaga tcgctaacct gctgctggct ccgtacttca gcaaattgc cgatgattac    1200
cagcaggcgc tgcgtgatgt cgttgcttat gcggtacaga acggtatccc ggttccgacc    1260
ttcgccgctg cggttgccta ttacgatagc taccgtgccg ctgttctgcc tgcgaacctg    1320
atccaggcac agcgtgacta tttcggtgca catacttata agcgcattga taaagaaggt    1380
gtgttccata ctgaatggct ggattaa                                         1407
```

<210> SEQ ID NO 37
<211> LENGTH: 468
<212> TYPE: PRT
<213> ORGANISM: Escherichia coli

<400> SEQUENCE: 37

```
Met Ser Lys Gln Gln Ile Gly Val Val Gly Met Ala Val Met Gly Arg
1               5                   10                  15

Asn Leu Ala Leu Asn Ile Glu Ser Arg Gly Tyr Thr Val Ser Ile Phe
            20                  25                  30

Asn Arg Ser Arg Glu Lys Thr Glu Glu Val Ile Ala Glu Asn Pro Gly
        35                  40                  45

Lys Lys Leu Val Pro Tyr Tyr Thr Val Lys Glu Phe Val Glu Ser Leu
    50                  55                  60

Glu Thr Pro Arg Arg Ile Leu Leu Met Val Lys Ala Gly Ala Gly Thr
65                  70                  75                  80

Asp Ala Ala Ile Asp Ser Leu Lys Pro Tyr Leu Asp Lys Gly Asp Ile
                85                  90                  95

Ile Ile Asp Gly Gly Asn Thr Phe Phe Gln Asp Thr Ile Arg Arg Asn
            100                 105                 110

Arg Glu Leu Ser Ala Glu Gly Phe Asn Phe Ile Gly Thr Gly Val Ser
        115                 120                 125

Gly Gly Glu Glu Gly Ala Leu Lys Gly Pro Ser Ile Met Pro Gly Gly
    130                 135                 140

Gln Lys Glu Ala Tyr Glu Leu Val Ala Pro Ile Leu Thr Lys Ile Ala
145                 150                 155                 160
```

```
Ala Val Ala Glu Asp Gly Glu Pro Cys Val Thr Tyr Ile Gly Ala Asp
            165                 170                 175
Gly Ala Gly His Tyr Val Lys Met Val His Asn Gly Ile Glu Tyr Gly
        180                 185                 190
Asp Met Gln Leu Ile Ala Glu Ala Tyr Ser Leu Leu Lys Gly Gly Leu
    195                 200                 205
Asn Leu Thr Asn Glu Glu Leu Ala Gln Thr Phe Thr Glu Trp Asn Asn
210                 215                 220
Gly Glu Leu Ser Ser Tyr Leu Ile Asp Ile Thr Lys Asp Ile Phe Thr
225                 230                 235                 240
Lys Lys Asp Glu Asp Gly Asn Tyr Leu Val Asp Val Ile Leu Asp Glu
            245                 250                 255
Ala Ala Asn Lys Gly Thr Gly Lys Trp Thr Ser Gln Ser Ala Leu Asp
        260                 265                 270
Leu Gly Glu Pro Leu Ser Leu Ile Thr Glu Ser Val Phe Ala Arg Tyr
    275                 280                 285
Ile Ser Ser Leu Lys Asp Gln Arg Val Ala Ala Ser Lys Val Leu Ser
290                 295                 300
Gly Pro Gln Ala Gln Pro Ala Gly Asp Lys Ala Glu Phe Ile Glu Lys
305                 310                 315                 320
Val Arg Arg Ala Leu Tyr Leu Gly Lys Ile Val Ser Tyr Ala Gln Gly
            325                 330                 335
Phe Ser Gln Leu Arg Ala Ala Ser Glu Glu Tyr Asn Trp Asp Leu Asn
        340                 345                 350
Tyr Gly Glu Ile Ala Lys Ile Phe Arg Ala Gly Cys Ile Ile Arg Ala
    355                 360                 365
Gln Phe Leu Gln Lys Ile Thr Asp Ala Tyr Ala Glu Asn Pro Gln Ile
370                 375                 380
Ala Asn Leu Leu Leu Ala Pro Tyr Phe Lys Gln Ile Ala Asp Asp Tyr
385                 390                 395                 400
Gln Gln Ala Leu Arg Asp Val Val Ala Tyr Ala Val Gln Asn Gly Ile
            405                 410                 415
Pro Val Pro Thr Phe Ala Ala Val Ala Tyr Asp Ser Tyr Arg
        420                 425                 430
Ala Ala Val Leu Pro Ala Asn Leu Ile Gln Ala Gln Arg Asp Tyr Phe
    435                 440                 445
Gly Ala His Thr Tyr Lys Arg Ile Asp Lys Glu Gly Val Phe His Thr
450                 455                 460
Glu Trp Leu Asp
465

<210> SEQ ID NO 38
<211> LENGTH: 1407
<212> TYPE: DNA
<213> ORGANISM: Escherichia coli

<400> SEQUENCE: 38
atgtcaaagc aacagatcgg cgtagtcggt atggcagtga tggggcgcaa cctagcgctc      60
aacatcgaaa gccgtggtta taccgtctct atttcaacc gctcccgtga agacggaa       120 gaagtgattg ccgaaaatcc aggcaagaaa ctggttcctt actatacggt gaaagagttt     180
gttgaatctc tggaaacgcc tcgtcgcatc ctgttaatgg tgaaagcagg tgcaggcacg     240
gatgctgcta ttgattccct caagccgtac ctcgataaag gtgacatcat cattgatggt     300
ggtaacacct tcttccagga caccattcgt cgtaaccgtg agctttctgc cgaaggcttt     360
```

-continued

```
aacttcatcg gtaccggtgt tccggcgga agaaggcg cgctgaaagg tccttccatt      420
atgcctggtg gcagaaaga agcctatgaa ctggttgcgc cgatcctgac caaaatcgcc    480
gcagtggctg aagacggtga gccatgcgtt acctatattg gtgccgatgg cgcaggtcac   540
tatgtgaaga tggttcacaa cggtattgaa tacggagata tgcaactgat tgctgaagcc   600
tattctctgc ttaaaggtgg cctgaacctc accaacgaag aactggcgca gacgtttacc   660
gagtggaata cggtgaact gagcagctac ctgatcgaca tcaccaaaga tatcttcacc    720
aaaaaagatg aagacggtaa ctacctggtt gatgtgatcc tggatgaagc ggctaacaaa   780
ggtaccggta atggaccag ccagagcgca ctggatctcg cgaaccgct gtcgctgatt     840
accgagtctg tgtttgcacg ttatatctct tctctgaaag atcagcgtgt tgccgcatct   900
aaagttctct ctggcccgca agcacagcca gcaggcgaca aggctgagtt catcgaaaaa   960
gttcgccgtg cgctgtatct gggcaaaatc gtttcttacg cccagggctt ctctcagctg  1020
cgtgctgcgt ctgaagagta caactgggat ctgaactacg cgaaatcgc gaagattttc   1080
cgtgctggct gcatcattcg tgcgcagttc ctgcagaaaa ttaccgatgc ttatgccgaa   1140
aatccgcaga tcgctaacct gctgctggct ccgtacttca gcaaattgc cgatgattac   1200
cagcaggcgc tgcgtgatgt cgttgcttat gcggtacaga acggtatccc ggttccgacc  1260
ttcgccgctg cggttgccta ttacgatagc taccgtgccg ctgttctgcc tgcgaacctg  1320
atccaggcac agcgtgacta tttcggtgca catacttata agcgcattga taaagaaggt  1380
gtgttccata ctgaatggct ggattaa                                      1407
```

<210> SEQ ID NO 39
<211> LENGTH: 468
<212> TYPE: PRT
<213> ORGANISM: Escherichia coli

<400> SEQUENCE: 39

```
Met Ser Lys Gln Gln Ile Gly Val Val Gly Met Ala Val Met Gly Arg
 1               5                  10                  15

Asn Leu Ala Leu Asn Ile Glu Ser Arg Gly Tyr Thr Val Ser Ile Phe
            20                  25                  30

Asn Arg Ser Arg Glu Lys Thr Glu Glu Val Ile Ala Glu Asn Pro Gly
        35                  40                  45

Lys Lys Leu Val Pro Tyr Tyr Thr Val Lys Glu Phe Val Glu Ser Leu
    50                  55                  60

Glu Thr Pro Arg Arg Ile Leu Leu Met Val Lys Ala Gly Ala Gly Thr
65                  70                  75                  80

Asp Ala Ala Ile Asp Ser Leu Lys Pro Tyr Leu Asp Lys Gly Asp Ile
                85                  90                  95

Ile Ile Asp Gly Gly Asn Thr Phe Phe Gln Asp Thr Ile Arg Arg Asn
            100                 105                 110

Arg Glu Leu Ser Ala Glu Gly Phe Asn Phe Ile Gly Thr Gly Val Ser
        115                 120                 125

Gly Gly Glu Glu Gly Ala Leu Lys Gly Pro Ser Ile Met Pro Gly Gly
    130                 135                 140

Gln Lys Glu Ala Tyr Glu Leu Val Ala Pro Ile Leu Thr Lys Ile Ala
145                 150                 155                 160

Ala Val Ala Glu Asp Gly Glu Pro Cys Val Thr Tyr Ile Gly Ala Asp
                165                 170                 175

Gly Ala Gly His Tyr Val Lys Met Val His Asn Gly Ile Glu Tyr Gly
            180                 185                 190
```

```
Asp Met Gln Leu Ile Ala Glu Ala Tyr Ser Leu Leu Lys Gly Gly Leu
    195                 200                 205

Asn Leu Thr Asn Glu Glu Leu Ala Gln Thr Phe Thr Glu Trp Asn Asn
    210                 215                 220

Gly Glu Leu Ser Ser Tyr Leu Ile Asp Ile Thr Lys Asp Ile Phe Thr
225                 230                 235                 240

Lys Lys Asp Glu Asp Gly Asn Tyr Leu Val Asp Val Ile Leu Asp Glu
                245                 250                 255

Ala Ala Asn Lys Gly Thr Gly Lys Trp Thr Ser Gln Ser Ala Leu Asp
                260                 265                 270

Leu Gly Glu Pro Leu Ser Leu Ile Thr Glu Ser Val Phe Ala Arg Tyr
    275                 280                 285

Ile Ser Ser Leu Lys Asp Gln Arg Val Ala Ala Ser Lys Val Leu Ser
    290                 295                 300

Gly Pro Gln Ala Gln Pro Ala Gly Asp Lys Ala Glu Phe Ile Glu Lys
305                 310                 315                 320

Val Arg Arg Ala Leu Tyr Leu Gly Lys Ile Val Ser Tyr Ala Gln Gly
                325                 330                 335

Phe Ser Gln Leu Arg Ala Ala Ser Glu Glu Tyr Asn Trp Asp Leu Asn
    340                 345                 350

Tyr Gly Glu Ile Ala Lys Ile Phe Arg Ala Gly Cys Ile Ile Arg Ala
    355                 360                 365

Gln Phe Leu Gln Lys Ile Thr Asp Ala Tyr Ala Glu Asn Pro Gln Ile
    370                 375                 380

Ala Asn Leu Leu Leu Ala Pro Tyr Phe Lys Gln Ile Ala Asp Asp Tyr
385                 390                 395                 400

Gln Gln Ala Leu Arg Asp Val Val Ala Tyr Ala Val Gln Asn Gly Ile
                405                 410                 415

Pro Val Pro Thr Phe Ala Ala Ala Val Ala Tyr Tyr Asp Ser Tyr Arg
    420                 425                 430

Ala Ala Val Leu Pro Ala Asn Leu Ile Gln Ala Gln Arg Asp Tyr Phe
    435                 440                 445

Gly Ala His Thr Tyr Lys Arg Ile Asp Lys Glu Gly Val Phe His Thr
    450                 455                 460

Glu Trp Leu Asp
465

<210> SEQ ID NO 40
<211> LENGTH: 1407
<212> TYPE: DNA
<213> ORGANISM: Escherichia coli

<400> SEQUENCE: 40
atgtcaaagc aacagatcgg cgtagtcggt atggcagtga tggggcgcaa cctagcgctc     60
aacatcgaaa gccgtggtta taccgtctct attttcaacc gctcccgtga agacggaaa    120 gaagtgattg ccgaaaatcc aggcaagaaa ctggttcctt actatacggt gaaagagttt    180
gttgaatctc tggaaacgcc tcgtcgcatc ctgttaatgg tgaaagcagg tgcaggcacg    240
gatgctgcta ttgattccct caagccgtac ctcgataaag gtgacatcat cattgatggt    300
ggtaacacct tcttccagga caccattcgt cgtaaccgtg agctttctgc cgaaggcttt    360
aacttcatcg gtaccggtgt ttccggcgga gaagaaggcg cgctgaaagg tccttccatt    420
atgcctggtg ggcagaaaga agcctatgaa ctggttgcgc cgatcctgac caaaatcgcc    480
gcagtggctg aagacggtga gccatgcgtt acctatattg tgccgatgg cgcaggtcac    540
```

```
tatgtgaaga tggttcacaa cggtattgaa tacggagata tgcaactgat tgctgaagcc    600
tattctctgc ttaaaggtgg cctgaacctc accaacgaag aactggcgca gacgtttacc    660
gagtggaata acgtgaact gagcagctac ctgatcgaca tcaccaaaga tatcttcacc     720
aaaaaagatg aagacggtaa ctacctggtt gatgtgatcc tggatgaagc ggctaacaaa   780
ggtaccggta atggaccag ccagagcgca ctggatctcg gcgaaccgct gtcgctgatt     840
accgagtctg tgtttgcacg ttatatctct tctctgaaag atcagcgtgt tgccgcatct   900
aaagttctct ctggcccgca agcacagcca gcaggcgaca aggctgagtt catcgaaaaa   960
gttcgccgtg cgctgtatct gggcaaaatc gtttcttacg cccagggctt ctctcagctg  1020
cgtgctgcgt ctgaagagta caactgggat ctgaactacg cgaaatcgc gaagattttc   1080
cgtgctggct gcatcattcg tgcgcagttc ctgcagaaaa ttaccgatgc ttatgccgaa  1140
aatccgcaga tcgctaacct gctgctggct ccgtacttca gcaaattgc gatgattac    1200
cagcaggcgc tgcgtgatgt cgttgcttat gcggtacaga acggtatccc ggttccgacc  1260
tcgccgctg cggttgccta ttacgatagc taccgtgccg ctgttctgcc tgcgaacctg   1320
atccaggcac agcgtgacta tttcggtgca catacttata agcgcattga taaagaaggt  1380
gtgttccata ctgaatggct ggattaa                                       1407

<210> SEQ ID NO 41
<211> LENGTH: 468
<212> TYPE: PRT
<213> ORGANISM: Escherichia coli

<400> SEQUENCE: 41

Met Ser Lys Gln Gln Ile Gly Val Val Gly Met Ala Val Met Gly Arg
1               5                   10                  15

Asn Leu Ala Leu Asn Ile Glu Ser Arg Gly Tyr Thr Val Ser Ile Phe
            20                  25                  30

Asn Arg Ser Arg Glu Lys Thr Glu Glu Val Ile Ala Glu Asn Pro Gly
        35                  40                  45

Lys Lys Leu Val Pro Tyr Tyr Thr Val Lys Glu Phe Val Glu Ser Leu
    50                  55                  60

Glu Thr Pro Arg Arg Ile Leu Leu Met Val Lys Ala Gly Ala Gly Thr
65                  70                  75                  80

Asp Ala Ala Ile Asp Ser Leu Lys Pro Tyr Leu Asp Lys Gly Asp Ile
                85                  90                  95

Ile Ile Asp Gly Gly Asn Thr Phe Phe Gln Asp Thr Ile Arg Arg Asn
            100                 105                 110

Arg Glu Leu Ser Ala Glu Gly Phe Asn Phe Ile Gly Thr Gly Val Ser
        115                 120                 125

Gly Gly Glu Glu Gly Ala Leu Lys Gly Pro Ser Ile Met Pro Gly Gly
    130                 135                 140

Gln Lys Glu Ala Tyr Glu Leu Val Ala Pro Ile Leu Thr Lys Ile Ala
145                 150                 155                 160

Ala Val Ala Glu Asp Gly Glu Pro Cys Val Thr Tyr Ile Gly Ala Asp
                165                 170                 175

Gly Ala Gly His Tyr Val Lys Met Val His Asn Gly Ile Glu Tyr Gly
            180                 185                 190

Asp Met Gln Leu Ile Ala Glu Ala Tyr Ser Leu Leu Lys Gly Gly Leu
        195                 200                 205

Asn Leu Thr Asn Glu Glu Leu Ala Gln Thr Phe Thr Glu Trp Asn Asn
    210                 215                 220
```

```
Gly Glu Leu Ser Ser Tyr Leu Ile Asp Ile Thr Lys Asp Ile Phe Thr
225                 230                 235                 240

Lys Lys Asp Glu Asp Gly Asn Tyr Leu Val Asp Val Ile Leu Asp Glu
            245                 250                 255

Ala Ala Asn Lys Gly Thr Gly Lys Trp Thr Ser Gln Ser Ala Leu Asp
        260                 265                 270

Leu Gly Glu Pro Leu Ser Leu Ile Thr Glu Ser Val Phe Ala Arg Tyr
    275                 280                 285

Ile Ser Ser Leu Lys Asp Gln Arg Val Ala Ala Ser Lys Val Leu Ser
290                 295                 300

Gly Pro Gln Ala Gln Pro Ala Gly Asp Lys Ala Glu Phe Ile Glu Lys
305                 310                 315                 320

Val Arg Arg Ala Leu Tyr Leu Gly Lys Ile Val Ser Tyr Ala Gln Gly
                325                 330                 335

Phe Ser Gln Leu Arg Ala Ala Ser Glu Glu Tyr Asn Trp Asp Leu Asn
            340                 345                 350

Tyr Gly Glu Ile Ala Lys Ile Phe Arg Ala Gly Cys Ile Ile Arg Ala
        355                 360                 365

Gln Phe Leu Gln Lys Ile Thr Asp Ala Tyr Ala Glu Asn Pro Gln Ile
    370                 375                 380

Ala Asn Leu Leu Leu Ala Pro Tyr Phe Lys Gln Ile Ala Asp Asp Tyr
385                 390                 395                 400

Gln Gln Ala Leu Arg Asp Val Val Ala Tyr Val Gln Asn Gly Ile
                405                 410                 415

Pro Val Pro Thr Phe Ala Ala Val Ala Tyr Tyr Ser Tyr Arg
            420                 425                 430

Ala Ala Val Leu Pro Ala Asn Leu Ile Gln Ala Gln Arg Asp Tyr Phe
        435                 440                 445

Gly Ala His Thr Tyr Lys Arg Ile Asp Lys Glu Gly Val Phe His Thr
    450                 455                 460

Glu Trp Leu Asp
465

<210> SEQ ID NO 42
<211> LENGTH: 1407
<212> TYPE: DNA
<213> ORGANISM: Escherichia coli

<400> SEQUENCE: 42
atgtccaagc aacagatcgg cgtcatcggt atggctgtga tggggcgcaa cttggctcta      60
aacatcgaga gccgtggtta taccgtatcc gtctataatc gctcgcgtga aaaaactgaa     120
gaggttgttg ccgaaaaccc aggtaagaaa ctggtcccctt attacacggt taaagagttc     180
gtcgagtctc ttgaaactcc acgccgtatc ctgttaatgg tcaaagcggg tgctggcact     240
gatgctgcga ttaattccct gaagcccctat ctagataaag cgacatcat cattgatggc     300 ggtaatacct tctttcagga cacaattcgt cgtaaccgtg aactttccgc ggaaggcttt     360
aactttatcg gggccggggt ttcaggtggt gaagagggcg cgctgaaagg cccatctatc     420
atgcctggtg gccagaaaga tgcgtatgaa atggttgtgc caatcctgac caagattgcc     480
gcgatagctg aagatggtga accgtgcgtg acgtatattg gtgcggatgg tgcaggtcat     540
tacgtgaaga tggtgcacaa cggtatcgaa tatggcgata tgcaattgat agctgaagcc     600
tattctctgc tgaaaggtgc cctaaatctg tctaatgaag agttagcctc tatctttaat     660
gaatggaatg aaggcgagct gagcagctat ctgattgaca tcactaagga tatcttcaac     720
```

-continued

```
aaaaaagatg aagagggtaa atacttggtt gatgtgattt tggacgaagc tgcgaacaaa   780
ggtacaggca aatggaccag ccagagctct cttgatctag cgaaccgct gtcgttgatc    840 accgaatccg tatttgcccg ctacatctcc tctctgaaag accagcgtgt tgcggcctct   900
aaagtgctgt ctggcccgca ggctaaactg ctagtgata aagctgagtt tgttgagaaa    960
gtacgccgtg ccttgtacct aggcaaaatt gtctcttatg cccaaggctt ttctcaactt  1020
cgtgccgcat cagagcaata caactgggat ttgaactacg gtgaaatcgc gaaaattttc  1080
cgcgcaggct gcattattcg tgcacagttc ctccagaaaa tcaccgacgc ttatgctgaa  1140
aacaaagata ttgcaaacct gctgcttgct ccgtatttca acatatcgc tgatgaatat   1200 caacaagccc tccgtgatgt agtgtcttat gctgtgcaga acggtattcc ggtaccgact  1260
ttctccgccg ctgtagctta ctacgacagc taccgttctg cggttctgcc ggctaacttg  1320
atccaagcac agcgtgatta tttcggtgcg cacacgtata aacgcattga taaagaaggt  1380
gtttttcata cagaatggct agaataa                                     1407
```

<210> SEQ ID NO 43
<211> LENGTH: 468
<212> TYPE: PRT
<213> ORGANISM: Escherichia coli

<400> SEQUENCE: 43

```
Met Ser Lys Gln Gln Ile Gly Val Ile Gly Met Ala Val Met Gly Arg
1               5                   10                  15

Asn Leu Ala Leu Asn Ile Glu Ser Arg Gly Tyr Thr Val Ser Val Tyr
            20                  25                  30

Asn Arg Ser Arg Glu Lys Thr Glu Glu Val Val Ala Glu Asn Pro Gly
        35                  40                  45

Lys Lys Leu Val Pro Tyr Tyr Thr Val Lys Glu Phe Val Glu Ser Leu
    50                  55                  60

Glu Thr Pro Arg Arg Ile Leu Leu Met Val Lys Ala Gly Ala Gly Thr
65                  70                  75                  80

Asp Ala Ala Ile Asn Ser Leu Lys Pro Tyr Leu Asp Lys Gly Asp Ile
                85                  90                  95

Ile Ile Asp Gly Gly Asn Thr Phe Phe Gln Asp Thr Ile Arg Arg Asn
            100                 105                 110

Arg Glu Leu Ser Ala Glu Gly Phe Asn Phe Ile Gly Ala Gly Val Ser
        115                 120                 125

Gly Gly Glu Glu Gly Ala Leu Lys Gly Pro Ser Ile Met Pro Gly Gly
    130                 135                 140

Gln Lys Asp Ala Tyr Glu Met Val Val Pro Ile Leu Thr Lys Ile Ala
145                 150                 155                 160

Ala Ile Ala Glu Asp Gly Glu Pro Cys Val Thr Tyr Ile Gly Ala Asp
                165                 170                 175

Gly Ala Gly His Tyr Val Lys Met Val His Asn Gly Ile Glu Tyr Gly
            180                 185                 190

Asp Met Gln Leu Ile Ala Glu Ala Tyr Ser Leu Leu Lys Gly Ala Leu
        195                 200                 205

Asn Leu Ser Asn Glu Glu Leu Ala Ser Ile Phe Asn Glu Trp Asn Glu
    210                 215                 220
```

```
Gly Glu Leu Ser Ser Tyr Leu Ile Asp Ile Thr Lys Asp Ile Phe Asn
225                 230                 235                 240

Lys Lys Asp Glu Glu Gly Lys Tyr Leu Val Asp Val Ile Leu Asp Glu
                245                 250                 255

Ala Ala Asn Lys Gly Thr Gly Lys Trp Thr Ser Gln Ser Ser Leu Asp
            260                 265                 270

Leu Gly Glu Pro Leu Ser Leu Ile Thr Glu Ser Val Phe Ala Arg Tyr
        275                 280                 285

Ile Ser Ser Leu Lys Asp Gln Arg Val Ala Ala Ser Lys Val Leu Ser
290                 295                 300

Gly Pro Gln Ala Lys Leu Ala Ser Asp Lys Ala Glu Phe Val Glu Lys
305                 310                 315                 320

Val Arg Arg Ala Leu Tyr Leu Gly Lys Ile Val Ser Tyr Ala Gln Gly
                325                 330                 335

Phe Ser Gln Leu Arg Ala Ala Ser Glu Gln Tyr Asn Trp Asp Leu Asn
                340                 345                 350

Tyr Gly Glu Ile Ala Lys Ile Phe Arg Ala Gly Cys Ile Ile Arg Ala
        355                 360                 365

Gln Phe Leu Gln Lys Ile Thr Asp Ala Tyr Ala Glu Asn Lys Asp Ile
370                 375                 380

Ala Asn Leu Leu Leu Ala Pro Tyr Phe Lys His Ile Ala Asp Glu Tyr
385                 390                 395                 400

Gln Gln Ala Leu Arg Asp Val Val Ser Tyr Ala Val Gln Asn Gly Ile
                405                 410                 415

Pro Val Pro Thr Phe Ser Ala Ala Val Ala Tyr Tyr Asp Ser Tyr Arg
            420                 425                 430

Ser Ala Val Leu Pro Ala Asn Leu Ile Gln Ala Gln Arg Asp Tyr Phe
            435                 440                 445

Gly Ala His Thr Tyr Lys Arg Ile Asp Lys Glu Gly Val Phe His Thr
        450                 455                 460

Glu Trp Leu Glu
465
```

POLYMORPHIC LOCI THAT DIFFERENTIATE *ESCHERICHIA COLI* O157:H7 FROM OTHER STRAINS

CROSS-REFERENCE TO RELATED APPLICATIONS

This application is a continuation application of U.S. patent application Ser. No. 09/875,573, filed Jun. 5, 2001, which is a continuation application of International Application No. PCT/US99/29149, filed Dec. 8, 1999, and which International Application claims the benefit of U.S. Provisional Patent Application No. 60/111,493, filed Dec. 8, 1998, all of which are hereby expressly incorporated herein by reference in their entireties.

STATEMENT REGARDING SEQUENCE LISTING SUBMITTED ON CD-ROM

The Sequence Listing associated with this application is provided on CD-ROM in lieu of a paper copy, and is hereby incorporated by reference into the specification. Three CD-ROMs are provided, containing identical copies of the sequence listing: CD-ROM No. 1 is labeled COPY 1, contains the file 403c1.app.txt which is 93 KB and created on Apr. 12, 2007; CD-ROM No. 2 is labeled COPY 2, contains the file 403c1.app.txt which is 93 KB and created on Apr. 12, 2007; CD-ROM No. 3 is labeled CRF (Computer Readable Form), contains the file 403cl.app.txt which is 93 KB and created on Apr. 12, 2007.

FIELD OF THE INVENTION

The present invention relates generally to the field of microbiology and food sciences. More particularly, the inventor has discovered the gnd gene and corresponding 6-phosphogluconate dehydrogenase (6-PGD) protein from fourteen different strains of *Escherichia coli* and polymorphic sequences therein. Novel biotechnological tools, diagnostics, and food screening techniques are provided.

BACKGROUND OF THE INVENTION

*Escherichia coli* O157:H7 is an exceptionally virulent food-borne, human pathogen that causes a spectrum of illness, including asymptomatic and post-symptomatic carriage, mild diarrhea, bloody diarrhea/hemorrhagic colitis, and the postdiarrheal, potentially lethal, hemolytic uremic syndrome (HUS). (Wilson et al., *J Infect Dis*, 174:1021-1027 (1996); (Karch et al., *J Clin Microbiol*, 33:1602-1605 (1995); (Rodrigue et al., *J Infect Dis*, 172:1122-1125 (1995); (Riley et al., *N Engl J Med*, 308:681-685 (1983); (Karmali et al., *Lancet*, 1:619-620 (1983); Neill et al., *Arch Intern Med*, 145: 2215-2217 (1985); Neill et al., *Pediatrics*, 80:37-40 (1987); and Tarr et al., *J Infect Dis*, 162:553-556 (1990)). While other *E. coli* strains are considered in some contexts to be pathogens, the excessive pathogenicity of *E. coli* O157:H7 is a well recognized distinguishing feature.

HUS is defined as a triad of non-immune microangiopathic hemolytic anemia, thrombocytopenia, and acute renal failure. HUS is chiefly a disorder of children under age 10, however, the elderly are also susceptible to severe complications of *E. coli* O157:H7 gastrointestinal infections. (Martin et al., N Engl *J Med*, 323:1161-1167 (1990); Siegler et al., Pediatrics, 94:35-40 (1994); Tarr and Hickman, *Pediatrics*, 80:41-45 (1987); Tarr et al., *Am J Epidemiol*, 129:582-586 (1989); Tarr et al., *J Infect Dis*, 162:553-556 (1990); (Carter et al., *N Engl J Med*. 317:1496-1500 (1987); and Ryan et al., *J Infect Dis*, 154:631-638 (1986)).

HUS follows gastrointestinal infection with *E. coli* O157: H7 in approximately 10-15% of pediatric cases. (Bell et al., *JAMA*, 272:1349-1353 (1994) and Bell et al., *Pediatrics*, 100: E12 (1997)). Approximately three-quarters of children with HUS require blood transfusions and approximately one-half require dialysis. (Tarr et al., *Am J Epidemiol*, 129:582-586 (1989); (Brandt et al., *J Pediatr*, 125:519-526 (1994); and Tarr et al., *Am J Epidemiol*, 129:582-586 (1989)). Despite recognition of O157:H7 infection and the use of modern pediatric intensive care, about 5-10% of those infected die. (Brandt et al., *J Pediatr*, 125:519-526 (1994) and Tarr et al., *Am J Epidemiol*, 129:582-586 (1989)). Investigation of O157:H7 outbreaks have provided evidence that the infectious dose is low. For example, limited exposure to a municipal lake in Portland, Oreg., wherein the levels of *E. coli* O157:H7 were undetectable, was sufficient to produce disease in visitors. (Keene et al., *N Engl J Med*, 331:579-584 (1994)) and during a salami-associated outbreak in the Pacific Northwest in 1994, investigators concluded that the people who became ill had consumed between 2 and 45 viable *E. coli* O157:H7 organisms. (Tilden et al., *Am J Public Health*, 86:1142-1145 (1996)).

*E. coli* O157:H7 is often found in food and environmental vehicles that do not always undergo an efficient bacterial killing process. Large outbreaks have been caused by the interstate dissemination of contaminated ground beef that was under cooked (Bell et al., *JAMA*, 272:1349-1353 (1994) and Riley et al., *N Engl J Med*, 308:681-685 (1983)); salted, fermented, but uncooked salami (Tilden et al., *Am J Public Health*, 86:1142-1145 (1996)); municipal (Swerdlow et al., *Ann Intern Med*, 117:812-819 (1992)) and swimming (Keene et al., *N Engl J Med*, 331:579-584 (1994)) water; unpasteurized apple juice (Anonymous, *Morb Mortal Wkly Rep*, 45:975 (1996)); unpasteurized milk (Keene et al., *J Infect Dis*, 176: 815-818 (1997)); and lettuce (Ackers et al., *J Infect Dis*, 177:1588-1593 (1998)). Improper food handling has been reported to be a significant factor associated with human infection. (Mead et al., *Arch Intern Med*, 157:204-208 (1997)).

*E. coli* O157:H7 has not been shown to possess a capsular polysaccharide but it expresses an O side chain antigen designated 157, which consists of repeating tetrasaccharide units of variable length. These tetrasaccharide units comprise the antigenic O157 lipopolysaccharide (LPS). In contrast to other *E. coli* strains, O157:H7 fails to ferment sorbitol after overnight culture on MacConkey agar into which sorbitol rather than lactose is incorporated as the carbon source. (Wells et al., *J Clin Microbiol*, 18:512-520 (1983); March et al., *J Clin Microbiol*, 23:869-872 (1986)). *E. coli* O157:H7 also fails to produce β-glucuronidase, another metabolic distinguishing factor. (Ratnam et al., *J Clin Microbiol*, 26:2006-2012 (1988)). Sorbitol non-fermenting *E. coli* almost always express the H7 flagellar antigen, though occasional sorbitol non-fermenting *E. coli* O157 strains recovered in the United States do not express the H7 antigen. (Slutsker et al., *Ann Intern Med*, 126:505-513 (1997)). Another variant of *E. coli* O157:H7 has been found in Germany and Czech Republic, which expresses the O157 antigen, but are non-motile pathogens that ferment sorbitol. (Bielaszewska et al., *J Clin Microbiol*, 36:2135-2137 (1998); Gunzer et al., *J Clin Microbiol*, 30:1807-1810 (1992)). Such sorbitol non-fermenting *E. coli* O157 variants are difficult to identify by using the sorbitol MacConkey agar screening technique.

Current diagnostic approaches involve monitoring the growth characteristics of cultured *E. coli* on MacConkey agar, as described above, and utilizing a seriological agent specific for O157 LPS. That is, organisms with an appearance typical of *E. coli* on sorbitol MacConkey agar, that fail to ferment sorbitol, react with a serologic reagent specific for the O157 LPS side chain but fail to react with a control (negative) reagent are considered to be Shiga-toxigenic, and, presumably, pathogenic, *E. coli* O157:H7. The identification of the H7 antigen and the toxinogenic phenotype are not necessary for clinical purposes because sorbitol non-fermenting *E. coli* that are non mucoid, react with a specific O157 antigen determining reagent and do not react with a negative control reagent are almost always toxigenic. (Strockbine et al., "Overview of detection and subtyping methods," *Escherichia coli* O157:*H7 and other Shiga toxin-producing E. coli*, Chapter 33, Kaper and O'Brien, eds., Washington, D.C.: ASM Press, 1998:331-356 and Tarr, "Shiga toxin-producing *Escherichia coli* infections: challenges and opportunities," *Escherichia coli* O157:*H7 and other Shiga toxin-producing E. coli*, Chapter 39, Kaper and O'Brien, eds., Washington, D.C.: ASM Press, 1998:393-402).

Alternate diagnostic approaches have been recently developed. One approach involves the detection of the presence of released Shiga-toxin. These tests either exploit the ability of Shiga-toxins to bind to a glycosphingolipid ligand (globotriaosylceramide) (Basta et al., *J Clin Microbiol*, 27:1617-1622 (1989)) (Biocarb, Gaithersburg, Md.) or employ an enzyme immunoassay (Meridian Diagnostics, Cincinnati, Ohio). (Kehl et al., *J Clin Microbiol*, 35:2051-2054 (1997)); Park et al., *Diag Microbiol Infect Dis*, 26:69-72 (1996)). These tests have the advantage that they detect Shiga toxigenic *E. coli* besides *E. coli* O157:H7. Several diagnostic tests also involve the use of probes or primers to detect sequences of O157:H7 through hybridization, enzyme cleavage, or Polymerase Chain Reaction (PCR). (See e.g., U.S. Pat. Nos. 5,738,995; 5,747,257; and 5,756,293).

A variety of techniques to identify excessively pathogenic *E. coli* in food have also been developed. (Bennett et al., *Lett Appl Microbiol*, 22:237-243 (1996); Bennett et al., *Lett Appl Microbiol*, 20:375-379 (1995); Blanco et al., *Microbiologia*, 12:385-394 (1996); Bolton et al., *Lett Appl Microbiol*, 23:317-321 (1996); Doyle and Schoeni, *Appl Environ Microbiol*, 53:2394-2396 (1987); Feldsine et al., *JAOAC Int*, 80:517-529 (1997); Feldsine et al., *JAOAC Int*, 80:530-543 (1997); Feldsine et al., *JAOAC Int*, 80:43-48 (1997); Feldsine et al., *J AOAC Int*, 80:37-42 (1997); Jinneman et al., *J Food Protect*, 58:722-726 (1995); Johnson et al., *Appl Environ Microbiol*, 61:386-388 (1995); Kim and Doyle, *Appl Environ Microbiol*, 58:1764-1767 (1992); Notermans et al., *Int J Food Microbiol*, 13:31-40 (1991); Okrend et al., *J Food Protect*, 53:936-940 (1990); Padhye and Doyle, *Appl Environ Microbiol*, 57:2693-2698 (1991); Pawelzik, *Acta Microbiol Hung*, 38:315-320 (1991); Ratnam and March, *Can Med Assoc J*, 134:43-46 (1986); Read et al., *Epidemiol Infect*, 105:11-20 (1990); Sequel, *Can Med Assoc J*, 143:519-521 (1990); Tortorello and Stewart, *Appl Environ Microbiol*, 60:3553-3559 (1994); Vernozy-Rozand et al., *Revue de Medecine Veterinaire*, 149:239-244 (1998); Vemozy-Rozand et al., *Revue de Medecine Veterinaire*, 148:879-882 (1997); Vernozy-Rozand et al., *Lett Appl Microbiol*, 25:442-446 (1997); Willshaw et al., *J Appl Bacteriol*, 75:420-426 (1993); Yu and Bruno, *Appl Environ Microbiol*, 62:587-592 (1996)). Many of these techniques include a hydrophobic grid membrane filter (Doyle and Schoeni, *Appl Environ Microbiol*, 53:2394-2396 (1987)), a dipstick immunoassay (Padhye and Doyle, *Appl Environ Microbiol*, 57:2693-2698 (1991)), multiplex polymerase chain reaction (Jinneman et al., *J Food Protect*, 58:722-726 (1995)), standard microbiologic techniques, immunomagnetic bead separation (Bennett et al., *Lett Appl Microbiol*, 22:237-243 (1996); Blanco et al., *Microbiologia*, 12:385-394 (1996); Karch et al., *J Clin Microbiol*, 34:516-519 (1996); Vernozy-Rozand et al., *Lett Appl Microbiol*, 25:442-446 (1997); and (Yu and Bruno, *Appl Environ Microbiol*, 62:587-592 (1996)) or combinations thereof. There remains a need for a better understanding of the origin of virulent strains of *E. coli*, in particular O157:H7, and novel approaches to rapidly detect the presence of these organisms in infected individuals and vehicles including, but not limited to, food and water supplies.

SUMMARY OF THE INVENTION

In the present invention the inventor has discovered the gnd gene and corresponding 6-phosphogluconate dehydrogenase (6-PGD) protein of fourteen strains of *E. coli*. Within these genes and proteins the inventor has also found several polymorphisms that can be used to identify the presence of a particular strain of *E. coli* and/or differentiate one strain of *E. coli* from another. One polymorphism in particular, which involves a substitution of an isoleucine molecule for a threonine molecule at amino acid position 218, can be used to differentiate highly pathogenic strains of O157:H7 and O55:H7 from less pathogenic strains of O157:H7. Since O55:H7 is only about 82% homologous to O157:H7, the highly pathogenic strains of O157:H7 can be differentiated from O55:H7 at several different loci. By identifying the presence and/or absence of the polymorphism at position 218 and identifying the presence or absence of a region of non-homology between O55:H7 and O157:H7, one of skill in the art can rapidly identify the presence of a highly pathogenic strain of *E. coli* in a sample obtained from a patient or from a food or liquid source. Further, by identifying the presence or absence of other polymorphisms in the gnd locus, one of skill can efficiently differentiate specific strains of *E. coli* allowing for a more precise diagnosis or screening.

Embodiments of the invention include an isolated polynucleotide encoding gnd, wherein the polynucleotide comprises one of the *E. coli* sequences disclosed in the sequence listing. Fragments of these sequences having least 9 consecutive bases and a polymorphism described in Table 1 are also embodiments of the invention. Other embodiments include isolated polynucleotides that encode a polypeptide that corresponds to the *E. coli* nucleic acid sequences disclosed in the sequence listing and polynucleotides of at least 9 bases that hybridize to a nucleotide sequence found in the sequence listing under the following conditions: 7% sodium dodecyl sulfate (SDS), 0.5M NaPO4 pH 7.0, 1 mM EDTA at 50° C.; and washing with 1% SDS at 42° C. A additional embodiment concerns a nucleic acid probe for detecting the presence of *E. coli* O157:H7 consisting of an isolated nucleic acid molecule at least 7 nucleotides in length, wherein the nucleic acid molecule hybridizes to DNA of gnd of *E. coli* O157:H7 and not to DNA of gnd of non-H7 *E. coli* O157 strains. Another aspect involves a nucleic acid primer for detecting the presence of *E. coli* O157:H7 consisting of an isolated nucleic acid molecule at least 7 nucleotides in length, wherein the isolated nucleic acid molecule primes DNA of gnd of *E. coli* O157:H7 and not DNA of gnd of non-H7 *E. coli* O157 strains. The nucleic acid probes of the invention can be provided on a substrate or in a microarray on a chip.

SRecombinant constructs and vectors comprising one of the sequences of the sequence listing are also embodiments of the invention. Further, a cultured cell line comprising the one of the vectors of the invention is an embodiment. The proteins of the invention include an isolated protein comprising one of the sequences found in the sequence listing and an isolated polypeptide comprising at least 3 consecutive amino acids of one of the sequences of the sequence listing, wherein the polypeptide contains at least one polymorphism that can be deduced from Table 1. Additional protein embodiments concern an isolated antibody capable of specifically binding to a protein having one of the sequences of the sequence listing, wherein the epitope corresponds to at least one polymorphism that can be deduced from Table 1. Further, another embodiment includes an isolated antibody capable of binding to a polypeptide comprising at least 9 consecutive amino acids of one of the sequences of the sequence listing, wherein the epitope corresponds to at least one polymorphism that can be deduced from Table 1. In some embodiments, the antibody is monoclonal.

Methods of detecting a polymorphism and detecting or diagnosing the presence of a highly pathogenic E. coli are also embodiments. By one approach, a polymorphism in a gene encoding 6-PGD is detected by obtaining a biological sample containing polynucleotides and analyzing the biological sample for the presence of a diagnostic polynucleotide having at least one polymorphism described in Table 1. In some aspects, the presence or absence of the C653T or G653C polymorphism is analyzed and/or the analysis of the biological sample further comprises a DNA amplification step. Another method concerns the identification of a pathogenic or non-pathogenic E. coli. This approach is practiced by obtaining a biological sample containing polynucleotides, analyzing the biological sample for the presence of a diagnostic polynucleotide having at least one polymorphism described in Table 1, and identifying the E. coli as a pathogenic or non-pathogenic strain based on the presence or absence of at least one polymorphism described in Table 1. In some aspects of this embodiment, the presence or absence of the C653T or G653C polymorphism is analyzed and/or the analysis of the biological sample further comprises a DNA amplification step.

Other methods of the invention include, a method of making a 6-PGD protein comprising the steps of obtaining a cDNA comprising one of the sequences of the sequence listing, inserting the cDNA in an expression vector such that the cDNA is operably linked to a promoter, and introducing the expression vector into a host cell whereby the host cell produces the protein encoded by the cDNA. This method can also be used in conjunction with a step involving the isolation of the protein. An additional method concerns the construction of a transformed host cell that expresses one of the sequences of the sequence listing. This method includes the steps of transforming a host cell with a recombinant DNA vector suitable for gene expression. Additionally, a method for detecting the presence of E. coli O157:H7 in a sample is provided, which involves the steps of: (a) contacting said sample, under hybridization conditions, with a nucleic acid probe that selectively hybridizes to a nucleic acid sequence from gnd of E. coli O157:H7 and not to nucleic acid sequence from gnd of non-H7 E. coli O157 strains, to form a hybridization complex and (b) detecting formation of said hybridization complex as an indication of the presence of E. coli O157:H7 in the sample.

BRIEF DESCRIPTION OF THE DRAWINGS

FIG. 1 shows a graphical representation of the polymorphisms present at the gnd locus in several strains of E. coli. Bars represent the 1407 bp gnd allele and the vertical lines represent sites of polymorphisms determined by comparison to a consensus sequence.

FIG. 3 is a representation of a chromosome having the gnd locus and flanking regions.

DETAILED DESCRIPTION OF THE INVENTION

Figure 2:
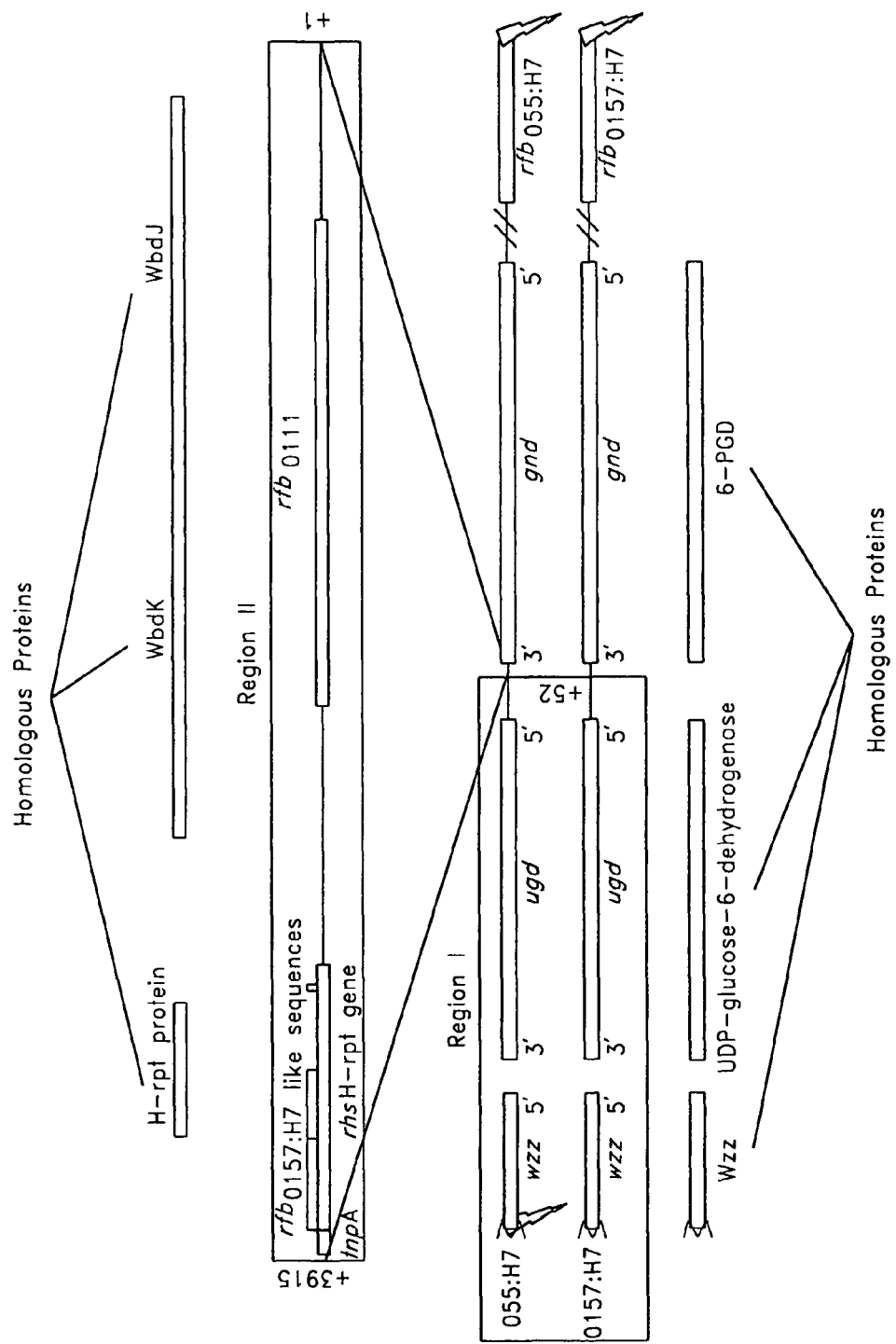
FIG. 2 shows the homology between chromosomes of E. coli O55:H7 and E. coli O157:H7 observed 3916 nucleotides downstream of the 3' terminus of gnd of E. coli O55:H7, and 52 nucleotides downstream of the 3' terminus of gnd of E. coli O157:H7. Elements of interest in the extra DNA in E. coli O55:H7 include a segment of homology to tnpA of S. enterica Typhimurium, an H-repeat protein gene with segments homologous to noncoding parts of the E. coli O157 rjb cluster, wbdJ and wbdK. Orfs are noted as homologous proteins. Loci are oriented chromosomally.

Herein the inventor describes the discovery of the gnd gene and corresponding 6-phosphogluconate dehydrogenase (6-PGD) protein of fourteen strains of E. coli. Within these genes and proteins the inventor has also found several genetic differences or "polymorphisms" that can be used to identify the presence of a particular strain of E. coli and/or differentiate one strain of E. coli from another. One polymorphism in particular involves a substitution of an isoleucine molecule for a threonine molecule at amino acid position 218. This polymorphism is referred to as "T218I" or "Thr218Iso". In some contexts, this form of 6-PGD or a polynucleotide encoding this form of 6-PGD (i.e., an isoleucine at amino acid position 218 or a polynucleotide encoding an isoleucine at position 218) is referred to as "Iso218", whereas a 6-PGD molecule having a threonine at amino acid position 218 or a polynucleotide encoding a threonine at position 218 is referred to as "Thr218". In other contexts, the term "Iso218" refers to a polymorphism in a polynucleotide encoding a fragment of 6-PGD (in which case the polymorphism is with reference to codon 218 of the 6-PGD fragment-encoding polynucleotide), or to a fragment of the 6-PGD protein itself (in which case the polymorphism is with reference to amino acid position 218 of the 6-PGD polypeptide sequence provided in the sequence listing. This polymorphism can also be referred to by the nucleotide differences that encode the Iso218 polymorphism. That is, the Thr218 polymorphism results from the presence of a cytosine and guanine residue at nucleotide positions 653 and 654, respectively; whereas, the Iso218 polymorphism has a thymine and cytosine at positions 653 and 654, respectively. Thus, other ways of referring to the polymorphism at amino acid residue 218 include "C→T mutation at nucleotide position 653" and/or a "G→C" mutation at nucleotide position 654" or "C653T" and/or "G654C".

In the following disclosure, the inventor describes the cloning, sequencing, and characterization of fourteen gnd genes and corresponding proteins from different strains of E. coli. Evidence is also provided of the existence of one or more mobile DNA element(s) within the gnd-rjb region that has co-transferred among E. coli and accounts for the antigenic changes that resulted in the emergence of pathogenic E. coli that express the O55 and O157 antigens. Biological tools, diagnostics, and methods of use of the foregoing are described in the sections that follow. These embodiments are useful for the rapid identification of the presence of a specific strain of E. coli, and the differentiation of one strain of E. coli from another, for example, the excessively virulent strains of O157:H7 from less pathogenic strains of E. coli. In the section below, the inventor describes the cloning, sequencing, and characterization of the fourteen gnd genes and corresponding proteins of different strains of *E. coli*.

Cloning, Sequencing, and Characterization of gnd Genes and Corresponding Proteins of Different *E. coli* Strains Recently, research has focussed on the use of the rjb region (a cluster of genes that encodes the enzyme necessary for the production of the *E. coli* O157 O side chain antigen) of *E. coli* O157:H7 as a potential target for DNA based detection systems in food and water supplies and human clinical specimens. (Desmarchelier et al., *J Clin Microbiol*, 36:1801-1804 (1998); (Feng et al., *J Clin Microbiol*, 36:2339-2341 (1998); and (Paton and Paton, *J Clin Microbiol*, 36:598-602 (1998)). While the expression of the O157 antigen and the presence of the rfb region encoded in this antigen are necessary components of a pathogenic *E. coli* O157, diverse non-toxigenic *E. coli* O157 exist that express H antigens 3, 16, 43, and 45 and contain sequences homologous to the *E. coli* O157:H7 rjb region. (Bilge et al., *Infect Immun*, 64:4795-4801 (1996)). Such organisms frustrate a diagnostic strategy based upon the detection of genetic differences in the rjb region. (Wang et al., *Infect Immun*, 66:3545-3551 (1998)).

The rfb cluster of genes occurs at approximately 44 minutes on the *E. coli* chromosome. These clusters are generally between 8 and 14 kb in length and contain approximately 8 to 12 contiguous genes that act in concert to produce the 0 side chain lipopolysaccharide. (Reeves, *New Compr Biochem*, 27:281-314 (1994); Reeves et al., *Trends Microbiol*, 4:495-503 (1996)). Adjacent to the rjb cluster is the gnd allele that encodes 6-phosphogluconate dehydrogenase (6-PGD) (EC 1.1.1.44), the third enzyme in the pentose-phosphate pathway. Although gnd encodes a "housekeeping" gene with critical bacterial function, this allele is highly polymorphic, when compared to other "housekeeping" genes in the *E. coli* chromosome. (Whittam and Ake, "Mechanisms of molecular evolution," Sinauer, Takahata and Clark, eds., Sunderland, Mass.: 1993:223-245). It is believed by some that the polymorphisms at the gnd locus result from inter-strain or inter-species transfers and subsequent recombination with *Salmonella*. (Barcak and Wolf, Jr., *J Bacteriol*, 170:372-379 (1988); Beltran et al., *Proc Natl Acad Sci USA*, 85:7753-7757 (1988); Bisercic et al., *J Bacteriol*, 173:3894-3900 (1991); Boyd et al., *J Gen Microbiol*, 139:1125-1132 (1993); Dykhuizen and Green, *J Bacteriol*, 173:7257-7268 (1991); and Selander et al., *Infect Immun*, 58:2262-2275 (1990)).

By one model, the "hitchhiking hypothesis", the rjb region of *E. coli* is believed to have been acquired via horizontal transfer from other species by virtue of sequence homology and low G+C content. That is, gnd and rfb are thought to co-transfer or "hitchhike" with rjb. (Nelson and Selander, *Proc Natl Acad Sci USA*, 91:10227-10231 (1994)). In support of this hypothesis are the discordant electromorphic appearances of 6-PGD of *E. coli* O157:H7 and its closest non-O157:H7 relative, *E. coli* O55:H7. Among other evolutionary events including the acquisition of bacteriophage encoding the Shiga toxin genes, the *E. coli* O157:H7 large plasmid, and the loss of the ability to ferment sorbitol, it has been speculated that the *E. coli* O55:H7 rjb region was exchanged for the *E. coli* O157:H7 rjb region. (Feng et al., *J Clin Microbiol*, 36:2339-2341 (1998)).

While the current paradigm explains the observed polymorphic gnd structure as being a result of selective pressures on gnd itself, the inventor set out to prove that the genetic diversity at the gnd locus resulted from the close proximity of gnd to the rjb cluster and the fact that the rjb genes encode bacterial surface molecules that are efficiently targeted by the immune system. The inventor reasoned that the gnd locus, as well as other genes within the rjb cluster, co-evolved with the immune system and, thus, the polymorphisms within these genes could be used to identify and differentiate the O157:H7 *E coli* from other strains of *E. coli*, including bacteria expressing a nonpathogenic form of the O157 antigen. Accordingly, the inventor cloned and sequenced the gnd genes of virulent strains of *E. coli* O157:H7, *E. coli* O55:H7, and *E. coli* that express the O157 antigen but are not as pathogenic to humans as *E. coli* O157:H7 and determined that, indeed, a relationship existed between polymorphisms within genes of the rfb cluster, in particular gnd and pathogenicity.

The gnd genes of *E. coli* O157:H7 and the other *E. coli* strains were cloned from purified bacterial DNA. To obtain genomic or plasmid DNA, bacteria were grown overnight in LB broth (Maniatis et al., *Molecular cloning: a laboratory manual*, Cold Spring Harbor Laboratory, (1982)) without antibiotics or with ampicillin (200 mg/mL), respectively, at 37° C. For genomic DNA, bacteria (3 ml), pelletted by centrifugation, were suspended in 50 millimolar (mM) Tris-HCl (pH8.0) and 50 mM ethylenediamine tetraacetic acid (EDTA). Ten microliters (□l) of 20% SDS were added to this mix simultaneous with the addition of 18 □l of proteinase K (20 mg/ml). These chemicals were obtained from Sigma (St. Louis, Mo.). Bacteria were incubated at 65° C. for 2-24 hours, and were then extracted once or more times with phenyl-chloroform-isoamyl alcohol (25:24:1), and back extracted with chloroform-isoamyl alcohol (24:1). The resulting aqueous DNA was then precipitated at room temperature adding 10M ammonium acetate to a concentration of 2.5M, followed by the addition of 2.5 volumes of 100% ethanol. The precipitate was centrifuged, washed once with 100% ethanol, air dried, and solubilized in 10 mM Tris-HCl (pH8.0), containing 1 mM ETDA. Plasmids were obtained and prepared using the Qiaprep Spin Miniprep Kit (Qiagen Inc., Valencia, Calif.) and manufacturer's instructions.

To amplify gnd from *E. coli* expressing the O157 antigen, the inventor initially used the primer pair (1)—5'CACG-GATCCGATCACACCTGACAGGAGTA3' (SEQ. ID. No. 1) (for the rjb side) and 5'CCGGAATTC-CGGGCAAAAAAAGCCCGGTGCAA3' (SEQ. ID. No. 2) (for the his side), which were derived from published sequences (Bisercic et al., *J Bacteriol*, 173:3894-3900 (1991)) and were modified to contain BamHI and EcoRI sites for cloning purposes. However, these primers failed to obtain an amplicon from *E. coli* O55:H7 DNA. Therefore, the consensus oligonucleotides of primer pair (2)—5'CGGAATTC-CGCGCTCAACATCGANAGCCGTGG3' (SEQ. ID. No. 3) and 5'CGGAATTCCGCCTGGATCAGGTTAGCCGG3' (SEQ. ID. No. 4) (derived from a computerized data base of *E. coli* gnd sequences and having 5' EcoRI sites) were used to prime DNA from strain TB 182A (an *E. coli* O55:H7 strain). (Bokete et al., *J Infect Dis*, 175:1382-1389 (1997)). These primers produced a PCR product of approximately 1.3 kb, consisting of the internal portion of the gnd gene. Sequence analysis of this amplicon determined that the following primer pairs would prime DNA close to the 5' and 3' termini, respectively, of this allele:

```
                                                    (SEQ. ID. No. 5)
(3)   5'CGGGGTACCCCGTAAGGGACCAGTTTCTTACCTGGG3'
and (SEQ. ID. No. 6)
      5'GCCCTATCTAGATAAAGG3';
```

```
                                                    (SEQ. ID. No. 7)
(4)   5'AGTTAAAGCCTTCCGCGG3'
and (SEQ. ID. No. 8)
      5'TGCCCGCTACATCTCCTC3';
and (SEQ. ID. No. 9)
(5)   5'GTTGTACTCTTCAGACGC3')
and (SEQ. ID. No. 10)
      5'TCGTCGCTTATGCGGTACAGAGCG3'.
```

Total genomic DNA of E. coli O55:H7 was then digested with SacII (enzyme purchased from Promega, Madison, Wis. and used according to the manufacturer's instructions). The resulting DNA fragments were then circularized by adding DNA ligase and ligase buffer (purchased from New England Biolabs, and used according to the manufacturer's instructions). Primer pairs (6)—5'CGGGGTACCCCGTAAGG-GACCAGTTTCTTACCTGGG3' (SEQ. ID. No. 5) and 5'GCCCTATCTAGATAAAGG3' (SEQ. ID. No. 6), and (7)—5'GTTAAAGCCTTCCGCGG3' (SEQ. ID. No. 7) and 5'TGCCCGCTACATCTCCTC3' (SEQ. ID. No. 8) were then used to amplify DNA beyond the 5' and 3' termini of the E. coli O55:H7 gnd, respectively. The resulting sequence data then prompted the design and use of the primer pair (8)—5'CCATCAGTAATAATGAAAAGGAATT3' (SEQ. ID. No. 11) and 5'TCATTAGCTCCTCTTAAGATCGC3' (SEQ. ID. No. 12) to amplify the E. coli O55 gnd allele. Primer pairs (9)—5'TCGTCGCTTATGCGGTACAGAGCG3') (SEQ. ID. No. 10) or 5'GCGTTCTTAAAGAGTCCTGC3' (SEQ. ID. No. 13) and 5'TGCCCGCTACATCTCCTC3' (SEQ. ID. No. 8) amplified DNA spanning the 3' ends of gnd of E. coli O157:H7, and E. coli O55:H7 and E. coli O55:H6 strains (DEC lineages 1 and 2).

PCR was performed using either the Expand™ Long Template PCR System (Boehringer Mannheim, Indianapolis, Ind.) ("Expand System") or Taq DNA polymerase (Promega, Madison, Wis.). For initial pan-gnd amplifications, Taq DNA polymerase (Promega) was used. For amplifications using the Expand system, reactions were performed in 50 µl containing BMB buffer 1 supplied by the manufacturer. DNA polymerases used were either Taq DNA polymerase supplied by Promega, catalog number M1865 (5 U/µl) (A) or Taq and Pwo DNA polymerases supplied by Boehringer-Mannheim (3.5 U/µl) (B). Buffers used were: Promega Taq DNA polymerase 10× reaction buffer, without MgCl$_2$ (supplied with polymerase by manufacturer) (10× buffer is 500 mM KCl, 100 mM Tris-HCl (pH 9.0 at 25° C.), 1.0% Triton® X-100); Promega Taq DNA polymerase 10× reaction buffer, with MgCl$_2$ (supplied by manufacturer) (10× buffer is 500 mM KCl, 15 mM MgCl$_2$, 100 mM Tris-HCl (pH 9.0 at 25° C.), 1.0% Triton® X-100); or Boehringer-Mannheim Expand 10× Buffer 1 (supplied by manufacturer). Thermocycling conditions included: 35 cycles at 94° C. (1 min), 37° C. (1 min), and 72° C. (1 min), followed by a 7 minute incubation at 72° C.); 30 cycles at 94° C. (1 min), 37° C. (1 min), and 72° C. (1 min), followed by a 7 minute incubation at 72° C.; an initial cycle at 95° C. (3 min), 55° C. (1 min), and 74° C. (1 min), followed by 35 cycles of 95° C. (1 min), 55° C. (1 min), and 74° C. (1 min), and a final incubation at 72° C. (5 min); or an initial incubation at 92° C. (2 min), followed by 10 cycles at 92° C. (10 sec), 52° C. (30 sec), and 68° C. (1 min), and 10 more cycles at 92° C. (10 sec), 52° C. (30 sec), and 68° C. (1 min plus successive 10 second increments during each cycle). All PCR reactions were performed in a PTC™-100 programmable thermal cycler (MJ Research, Inc., Watertown, Mass.). The resulting amplicons were visualized in ethidium bromide stained agarose gels.

Initially, Taq-generated amplicons of the E. coli O157 gnd alleles were cloned into pSK+ (Stratagene), after digestion with BamHI and EcoRI, and an amplicon of the internal portion of the E. coli O55:H7 gnd allele was cloned into the EcoRI site of pSK+. Subsequently, the pGEM T Easy Vector (Promega, Madison, Wis.) was used for cloning and sequencing of PCR products. White colonies, which suggest that the DNA was inserted into the cloning vector, were grown in LB broth with ampicillin (200 mg/mL), and resulting plasmids were obtained and prepared using the Qiaprep Spin Miniprep Kit (Qiagen Inc., Valencia, Calif.) according to the manufacturer's instructions. Confirmation of an insert was obtained by digestion with EcoRI and agarose gel electrophoresis. Cloned inserts were sequenced using vector specific (SP6 and T7) and appropriate intervening primers, and the Perkins Elmer Applied Biosystems Dye Terminator Cycle Sequencing Ready reaction Kit (Part no 402079, Perkins Elmer, Foster City, Calif.) or the Perkins Elmer Applied Systems BigDye™ Terminator Cycle Sequencing Ready Reaction Kit (Part number 43031521, Perkins Elmer, Foster City, Calif.). Sequencing was performed at the Fred Hutchinson Cancer Research Center using a ABI 373 sequencer (Applied Biosystems) or at the University of Washington Department of Biochemistry using an ABI 377 automated sequencer (Applied Biosystems).

For sequences of cloned amplicons that were derived from amplification of gnd using Taq polymerase without a proof-reading system, unambiguous bidirectional sequence was obtained. For each of these strains, a subsequent amplicon was prepared and cloned using the Expand System, and at least one additional confirmation of each nucleotide was obtained by sequence analysis. For amplicons obtained only by use of the Expand System, unambiguous bidirectional double stranded sequences were obtained. Sequences were aligned with the GCG program (University of Wisconsin). BLAST searches were performed using the NCBI Blast server. (Gish and States, Nat. Genet., 3:266-272 (1993)).

The sequence of the gnds and corresponding proteins of several toxigenic O157 E. coli strains are provided below (gnd SEQ. ID. No./6-PGD SEQ. ID. No):

(1) 157:H7, strain 86-24 (SEQ ID. Nos. 22 and 23);

(2) 157:H7, strain 2433 (from Colombia also called H8) (SEQ ID. Nos. 16 and 17);

(3) 157:H7, strain ADLL 1541 (a strain from Australia) (SEQ ID. Nos. 18 and 19);

(4) 157:H7, strain 85-07 (SEQ ID. Nos. 24 and 25);

(5) 157:H7, strain 87-16 (SEQ ID. Nos. 26 and 27); and (6) 157:NM, strain 2755 (a non-motile, sorbitol fermentor from Germany) (SEQ ID. Nos. 20 and 21).

When the gnd sequences of these strains were compared, only 2 and 3 nucleotides in strains 85-07 and 87-16, respectively, differed from the sequence derived for E. coli O157: H7, strain 86-24. Further, the non-motile O157 pathogen also possessed a gnd that was almost identical to the gnd of E. coli O157:H7, its slightly greater evolutionary distance from E. coli O157:H7 notwithstanding. These findings established that the exceedingly toxic E. coli O157:H7 possess a gnd that has undergone only minor genetic drift and provided evidence that stable sequences associated with pathogenicity could be determined.

The sequence of the gnds and corresponding proteins of several non Shiga-toxigenic, nonpathogenic *E. coli* strains are provided below (gnd SEQ. ID. No./6-PGD SEQ. ID. No):
  (1) 55:H7, strain TB182A (SEQ. ID. Nos. 42 and 43);
  (2) 157:H3, strain 3004-89 (SEQ. ID. Nos. 28 and 29);
  (3) 157:H12, strain 5933 (SEQ. ID. Nos. 30 and 31);
  (4) 157:H16, strain 13A80 (SEQ. ID. Nos. 40 and 41);
  (5) 157:H16, strain 13A81 (SEQ. ID. Nos. 32 and 33);
  (6) 157:H38, strain 3005-89 (SEQ. ID. Nos. 36 and 37);
  (7) 157:H43, strain 7E (SEQ. ID. Nos. 38 and 39); and
  (8) 157:H45, strain 13A83 (SEQ. ID. Nos. 34 and 35).

Upon comparison of the sequences of the highly toxigenic strains with the less toxigenic strains, the inventor discovered that several polymorphisms could be used to identify the highly toxigenic *E. coli* O157 strains. Table 1 lists many of the polymorphisms found, that is, the positions at which the gnds of *E. coli* O157:H7 strain 86-24 (the reference strain) differ from the other gnd genes that were sequenced. These polymorphisms are also depicted graphically in FIG. 1. Notably, the sites at which the gnds of the non-pathogenic strains differ from the gnds of pathogenic *E. coli* O157:H7 occur in a subset of positions such that distinct patterns are discernible. For example, single nucleotide polymorphisms were found in strains 13A81 and 13A83 (*E. coli* O157 isolates expressing H antigens 16 and 45, respectively); strains 13A80, 7E, 3005-89, 3004-89, and G5933 (*E. coli* O157 expressing H antigens 16, 43, 38, 3, and 12, respectively); and each of the non-H7 *E. coli* O157 strains. As one of skill will readily appreciate, the amino acid sequences that correspond to the polymorphisms described in Table 1 (i.e., the polymorphisms expressed in terms of the amino acid) can be rapidly determined by matching the position of the nucleotide polymorphism to the protein sequences found in the sequence listing.

Surprisingly, one specific polymorphism, the T218I, was discovered in pathogenic O157:H7 strains and the O55:H7 strain TB182A but not any of non-pathogenic O157:H7 strains. The sequence data revealed that the non-pathogenic strains, except O55:H7, have a cytosine and guanine residue at nucleotide positions 653 and 654, respectively; whereas, the pathogenic strains have a thymine and cytosine at positions 653 and 654, respectively. Thus, a convenient way to distinguish pathogenic O157:H7 strains from non-pathogenic O157:H7 strains involves the identification of a "C→T" mutation at nucleotide position 653 of gnd and/or a "G→C" mutation at nucleotide position 654 or the presence of an isoleucine amino acid residue at amino acid position 218. Because the gnd of *E. coli* O55:H7 is only about 82% homologous to the gnd of *E. coli* O157:H7 (e.g., strain 86-24), these strains can be easily distinguished at several different loci, as will be described in greater detail below.

TABLE 1

| Pos. | 86-24 | 13A81 | 13A83 | 13A80 | 7E | 3005 | 3004 | 5933 |
|---|---|---|---|---|---|---|---|---|
| 24 | A | C | C | | | | | |
| 36 | A | T | T | | | | | |
| 45 | G | A | A | | | | | |
| 51 | C | T | T | | | | | |
| 54 | T | | | A | A | A | A | A |
| 102 | T | | | C | C | C | C | C |
| 103 | T | | | | | | C | |
| 111 | A | | | G | G | G | G | G |
| 114 | G | A | A | | | | | |
| 177 | A | G | G | G | G | G | G | G |
| 204 | T | | | | | | C | C |
| 211 | T | C | C | C | C | C | C | C |
| 261 | T | C | C | C | C | C | C | C |
| 263 | A | | | | | | | G |

TABLE 1-continued

| Pos. | 86-24 | 13A81 | 13A83 | 13A80 | 7E | 3005 | 3004 | 5933 |
|---|---|---|---|---|---|---|---|---|
| 267 | A | T | T | G | G | G | G | G |
| 291 | C | | | | | | | T |
| 306 | T | C | C | C | C | C | C | C |
| 317 | A | T | T | | | | | |
| 351 | A | | | C | C | C | C | C |
| 369 | C | T | T | | | | | |
| 387 | T | C | C | C | C | C | C | C |
| 390 | T | | | A | A | A | A | A |
| 393 | G | A | A | A | A | A | A | A |
| 395 | A | G | | | | | | |
| 396 | G | | | A | A | A | A | A |
| 399 | C | G | G | | | | | |
| 402 | A | G | G | G | G | G | G | G |
| 405 | A | G | G | G | G | G | G | G |
| 411 | T | G | G | | | | | |
| 420 | T | C | C | | | | | |
| 453 | A | G | G | G | G | G | G | G |
| 459 | G | T | T | | | | | |
| 466 | C | T | T | | | | | |
| 483 | A | C | C | | | | | |
| 486 | G | T | T | | | | | |
| 498 | T | C | C | | | | | |
| 501 | G | A | A | | | | | |
| 504 | A | G | G | | | | | |
| 507 | C | T | T | | | | | |
| 534 | A | G | G | | | | | |
| 547 | A | G | | | | | | |
| 561 | C | T | T | | | | | |
| 576 | C | T | T | A | A | A | A | A |
| 585 | G | A | A | A | A | A | A | A |
| 618 | T | C | C | | | | | |
| 621 | T | C | C | C | C | C | C | C |
| 627 | C | T | T | | | | | |
| 631 | A | T | T | | | | | |
| 633 | C | T | T | | | | | |
| 648 | G | A | A | | | | | |
| 653 | T | C | C | C | C | C | C | C |
| 654 | C | | | G | G | G | G | G |
| 702 | T | C | C | C | C | C | C | C |
| 711 | C | T | T | T | T | T | T | T |
| 720 | T | C | C | C | C | C | C | C |
| 759 | C | T | T | | | | | |
| 768 | A | | G | | | | | |
| 780 | A | G | G | | | | | |
| 786 | G | C | C | C | C | C | C | C |
| 789 | C | T | T | T | T | T | T | T |
| 810 | A | G | G | | | | | |
| 834 | G | A | A | | | | | |
| 861 | A | T | T | T | T | T | T | T |
| 864 | C | T | T | T | T | T | T | T |
| 888 | C | | | T | T | T | T | T |
| 894 | T | C | C | C | C | C | C | C |
| 897 | G | | | A | A | A | A | A |
| 910 | T | A | A | | | | | |
| 918 | A | G | G | G | G | G | G | G |
| 919 | C | A | A | | | | | |
| 924 | G | | | A | A | A | A | A |
| 933 | T | A | A | A | A | A | A | A |
| 939 | C | T | T | | | | | |
| 951 | C | T | T | | | | | |
| 957 | A | G | G | | | | | |
| 966 | C | T | T | | | | | |
| 972 | A | G | G | G | G | G | G | G |
| 1002 | T | | | C | C | C | C | C |
| 1008 | G | C | C | C | C | C | C | C |
| 1017 | A | G | G | G | G | G | G | G |
| 1026 | G | | | T | T | T | T | T |
| 1040 | A | | | | | | T | |
| 1098 | C | | | T | T | T | T | T |
| 1122 | C | | | T | T | T | T | T |
| 1131 | T | A | A | | | | | |
| 1173 | T | G | G | G | G | G | G | G |

TABLE 1-continued

| Pos. | 86-24 | 13A81 | 13A83 | 13A80 | 7E | 3005 | 3004 | 5933 |
|---|---|---|---|---|---|---|---|---|
| 1197 | C | | | T | T | T | T | T |
| 1215 | C | T | T | T | T | T | T | T |
| 1224 | C | T | T | T | T | T | T | T |
| 1233 | G | A | A | | | | | |
| 1266 | C | G | G | | | | | |
| 1284 | T | | | C | C | C | C | C |
| 1287 | C | | | T | T | T | T | T |
| 1296 | C | | | T | T | T | T | T |
| 1302 | T | A | A | | | | | |
| 1314 | G | A | A | | | | | |
| 1350 | G | | | A | A | A | A | A |
| 1392 | C | T | T | T | T | T | T | T |

The discovered sequences were aligned with the GCG program (University of Wisconsin) and several Blast searches were performed on the NCBI Blast server using the nucleotide sequence of *E. coli* O157:H7, strain 86-24 as the query sequence. (Gish and States, *Nat. Genet.*, 3:266-272 (1993)). The high scoring pairs from the *E. coli* strains that were used are provided in Table 2.

TABLE 2

| High-scoring Segment Pairs: | | Score | P(N) | N |
|---|---|---|---|---|
| gb\|U14423\|ECU14423 | *Escherichia coli* A8190 6-phosphogl... | 6675 | 0.0 | 1 |
| gb\|M63829\|ECOR56 | *Escherichia coli* 6-phosphogluconat... | 6585 | 0.0 | 1 |
| gb\|M63827\|ECOR25 | *Escherichia coli* 6-phosphogluconat... | 6549 | 0.0 | 1 |
| gb\|M64331\|ECONDGN | *E. coli* (strain ECOR65) 6-phosphogl... | 6540 | 0.0 | 1 |
| gb\|M63823\|ECOR18 | *Escherichia coli* 6-phosphogluconat... | 6513 | 0.0 | 1 |
| gb\|M64328\|ECONDGK | *E. coli* (strain ECOR69) 6-phosphogl... | 6495 | 0.0 | 1 |
| gb\|M64329\|ECONDGL | *E. coli* (strain ECOR70) 6-phosphogl... | 6468 | 0.0 | 1 |
| gb\|M64330\|ECONDGM | *E. coli* (strain ECOR68) 6-phosphogl... | 6441 | 0.0 | 1 |
| gb\|M63825\|ECOR21 | *Escherichia coli* 6-phosphogluconat... | 6432 | 0.0 | 1 |
| gb\|M63824\|ECOR20 | *Escherichia coli* 6-phosphogluconat... | 6423 | 0.0 | 1 |
| gb\|AE000294\|ECAE000294 | *Escherichia coli* K-12 MG1655 secti... | 6414 | 0.0 | 1 |
| dbj\|D90841\|D90841 | *E. coli* genomic DNA, Kohara clone #... | 6414 | 0.0 | 1 |
| gb\|M63821\|ECOR10 | *Escherichia coli* 6-phosphogluconat... | 6405 | 0.0 | 1 |
| gb\|K02072\|ECOGND | *E. coli* gnd gene coding for 6-phosp... | 6405 | 0.0 | 1 |
| gb\|M63826\|ECOR23 | *Escherichia coli* 6-phosphogluconat... | 6369 | 0.0 | 1 |
| gb\|M63822\|ECOR11 | *Escherichia coli* 6-phosphogluconat... | 6315 | 0.0 | 1 |
| gb\|U14469\|SBU14469 | *Shigella boydii* ATCC 8700 6-phosph... | 6306 | 0.0 | 1 |
| gb\|M63828\|ECOR47 | *Escherichia coli* 6-phosphogluconat... | 6297 | 0.0 | 1 |
| gb\|U14456\|ECU14456 | *Escherichia coli* EC63 6-phosphoglu... | 6288 | 0.0 | 1 |
| emb\|X71970\|SFRFBAJ | *S. flexneri* bB, galF, rfbA-J, rfbX,... | 6270 | 0.0 | 1 |
| gb\|U14442\|ECU14442 | *Escherichia coli* EC40 6-phosphoglu... | 6270 | 0.0 | 1 |
| gb\|U14436\|ECU14436 | *Escherichia coli* EC15 6-phosphoglu... | 6261 | 0.0 | 1 |
| gb\|U14467\|SDU14467 | *Shigella dysenteriae* ATCC 13313 6-... | 6252 | 0.0 | 1 |
| gb\|U14445\|ECU14445 | *Escherichia coli* EC43 6-phosphoglu... | 6234 | 0.0 | 1 |
| gb\|U14433\|ECU14433 | *Escherichia coli* E851819 6-phospho... | 6225 | 0.0 | 1 |
| gb\|U14448\|ECU14448 | *Escherichia coli* EC46 6-phosphoglu... | 6216 | 0.0 | 1 |
| gb\|U14438\|ECU14438 | *Escherichia coli* EC25 6-phosphoglu... | 6216 | 0.0 | 1 |
| gb\|U14441\|ECU14441 | *Escherichia coli* EC35 6-phosphoglu... | 6189 | 0.0 | 1 |
| gb\|U14455\|ECU14455 | *Escherichia coli* EC6 6-phosphogluc... | 6180 | 0.0 | 1 |
| gb\|U14435\|ECU14435 | *Escherichia coli* EC14 6-phosphoglu... | 6180 | 0.0 | 1 |
| gb\|U14460\|ECU14460 | *Escherichia coli* EC69 6-phosphoglu... | 6153 | 0.0 | 1 |
| gb\|U14462\|EFU14462 | *Escherichia fergusonii* ATCC 35469... | 6148 | 0.0 | 1 |
| gb\|U14459\|ECU14459 | *Escherichia coli* EC70 6-phosphoglu... | 6144 | 0.0 | 1 |
| gb\|U14450\|ECU14450 | *Escherichia coli* EC5 6-phosphogluc... | 6135 | 0.0 | 1 |
| gb\|U14439\|ECU14439 | *Escherichia coli* EC52 6-phosphoglu... | 6126 | 0.0 | 1 |
| gb\|U14431\|ECU14431 | *Escherichia coli* E2666-74 6-phosph... | 6126 | 0.0 | 1 |
| gb\|U14458\|ECU14458 | *Escherichia coli* EC68 6-phosphoglu... | 6117 | 0.0 | 1 |
| gb\|U14440\|ECU14440 | *Escherichia coli* EC32 6-phosphoglu... | 6081 | 0.0 | 1 |
| gb\|U14434\|ECU14434 | *Escherichia coli* EC10 6-phosphoglu... | 6081 | 0.0 | 1 |
| gb\|U14470\|SSU14470 | *Shigella sonnei* ATCC 29930 6-phosp... | 6027 | 0.0 | 1 |
| gb\|U14457\|ECU14457 | *Escherichia coli* EC64 6-phosphoglu... | 6000 | 0.0 | 1 |
| gb\|U14446\|ECU14446 | *Escherichia coli* EC44 6-phosphoglu... | 6000 | 0.0 | 1 |
| gb\|U14468\|SFU14468 | *Shigella flexneri* ATCC 29903 6-pho... | 5919 | 0.0 | 1 |
| gb\|U14451\|ECU14451 | *Escherichia coli* EC50 6-phosphoglu... | 5622 | 0.0 | 1 |
| gb\|U14449\|ECU14449 | *Escherichia coli* EC49 6-phosphoglu... | 5613 | 0.0 | 1 |
| gb\|M64324\|ECOGNDG | *E. coli* (strain ECOR4) 6-phosphoglu... | 5199 | 0.0 | 1 |
| emb\|X15651\|SEGNDB | *S. enterica* gnd gene for 6-phospho... | 5082 | 0.0 | 1 |
| gb\|M64332\|STYGNDA | *S. typhimurium* (strain LT2) 6-phosp... | 5082 | 0.0 | 1 |
| dbj\|D21242\|KPNCPS | *Klebsiella pneumoniae* cps gene clu... | 5001 | 0.0 | 1 |
| gb\|M64325\|ECONDGH | *E. coli* (strain ECOR16) 6-phosphogl... | 5001 | 0.0 | 1 |
| dbj\|AB010150\|AB010150 | *Escherichia coli* O8 wb gene cluste... | 4965 | 0.0 | 1 |
| gb\|U14424\|CDU14424 | *Citrobacter diversus* CT19 6-phosph... | 4938 | 0.0 | 1 |
| gb\|U14427\|CDU14427 | *Citrobacter diversus* CT4 6-phospho... | 4929 | 0.0 | 1 |
| gb\|U14425\|CDU14425 | *Citrobacter diversus* CT27 6-phosph... | 4929 | 0.0 | 1 |
| gb\|U14428\|CDU14428 | *Citrobacter diversus* CT42 6-phosph... | 4920 | 0.0 | 1 |
| gb\|U14429\|CDU14429 | *Citrobacter diversus* CT45 6-phosph... | 4911 | 0.0 | 1 |
| gb\|U14432\|CDU14432 | *Citrobacter diversus* CT9 6-phospho... | 4893 | 0.0 | 1 |
| gb\|L27646\|ECOGNDH | *E. coli* phosphogluconate dehydroge... | 4884 | 0.0 | 1 |
| gb\|U14353\|SEU14353 | *Salmonella enterica* V serovar Broo... | 4858 | 0.0 | 1 |
| gb\|U14495\|SEU14495 | *Salmonella enterica* IIIa isolate S... | 4848 | 0.0 | 1 |

TABLE 2-continued

| High-scoring Segment Pairs: Score P(N) | | | N | |
|---|---|---|---|---|
| gb\|U14481\|SEU14481 | *Salmonella enterica* V 6-phosphoglu . . . | 4839 | 0.0 | 1 |
| gb\|U14508\|SEU14508 | *Salmonella enterica* V isolate S304 . . . | 4830 | 0.0 | 1 |
| gb\|U14466\|CFU14466 | *Citrobacter freundii* ATCC 8090 6-p . . . | 4829 | 0.0 | 1 |
| gb\|U14509\|SEU14509 | *Salmonella enterica* V isolate S304 . . . | 4821 | 0.0 | 1 |
| gb\|U14360\|SEU14360 | *Salmonella enterica* I serovar Glos . . . | 4804 | 0.0 | 1 |
| gb\|U14500\|SEU14500 | *Salmonella enterica* II isolate S30 . . . | 4803 | 0.0 | 1 |
| gb\|U14496\|SEU14496 | *Salmonella enterica* IIIa isolate S . . . | 4803 | 0.0 | 1 |
| gb\|U14485\|SEU14485 | *Salmonella enterica* I ParatyphiB 6 . . . | 4794 | 0.0 | 1 |
| gb\|U14476\|SEU14476 | *Salmonella enterica* I Saintpaul 6- . . . | 4794 | 0.0 | 1 |
| gb\|U14368\|SEU14368 | *Salmonella enterica* I serovar Para . . . | 4786 | 0.0 | 1 |
| gb\|U14479\|SEU14479 | *Salmonella enterica* I Typhimurium . . . | 4785 | 0.0 | 1 |
| gb\|U14346\|SEU14346 | *Salmonella enterica* IIIa serovar A . . . | 4777 | 0.0 | 1 |
| gb\|U14340\|SEU14340 | *Salmonella enterica* II serovar Spr . . . | 4777 | 0.0 | 1 |
| gb\|U14498\|SEU14498 | *Salmonella enterica* II isolate S29 . . . | 4776 | 0.0 | 1 |
| gb\|U14465\|EVU14465 | *Escherichia vulneris* ATCC 33821 6- . . . | 4776 | 0.0 | 1 |
| gb\|U14367\|SEU14367 | *Salmonella enterica* I serovar Senf . . . | 4768 | 0.0 | 1 |
| gb\|U14363\|SEU14363 | *Salmonella enterica* II serovar 1, 9 . . . | 4768 | 0.0 | 1 |
| gb\|U14361\|SEU14361 | *Salmonella enterica* II serovar Sof . . . | 4768 | 0.0 | 1 |
| gb\|U14338\|SEU14338 | *Salmonella enterica* II serovar 9, 1 . . . | 4768 | 0.0 | 1 |
| gb\|U14497\|SEU14497 | *Salmonella enterica* II isolate S29 . . . | 4767 | 0.0 | 1 |
| gb\|U14493\|SEU14493 | *Salmonella enterica* IIIb, isolate S . . . | 4767 | 0.0 | 1 |
| gb\|U14480\|SEU14480 | *Salmonella enterica* IIIb 6-phosph . . . | 4767 | 0.0 | 1 |
| gb\|U14477\|SEU14477 | *Salmonella enterica* I Javiana 6-ph . . . | 4767 | 0.0 | 1 |
| gb\|U14475\|SEU14475 | *Salmonella enterica* I Dublin 6-pho . . . | 4767 | 0.0 | 1 |
| gb\|U14474\|SEU14474 | *Salmonella enterica* I Choleraesuis . . . | 4767 | 0.0 | 1 |
| gb\|U14505\|SEU14505 | *Salmonella enterica* IV isolate S30 . . . | 4758 | 0.0 | 1 |
| gb\|U14491\|SEU14491 | *Salmonella enterica* I Enteritidis . . . | 4758 | 0.0 | 1 |
| gb\|U14357\|SEU14357 | *Salmonella enterica* I serovar Cano . . . | 4750 | 0.0 | 1 |
| gb\|U14351\|SEU14351 | *Salmonella enterica* IV serovar 43: . . . | 4750 | 0.0 | 1 |
| gb\|U14349\|SEU14349 | *Salmonella enterica* IV serovar Ar . . . | 4750 | 0.0 | 1 |
| gb\|U14503\|SEU14503 | *Salmonella enterica* VII isolate S3 . . . | 4749 | 0.0 | 1 |
| gb\|U14494\|SEU14494 | *Salmonella enterica* IIIb isolate S . . . | 4749 | 0.0 | 1 |
| gb\|U14483\|SEU14483 | *Salmonella enterica* VI isolate S30 . . . | 4749 | 0.0 | 1 |
| gb\|U14478\|SEU14478 | *Salmonella enterica* I Derby 6-phos . . . | 4749 | 0.0 | 1 |
| gb\|U14437\|ECU14437 | *Escherichia coli* EC16 6-phosphoglu . . . | 4749 | 0.0 | 1 |
| gb\|U14352\|SEU14352 | *Salmonella enterica* V serovar Balb . . . | 4741 | 0.0 | 1 |
| gb\|U14350\|SEU14350 | *Salmonella enterica* IV serovar Hou . . . | 4741 | 0.0 | 1 |
| gb\|U14490\|SEU14490 | *Salmonella enterica* I ParatyphiA 6 . . . | 4740 | 0.0 | 1 |
| gb\|U14487\|SEU14487 | *Salmonella enterica* I Typhi 6-phos . . . | 4740 | 0.0 | 1 |
| gb\|U14484\|SEU14484 | *Salmonella enterica* VI isolate S30 . . . | 4740 | 0.0 | 1 |
| gb\|U14484\|SEU14484 | *Salmonella enterica* VI isolate S30 . . . | 4740 | 0.0 | 1 |

Three distinct allele groups were found in *E. coli* O157. (See Table 3). These alleles differed from one another at about 5% of their nucleotide residues. The "gnd allele A" is comprised of gnds of toxigenic *E. coli* O157:H7 and *E. coli* O157:NM strains. The gnd sequences of strains 85-07 and 87-16 each differed from that of strain 86-24 at only two of their 1407 nucleotides; the remaining three were identical. The "gnd allele B" is found in *E. coli* O157 strains expressing flagellar antigens H3, H12, H16, and H38, and in strain DEC 7E (a nonmotile O157 with an MLEE pattern identical to that of *E. coli* O157:H43) and differs from gnd allele A at about 4% of its nucleotides. The "gnd allele C" is found in *E. coli* O157:H45 and O157:H16 strains, and differs from gnd allele A at about 6% of its 1407 nucleotides.

TABLE 3

| | Wild type *E. coli* used: | | | | | |
|---|---|---|---|---|---|---|
| Strain | Surface Antigens | | Source | gnd | Genbank number | |
| Designation | O | H | (Reference) | alleles | gnd | rfbE |
| *E. coli* O157/O55 H7 (DEC5) lineage | | | | | | |
| 86-24 | 157 | 7 | WA State patients (39) | A | AF176356 | AF163327 |
| 85-07 | 157 | 7 | WA State patients (39) | A | AF176359 | AF163328 |
| 87-16 | 157 | 7 | WA State patients (39) | A | AF176360 | AF163329 |
| H8 | 157 | 7 | Colombia (S. Mattar) | A | AF176357 | |
| ADAL233 | 157 | 7 | Australia* | A | AF176358 | |
| 2755 | 157 | NM | Germany (L. Beutin) | A | AF176361 | AF163330 |
| TB156A | 55 | 7 | WA State (40) | | | |
| TB182A | 55 | 7 | WA State (40) | | AF176369 | |
| DEC 5A-5E | 55 | 7 | Penn State (16) | | | |
| *E. coli* O157 and *E. coli* O55 in non H7 lineages | | | | | | |
| 3004-89 | 157 | 3 | CDC (N. Strockbine) | B | AF176362 | AF163326 |
| G5933 | 157 | 12 | CDC (T. Barrett) | B | AF176363 | AF163331 |

TABLE 3-continued

Wild type E. coli used:

| Strain Designation | Surface Antigens O | H | Source (Reference) | gnd alleles | Genbank number gnd | rfbE |
|---|---|---|---|---|---|---|
| 13A81 | 157 | 16 | FDA (S. Weagant) | C | AF176364 | AF163332 |
| 13A83 | 157 | 45** | CDC (N. Strockbine) | C | AF176365 | AF163333 |
| 3005-89 | 157 | 38 | CDC (N. Strockbine) | B | AF176366 | AF163334 |
| DEC7E | 157 | 43*** | Penn State (16) | B | AF176367 | AF163335 |
| 13A80 | 157 | 16 | CDC (N. Strockbine) | B | AF176368 | AF163336 |
| DEC1A | 55 | 6 | Penn State (16) | | AF176370 | |
| DEC1B | 55 | 6 | Penn State (16) | | AF176371 | |
| DEC2A | 55 | 6 | Penn State (16) | | AF176372 | |
| DEC2B | 55 | 6 | Penn State (16) | | AF176373 | |

NM = nonmotile
*Australian Government Analytical Laboratories
**Strain 3584-91is nonmotile, but has an MLEE pattern identical to that of E. coli O157:H45
***Strain DEC 7E is nonmotile, but has an MLEE pattern identical to that of E. coli O157:H43

Although E. coli O55:H7 is the closest relative to E. coli O157:H7, their gnd sequences are strikingly different. The gnd sequence of E. coli O157:H7, strain 86-24 has only about 82% homology to the gnd sequence of E. coli O55:H7, strain TB182A and there appears to be no readily apparent region of conservation between these two alleles.

By analyzing the sequence downstream of the gnd of E. coli O55:H7, the inventor also discovered the presence of one or more mobile elements within the gnd-rfb cluster. (FIG. 2). Approximately 96% of the 1934 nucleotides beyond the 3'+3915 position relative to gnd of E. coli O55:H7 (i.e., the segment that starts 3916 nucleotides beyond the 3' terminus of gnd of E. coli O55:H7, and extends towards his) were found to be identical to nucleotides between the 3'+52 and the 3'+1984 positions relative to gnd of E. coli O157:H7. The region common to E. coli O55:H7 and E. coli O157:H7 contained open reading frames (orfs) encoding UDP glucose-6-dehydrogenase and an O-antigen chain length determining protein. Sequences between positions 3'+1 and 3'+51, and 3'+1 and 3'+3915, relative to the respective E. coli O55:H7 and E. coli O157:H7 gnds, were not found to be homologous.

The DNA between positions 3"+52 and 3"+3922 relative to gnd of E. coli O55:H7 was found to have a variety of features that are pertinent to DNA mobility. Approximately, 97% of the nucleotides between positions 3'+2680 and 3'+3809 relative to the gnd allele of E. coli O55:H7 were found to be homologous to DNA encoding an E. coli Rhs-associated H-repeat (H-rpt) protein (Genbank number L02370) and eleven nucleotides (AGCTTGCCCTG) (SEQ. ID. No. 14) between positions 3'+3799 and 3'+3809, inclusive, were identical to the eleven nucleotides of an inverted repeat flanking the H-rpt unit in E. coli (Genbank number L02370). (Zhao et al., J. Bacteriol., 175:2799-2808 (1993)). A nearly identical inversion (CAGGGAAGAT) (SEQ. ID. No. 15) of this 11-mer was also identified on the opposite end of this H-rpt gene homologous segment, between positions 3'+2655 and 3'+2665.

Further, the inventor discovered an orf between positions 3'+2817 and 3'+3422 that encodes a protein of 201 amino acids, which is about 98% homologous to H-repeat protein amino acids in RhsB encoded by orf-H (Genbank number L02370). (Zhao et al., J. Bacteriol., 175:2799-2808 (1993)). Still further, the inventor found that approximately 92% of the 114 inclusive nucleotides between positions 3'+3809 and 3'+3922 relative to gnd of E. coli O55:H7, including 7 nucleotides of the sequence common to E. coli O157:H7, are identical to nucleotides adjacent to the 3' end of tnpA of Salmonella typhimurium LT2, encoding IS200 transposase A (GenBank number AF093749AF093749). DNA between nucleotides at the 3'+478 and 3'+1942 positions relative to gnd of E. coli O55:H7 were also found to be about 75% identical to E. coli O111 wbdJ and wbdK (Genbank number U13629). The two orfs corresponding to nucleotides between positions 3'+112 and 3'+1035, and 3'+1032 and 3'+2198 relative to gnd are 67% and 80% identical to WbdJ and Wbd K, respectively. (Bastin and Reeves, Gene, 164:17-23 (1995)). Three segments between nucleotides at positions 3'+2788 and 3'+3806 relative to the E. coli O55:H7 gnd allele are 83-96% homologous to non-coding regions of the E. coli O157:H7 rib cluster (Genbank numbers AF061251 and AB008676).

Next, PCR was employed using the primers: 5'GCGTTCT-TAAAGAGTCCTGC3' (SEQ. ID. No. 13) and 5'TGC-CCGCTACATCTCCTC3' (SEQ. ID. No. 8), which correspond to the 3' end of gnd and downstream regions, so as to obtain a 6.5 kb amplicon from the DNA of 11 E. coli O55 strains. This amplicon was not obtained when PCR was performed with these primers on DNA from E. coli O157:H7.

Further, the inventor has found that this amplicon can be used as a hybridization probe to efficiently detect the presence of E. coli O55 strains from diverse lineages. Genomic DNA or amplicons from E. coli HB101, E. coli O157:H7-strain 86-24, E. coli O55:H7 strains TB156A, TB182A, and 5 A-E, and E. coli O55:H6 strains 1A, 1B, 2A, and 2B were produced using the primers: 5'GCGTTCTTAAAGAGTCCTGC3' (SEQ. ID. No. 13) and 5'TGCCCGCTACATCTCCTC3' (SEQ. ID. No. 8). These DNAs were then digested with SacI, separated in 1% agarose in tris-borate-EDTA (Maniatis et al., Molecular cloning: a laboratory manual (Cold Spring Harbor Laboratory) (1982)), and were transferred to a nylon membrane (Micron Separations). The transferred DNA was then probed with a cloned amplicon generated by the primers: 5'GCGT-TCTTAAAGAGTCCTGC3' (SEQ. ID. No. 13) and 5'TGC-CCGCTACATCTCCTC3' (SEQ. ID. No. 8) using E. coli O55:H7 template DNA. The amplicon probe was labeled with the Megaprime DNA system (Amersham) and $[-\alpha^{32}P]dATP$ (New England Nuclear Research Products). This experiment showed a strong signal in the lanes loaded with DNA from an O55 strain but not from a lane loaded with DNA from an O157 strain or the HB101 control. The study above not only provides strong evidence that the region 3' to gnd in E. coli O55 strains contains a conserved element with sequences that are involved in DNA mobility but also teach a rapid method to differentiate *E. coli* O55:H7 from O157:H7.

The data above also shed light on the origins of gnd diversity in *E. coli*, and on the mobility of the rjb region. The identical structure of gnds of *E. coli* O55 in diverse lineages provides evidence that gnd and the O55 rjb cluster have transferred as an intact unit between *E. coli* strains in nature. Additionally, the nearly identical *E. coli* O55 gnds, regardless of clonal frame, supports the finding that the O55 gnd-rfb cluster has been recently disseminated in natural populations. The pan-allelic discordance between the gnds of *E. coli* expressing the O55 and O157 LPS antigens in the *E. coli* DEC5 lineage is also consistent with co-transfer of intact gnd-rjb region in this lineage of *E. coli*.

Sequence analysis verified that the recombination of the gnd-rjb region utilized transposition in *E. coli* O55 strains. A short AT-rich site of insertion into the chromosome can be identified adjacent to a 3' remnant of tnpA (of IS200), which utilizes AT-rich target integration sites. An H-repeat protein gene, however, with an intact orf, is also significant. Not wanting to limit the scope of the invention to any particular mechanism of action and offered only for the purposes of explanation, the inventor believes that the H-rpt protein gene does indeed, encode a transposase and the intactness of this gene provides evidence that the *E. coli* O55 gnd-rfb cluster has only been recently acquired by *E. coli* O55 in the three different lineages studied. Interestingly, transposition appears to be the mechanism of insertion of the *V. cholerae* O139 rjb region (Stroeher et al., *Proc. Natl. Acad. Sci. USA*, 92:10374-10378 (1995); Bik et al., *Embo J*, 14:209-216 (1995); Stroeher et al., *J. Bacteriol.*, 179:2740-2747 (1997); Comstock et al., *Mol. Microbiol.*, 19:815-826 (1996)), and H-rpt protein homologues have been proposed to play a role in rjb transfer in *Salmonella* and *Vibrio*. (Xiang et al., *J. Bacteriol.*, 176:4357-4365 (1994); Hill et al., *Mol. Microbiol.*, 12:865-871 (1994)). Moreover, two H-rpt homologues, the ISASI element of *Aeromonas salmonicida* (Gustafson et al., *J. Mol. Biol.*, 237:452-463 (1994)) and an IS1358 construct (originally found in the *V. cholerae* O139 rjb region) (Dumontier et al., *J. Bacteriol.*, 180:6101-6106 (1998)) have been demonstrated to transpose.

Additional components of the identified mobile element were also found. The *E. coli* O55 and O111 O-side chains each contain colitose (Keene et al., *Carbohydr. Res.*, 111:289-296 (1983)), an unusual residue among known bacterial LPS sugars. The rjb regions specifying these two serogroups have genes encoding WbdK and WbdJ homologues, though on different sides of gnd. WbdK is homologous to RfbH of *Yersinia pseudotuberculosis*, a CDB-4-keto-6-deoxy-D-glucose-3-dehydrase in the CDP-abequose pathway. WbdK is a putative pyridoxamine 5-phosphate-dependent dehydrase at a corresponding step in the synthesis of the O111 antigen. (Bastin and Reeves, *Gene*, 164:17-23 (1995)). WbdJ is homologous to Orf1.9 encoded by the *E. coli* capsular polysaccharide gene cluster, and is believed to perform a related function in the synthesis of the *E. coli* O111 LPS antigen.

These findings have implications for understanding the evolution of this region of the *E. coli* chromosome. First, the near uniformity of gnd structure in *E. coli* O157:H7 collected during two different decades on four continents does not agree with the current paradigm that this pathogen hypermutates and evolves rapidly. (LeClerc et al., *Science*, 274:1208-1211 (1996)). Second, rjb genes specifying the O157 antigen associate with only a limited number of distinct gnd alleles. Third, the presence of intact gnd alleles B, and C in different lineages provides evidence that non-H7 *E. coli* O157 have recently acquired a putative O157 mobile element. In the disclosure below, the inventor describes several other aspects of the invention that involve software and hardware.

Software and Hardware Embodiments

It will be appreciated by those skilled in the art that a computer readable medium having the gnd sequences and/or corresponding proteins of SEQ. ID. Nos. 16-43 are useful for the determination of homologous sequences, design of probes and primers, epitope analysis, elucidation of structural and functional domains, and the construction of protein models for rational drug design. The gnd sequences and/or corresponding proteins of SEQ. ID. Nos. 16-43 can be stored, recorded, and manipulated on any medium that can be read and accessed by a computer.

As used herein, the words "recorded" and "stored" refer to a process for storing information on computer readable medium. A skilled artisan can readily adopt any of the presently known methods for recording information on computer readable medium to generate manufactures comprising the nucleotide or polypeptide sequence information of this embodiment of the invention. A variety of data storage structures are available to a skilled artisan for creating a computer readable medium having recorded thereon a nucleotide or polypeptide sequence. The choice of the data storage structure will generally be based on the component chosen to access the stored information. Computer readable media include magnetically readable media, optically readable media, or electronically readable media. For example, the computer readable media may be a hard disc, a floppy disc, a magnetic tape, CD-ROM, RAM, or ROM as well as other types of other media known to those skilled in the art. The computer readable media on which the sequence information is stored may be in a personal computer, a network, a server or other computer systems known to those skilled in the art.

Embodiments of the invention include systems, particularly computer-based systems that contain the sequence information described herein. As used herein, "a computer-based system" refers to the hardware, software, and database used to analyze the gnd sequences and/or corresponding proteins of SEQ. ID. Nos. 16-43, or fragments thereof. The computer-based system preferably includes the storage media described above, and a processor for accessing and manipulating the sequence data. The hardware of the computer-based systems of this embodiment comprise a central processing unit (CPU) and one or more databases. A skilled artisan can readily appreciate that any one of the currently available computer-based systems are suitable.

In one particular embodiment, the computer system includes a processor connected to a bus which is connected to a main memory (preferably implemented as RAM) and a variety of secondary storage devices, such as a hard drive and removable medium storage device. The removable medium storage device may represent, for example, a floppy disk drive, a compact disk drive, a magnetic tape drive, etc. A removable storage medium, such as a floppy disk, a compact disk, a magnetic tape, etc. containing control logic and/or data recorded therein (e.g., the gnd sequences and/or corresponding proteins of SEQ. ID. Nos. 16-43) may be inserted into the removable storage device. The computer system includes appropriate software for reading the control logic and/or the data from the removable medium storage device once inserted in the removable medium storage device. The gnd sequences and/or corresponding proteins of SEQ. ID. Nos. 16-43 may be stored in a well known manner in the main memory, any of the secondary storage devices, and/or a removable storage medium. Software for accessing and processing the gnd sequences and/or corresponding proteins of SEQ. ID. Nos. 16-43 (such as search tools, compare tools, and modeling tools etc.) reside in main memory during execution.

As used herein, "a database" refers to memory that can store nucleotide or polypeptide sequence information, and protein model information. Additionally, a "database" refers to a memory access component which can access manufactures having recorded thereon nucleotide or polypeptide sequence information, and/or protein model information. In other embodiments, a database stores an "E. coli pathogen profile" that comprises nucleotide and/or polypeptide sequence information, and/or protein model information on gnd genes and 6-PGD proteins and the polymorphisms therein. Advantageously, an E. coli pathogen profile has recorded or stored in a database a plurality of polymorphisms associated with highly pathogenic and/or less pathogenic E. coli strains, which would allow investigators and clinicians to rapidly identify the presence of a particular strain of E. coli in a biological sample or food or water or other biological material. Desirably, such polymorphisms are recorded in a format that facilitates the process of determining the identity of a bacterial strain, for example, the pathogen profile can be stored such that the sequences therein that correspond to specific organisms are fully searchable by sequence, organism, and/or restriction map and homology, identity and matches to queried sequences can be determined. A preferable organization of the database is as provided by NCBI, which allows BLAST-type searching, protein model searching, key word searches, and an interface with Medline. Many other types of databases and organizations are known to those of skill in the art and several will be discussed below.

The gnd sequences and/or corresponding proteins of SEQ. ID. Nos. 16-43 may be stored and manipulated in a variety of data processor programs in a variety of formats. For example, the sequence data may be stored as text in a word processing file, such as MicrosoftWORD or WORDPERFECT or as an ASCII file in a variety of database programs familiar to those of skill in the art, such as DB2, SYBASE, or ORACLE. A "search program" refers to one or more programs that are implemented on the computer-based system to compare a nucleotide or polypeptide sequence with other nucleotide or polypeptide sequences stored within the database. A search program also refers to one or more programs that compare one or more protein models to several protein models that exist in a database. A search program is used, for example, to compare regions of the gnd sequences and/or corresponding proteins of SEQ. ID. Nos. 16-43 that match sequences in nucleic acid and/or protein data base so as to identify homologies and structural or functional motifs. Additionally, a search program is used to compare an E. coli pathogen profile to a queried sequence so as to identify the presence of one or more polymorphisms in the queried sequence and determine the strain of the bacteria from which the queried sequence was derived.

A "retrieval program" refers to one or more programs that are implemented on the computer based system to identify a homologous nucleic acid sequence, a homologous protein sequence, or a homologous protein model. Further a retrieval program can be used to identify an E. coli pathogen profile that matches a queried sequence, keyword, disease characteristic, or restriction map. Preferably, the retrieval program interfaces with a display format that presents the data from the E. coli pathogen profile in a form that can be rapidly discerned. For example, the "bar code" shown in FIG. 1 is one format that can be obtained by a retrieval program that provides information on the position of polymorphisms that can be used to identify or distinguish a particular strain of E. coli.

In several embodiments, one of the novel sequences disclosed in (SEQ. ID. Nos. 16-43) is compared to a queried sequence and the percent sequence identity is determined. Standard methods that are commonly used to compare the similarity and position of the amino acid of two polypeptides can be used to make these comparisons. Using a computer program such as BLAST or FASTA, for example, two polypeptides can be aligned for optimal matching of their respective amino acids (either along the full length of one or both sequences, or along a predetermined portion of one or both sequences). Such programs provide "default" opening penalty and a "default" gap penalty, and a scoring matrix such as PAM 250 (a standard scoring matrix; see Dayhoff et al., in: Atlas of Protein Sequence and Structure, Vol. 5, Supp. 3 (1978)) can be used in conjunction with the computer program. The percent identity can then be calculated as:

$$\frac{\text{total number of identical matches}}{[\text{length of the longer sequence within the matched span} + \text{number of gaps introduced into the longer sequence in order to align the two sequences}]} \times 100$$

Polypeptides that are at least 70% identical will typically have one or more amino acid substitutions, deletions and/or insertions. Usually, the substitutions will be conservative so as to have little or no effect on the overall net charge, polarity, or hydrophobicity of the protein but optionally may increase the activity of 6-PGD.

Several Blast searches (BlastP 2.0.10, see Altschul et al., Nucleic Acids Res. 25:3389 (1997), herein incorporated by reference) were performed on the NCBI data base (available at Internet site ncbi.nlm.nih.gov/blast) to characterize the novel 6-PGD molecules, fragments of these molecules, and regions within the gnd/rfb gene cluster, in particular the region 3' of 6-PGD. Some of the results from initial Blast searches are disclosed in Table 2. Polypeptide fragments surrounding the T218I polymorphism were searched extensively. In this particular search, the matrix was BLOSUM62, the opening gap penalty was 11, and the gap extension was 1. Additional searches included Blast 2 (BlastP 2.0.9) searches on the NCBI data base using the BLOSUM matrix with an opening penalty of 11, a gap extension of 1, and an x_dropoff of 50. These later search parameters were used to compare 6-PGD encoded by O157:H7, strains 86-24, H8, ADAL233, and 2755 to:

(1) 6-PGD encoded by O157:H7, strain 87-16;
(2) 6-PGD encoded by O55:H7, strain TB182A;
(3) 6-PGD encoded by O157:H3, strain 3004-89 (an "allele B" gene product);
(4) 6-PGD encoded by O157:H12, strain G5933 (an "allele B" gene product);
(5) 6-PGD encoded by O157:H16, strain 13A81 (an "allele C" gene product);
(6) 6-PGD encoded by O157:H45, strain 3584-91 (an "allele C" gene product);
(7) 6-PGD encoded by O157:H38, strain 3005-89 (an "allele C" gene product);
(8) 6-PGD encoded by O157:H43, strain 7E (an "allele C" gene product); and
(9) 6-PGD encoded by O157:H45, strain 3260-92 (an "allele C" gene product).
(10) 6-PGD encoded by O157:H7, strain 8507.

ORFs encoded by the gnd sequences and/or corresponding proteins of SEQ. ID. Nos. 16-43 and regions within the gnd/rjb gene cluster were also compared to known amino acid sequences found in Swissprot. Many computer programs and databases may be used with embodiments of the invention. The following list is intended not to limit the invention but to provide guidance to programs and databases that are useful with the nucleic acid and protein sequence embodiments of the invention. The programs and databases that can be used include, but are not limited to: MacPattern (EMBL), DiscoveryBase (Molecular Applications Group), GeneMine (Molecular Applications Group), Look (Molecular Applications Group), MacLook (Molecular Applications Group), BLAST and BLAST2 (NCBI), BLASTN and BLASTX (Altschul et al, *J. Mol. Biol.* 215: 403 (1990)), FASTA (Pearson and Lipman, *Proc. Natl. Acad. Sci. USA,* 85: 2444 (1988)), Catalyst (Molecular Simulations Inc.), Catalyst/SHAPE (Molecular Simulations Inc.), Cerius$^2$.DBAccess (Molecular Simulations Inc.), HypoGen (Molecular Simulations Inc.), Insight II, (Molecular Simulations Inc.), Discover (Molecular Simulations Inc.), CHARMm (Molecular Simulations Inc.), Felix (Molecular Simulations Inc.), DelPhi, (Molecular Simulations Inc.), QuanteMM, (Molecular Simulations Inc.), Homology (Molecular Simulations Inc.), Modeler (Molecular Simulations Inc.), Modeller 4 (Sali and Blundell J. Mol. Biol. 234:217-241 (1997)), ISIS (Molecular Simulations Inc.), Quanta/Protein Design (Molecular Simulations Inc.), WebLab (Molecular Simulations Inc.), WebLab Diversity Explorer (Molecular Simulations Inc.), Gene Explorer (Molecular Simulations Inc.), SeqFold (Molecular Simulations Inc.), the EMBL/Swissprotein database, the MDL Available Chemicals Directory database, the MDL Drug Data Report data base, the Comprehensive Medicinal Chemistry database, Derwents's World Drug Index database, and the BioByte-MasterFile database. Many other programs and data bases would be apparent to one of skill in the art given the present disclosure.

Additionally, aspects of the invention include recombinant vectors, probes, and primers comprising the gnd sequences and/or corresponding proteins of SEQ. ID. Nos. 16-43 and fragments thereof, in particular portions of the gnd gene or corresponding protein that contain a polymorphism described in Table 1. The discussion below describes these aspects of the invention.

Nucleic Acid Embodiments

Several embodiments of the invention include recombinant vectors, probes, and primers comprising the gnd sequences of SEQ. ID. Nos. 22, 16, 18, 24, 26, 20, 42, 28, 30, 40, 32, 36, 38, and 34 and fragments thereof. In addition to the full-length gnd genes described in SEQ. ID. Nos. 22, 16, 18, 24, 26, 20, 42, 28, 30, 40, 32, 36, 38, and 34, preferred nucleic acid embodiments include fragments of any gnd gene that have a polymorphism described in Table 1. The term "full-length" refers to either the entire sequence of genomic gnd or cDNA gnd depending on the context. Further embodiments include nucleic acids that complement the full-length gnd described in SEQ. ID. Nos. 22, 16, 18, 24, 26, 20, 42, 28, 30, 40, 32, 36, 38, and 34 and nucleic acids that complement fragments of gnd that have at least one polymorphism found in Table 1. Desired embodiments include nucleic acids having at least 9 consecutive bases of a gnd and at least one polymorphism found in Table 1 or a sequence complementary thereto. In this regard, the nucleic acid embodiments of the invention can have from 9 to approximately 1,406 consecutive nucleotides of SEQ. ID. Nos.: 22, 16, 18, 24, 26, 20, 42, 28, 30, 40, 32, 36, 38, and 34 or a complement to these sequences of virtually any length so long as the nucleic acid includes at least one polymorphism described in Table 1. One of skill in the art will readily appreciate that the gnd nucleic acids of the invention can be joined to an exogenous nucleic acid so as create a fusion product, which is within the scope of the invention, having virtually any length. Thus, a nucleic acid having a portion (i.e., about 9 to about 1,406 consecutive nucleotides) of SEQ. ID. Nos.: 22, 16, 18, 24, 26, 20, 42, 28, 30, 40, 32, 36, 38, and 34 or a complement to these sequences or a full-length gnd of the invention (either genomic or cDNA) are embodiments. That is, embodiments include a nucleic acid having at least one polymorphism described in Table 1 and less than or equal to 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, 1000, 1100, 1200, 1300, and 1406 nucleotides. Preferably, the nucleic acid embodiments, however, comprise at least 12, 13, 14, 15, 16, 17, 18, or 19 consecutive nucleotides from SEQ. ID. Nos.: 22, 16, 18, 24, 26, 20, 42, 28, 30, 40, 32, 36, 38, and 34 or a complement to these sequences, as conditions dictate, so long as the fragment has at least one polymorphism described in Table 1. More preferably, the nucleic acid embodiments comprise at least 20-30 consecutive nucleotides. These nucleic acid oligomers have biotechnological and diagnostic use, e.g., in nucleotide acid hybridization assays, Southern and Northern Blot analysis, etc. and the prognosis of *E. coli* infection. Some embodiments comprise recombinant constructs having all or part of the gnd genes disclosed in SEQ. ID. Nos. 22, 16, 18, 24, 26, 20, 42, 28, 30, 40, 32, 36, 38, and 34 or complements thereof. A recombinant construct can be capable of replicating autonomously in a host cell. Alternatively, the recombinant construct can become integrated into the chromosomal DNA of the host cell. Such a recombinant polynucleotide comprises a polynucleotide of genomic or cDNA, of semi-synthetic or synthetic origin by virtue of human manipulation. Therefore, recombinant nucleic acids comprising sequences otherwise not naturally occurring are provided by embodiments of this invention.

The nucleic acid embodiments of this invention can also be altered by mutation such as substitutions, additions, or deletions that provide for sequences encoding functionally equivalent molecules. Due to the degeneracy of nucleotide coding sequences, other DNA sequences that encode substantially the same 6-PGD amino acid sequence as depicted in SEQ. ID. Nos.: 23, 17, 19, 25, 27, 21, 43, 29, 31, 41, 33, 37, 39, and 35 can be used in some embodiments of the invention. These include, but are not limited to, nucleic acid sequences comprising all or portions of gnd depicted in SEQ. ID. Nos.: 22, 16, 18, 24, 26, 20, 42, 28, 30, 40, 32, 36, 38, and 34 or complements thereof that have been altered by the substitution of different codons that encode a functionally equivalent amino acid residue within the sequence, thus producing a silent change.

In addition, recombinant gnd-encoding nucleic acid sequences and their complementary sequences can be engineered so as to modify processing or expression. For example, and not by way of limitation, the gnd genes depicted in SEQ. ID. Nos.: 22, 16, 18, 24, 26, 20, 42, 28, 30, 40, 32, 36, 38, and 34 can be combined with a promoter sequence and/or ribosome binding site, or a signal sequence may be inserted upstream of 6-PGD-encoding sequences to permit secretion of 6-PGD and thereby facilitate harvesting or bioavailability. Additionally, a given gnd nucleic acid can be mutated in vitro or in vivo, to create and/or destroy translation, initiation, and/or termination sequences, or to create variations in coding regions and/or form new restriction sites or destroy pre-existing ones, or to facilitate further in vitro modification. Any technique for mutagenesis known in the art can be used, including but not limited to, in vitro site-directed mutagenesis. (Hutchinson et al., J. Biol. Chem. 253:6551 (1978)). Further, nucleic acids encoding other proteins or domains of other proteins can be joined to nucleic acids encoding 6-PGD so as to create a fusion protein. The resulting fusion proteins can be used as biotechnological tools to investigate the mobility of regions of the gnd/rfb cluster, for example, or to develop strain specific antibodies.

The nucleic acid embodiments can also be used as biotechnological tools for isolation procedures and diagnostic assays. By using the gnd sequences disclosed in SEQ. ID. Nos.: 22, 16, 18, 24, 26, 20, 42, 28, 30, 40, 32, 36, 38, and 34, probes that complement these sequences can be designed and manufactured by oligonucleotide synthesis. Preferred hybridization probes comprise at least one polymorphism found in Table 1. These probes can be used to screen cDNA or genomic libraries so as to isolate natural sources of the nucleic acid embodiments of the invention or can be used to identify specific strains or classes of strains of E. coli. Further, sequences from nucleic acids complementing the gnd sequences disclosed in SEQ. ID. Nos.: 22, 16, 18, 24, 26, 20, 42, 28, 30, 40, 32, 36, 38, and 34, can be used to make oligonucleotide primers by conventional oligonucleotide synthesis for use in amplification strategies, such as PCR. These oligonucleotide primers can be used, for example, to isolate the nucleic acid embodiments of this invention by amplifying the sequences resident in genomic DNA or biological samples by using PCR or other enzyme-mediated nucleic acid amplification techniques. Such diagnostic and food or water screening techniques are discussed in greater detail below.

Alternatively, the nucleic acids encoding the gnd sequences disclosed in SEQ. ID. Nos.: 22, 16, 18, 24, 26, 20, 42, 28, 30, 40, 32, 36, 38, and 34, or fragments thereof are manipulated using conventional techniques in molecular biology to create recombinant constructs that express 6-PGD or fragments of 6-PGD. The discussion that follows describes some of these expression constructs and protein embodiments.

Protein Embodiments

The 6-PGD polypeptide embodiments or derivatives thereof, include but are not limited to, those molecules having as a primary amino acid sequence all of the amino acid sequence substantially as depicted in SEQ. ID. Nos.: 23, 17, 19, 25, 27, 21, 43, 29, 31, 41, 33, 37, 39, and 35 and fragments of these sequences at least three amino acids in length including altered sequences in which functionally equivalent amino acid residues are substituted for residues within the sequence resulting in a silent change. Preferred fragments include at least one of the polymorphisms that can be deduced from Table 1, as described previously. It is to be understood that in the following discussion in this section, references made to 6-PGD in a general sense are intended to encompass the proteins and fragments thereof found in SEQ. ID. Nos. 23, 17, 19, 25, 27, 21, 43, 29, 31, 41, 33, 37, 39, and 35.

Accordingly, one or more amino acid residues within the 6-PGD polypeptide of SEQ. ID. Nos.: 23, 17, 19, 25, 27, 21, 43, 29, 31, 41, 33, 37, 39, and 35 or fragments thereof can be substituted by another amino acid of a similar polarity that acts as a functional equivalent, resulting in a silent alteration. Substitutes for an amino acid within the sequence can be selected from other members of the class to which the amino acid belongs. For example, the non-polar (hydrophobic) amino acids include alanine, leucine, isoleucine, valine, proline, phenylalanine, tryptophan, and methionine. The polar neutral amino acids include glycine, serine, threonine, cysteine, tyrosine, asparagine and glutamine. The positively charged (basic) amino acids include arginine, lysine, and histidine. The negatively charged (acidic) amino acids include aspartic acid and glutamic acid. The aromatic amino acids include phenylalanine, tryptophan, and tyrosine.

The 6-PGD fragments of the invention can be less than or equal to 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 225, 250, 275, 300, 325, 350, 375, 400, 425, 450, and 468 amino acids in length. In other aspects of the invention, the 6-PGD polypeptide of SEQ. ID. Nos.: 23, 17, 19, 25, 27, 21, 43, 29, 31, 41, 33, 37, 39, and 35 or fragments thereof or derivatives thereof are differentially modified during or after translation, e.g., by phosphorylation, glycosylation, cross-linking, acylation, proteolytic cleavage, linkage to an antibody molecule, membrane molecule, or other ligand. (Ferguson et al., Ann. Rev. Biochem. 57:285-320 (1988)).

In several embodiments, the 6-PGD polypeptide of SEQ. ID. Nos.: 23, 17, 19, 25, 27, 21, 43, 29, 31, 41, 33, 37, 39, and 35 or fragments thereof are expressed in a cell line. The sequences, constructs, vectors, clones, and other materials comprising the present invention can advantageously be in enriched or isolated form. As used herein, "enriched" means that the concentration of the material is at least about 2, 5, 10, 100, or 1000 times its natural concentration (for example), advantageously 0.01%, by weight, preferably at least about 0.1% by weight. Enriched preparations from about 0.5%, 1%, 5%, 10%, and 20% by weight are also contemplated. The term "isolated" requires that the material be removed from its original environment (e.g., the natural environment if it is naturally occurring). For example, a naturally occurring polynucleotide or polypeptide present in a living animal is not isolated, but the same polynucleotide or polypeptide, separated from some or all of the coexisting materials in the natural system, is isolated. It is also advantageous that the sequences be in purified form. The term "purified" does not require absolute purity; rather, it is intended as a relative definition. Purification of starting material or natural material to at least one order of magnitude, preferably two or three orders, and more preferably four or five orders of magnitude is expressly contemplated.

To express the proteins encoded by gnd or portions thereof, nucleic acids containing the coding sequence for 6-PGD or fragments of 6-PGD are obtained and cloned into a suitable expression vector such that the coding region is operably linked to a heterologous promoter. The nucleic acid encoding the protein or polypeptide to be expressed is operably linked to a promoter in an expression vector using conventional cloning technology. The expression vector can be in any of the mammalian, yeast, amphibian, insect, parasite, or bacterial expression systems known in the art. Commercially available vectors and expression systems are available from a variety of suppliers including Genetics Institute (Cambridge, Mass.), Stratagene (La Jolla, Calif.), Promega (Madison, Wis.), and Invitrogen (San Diego, Calif.). If desired, to enhance expression and facilitate proper protein folding, the codon context and codon pairing of the sequence can be optimized for the particular expression organism in which the expression vector is introduced, as explained by Hatfield, et al., U.S. Pat. No. 5,082,767, incorporated herein by this reference. Further, a secretory leader sequence can be incorporated so as to facilitate purification of the protein.

The following is provided as one exemplary method to express the proteins encoded by the nucleic acids described above. First, the methionine initiation codon for the gene and the poly A signal of the gene are identified. If the nucleic acid encoding the polypeptide to be expressed lacks a methionine to serve as the initiation site, an initiating methionine can be introduced next to the first codon of the nucleic acid using conventional techniques. Similarly, if the nucleic acid lacks a poly A signal, this sequence can be added to the construct by, for example, splicing out the Poly A signal from pSG5 (Stratagene) using BgII and SalI restriction endonuclease enzymes and incorporating it into the mammalian expression vector pXT1 (Stratagene). The vector pXT1 contains the LTRs and a portion of the gag gene from Moloney Murine Leukemia Virus. The position of the LTRs in the construct allow efficient stable transfection. The vector includes the Herpes Simplex Thymidine Kinase promoter and the selectable neomycin gene.

The nucleic acid encoding the polypeptide to be expressed can be obtained by PCR from the bacterial vector using oligonucleotide primers complementary to the nucleic acid and containing restriction endonuclease sequences for Pst I incorporated into the 5'primer and BglII at the 5' end of the corresponding cDNA 3' primer, taking care to ensure that the nucleic acid is positioned in frame with the poly A signal. The purified fragment obtained from the resulting PCR reaction is digested with PstI, blunt ended with an exonuclease, digested with Bgl II, purified and ligated to pXT1, now containing a poly A signal and digested with BglII. The ligated product is transfected into a suitable cell line, e.g., mouse NIH 3T3 cells, using Lipofectin (Life Technologies, Inc., Grand Island, N.Y.) under conditions outlined in the product specification. Positive transfectants are selected after growing the transfected cells in 600 µg/ml G418 (Sigma, St. Louis, Mo.). Preferably the expressed protein is released into the culture medium, thereby facilitating purification.

Another embodiment utilizes the "Xpress system for expression and purification" (Invitrogen, San Diego, Calif.). The Xpress system is designed for high-level production and purification of recombinant proteins from bacterial, mammalian, and insect cells. The Xpress vectors produce recombinant proteins fused to a short N-terminal leader peptide that has a high affinity for divalent cations. Using a nickel-chelating resin (Invitrogen), the recombinant protein can be purified in one step and the leader can be subsequently removed by cleavage with enterokinase.

One preferred vector for the expression of 6-PGD and fragments of 6-PGD is the pBlueBacHis2 Xpress. The pBlueBacHis2 Xpress vector is a Baculovirus expression vector containing a multiple cloning site, an ampicillin resistance gene, and a lac z gene. By one approach, the gnd nucleic acid, or portion thereof is cloned into the pBlueBacHis2 Xpress vector and SF9 cells are infected. The expression protein is then isolated or purified according to the manufacturer's instructions. Several other cultured cell lines having recombinant constructs or vectors comprising gnd or portions thereof are embodiments of the present invention and their manufacture would be routine given the present disclosure.

Proteins in the culture medium can also be separated by gel electrophoresis. The separated proteins are then detected using techniques such as Coomassie or silver staining or by using antibodies against the protein. Coomassie, silver staining, and immunolabeling of proteins are techniques familiar to those skilled in the art. If desired, the proteins can also be ammonium sulfate precipitated or separated based on size or charge prior to electrophoresis.

The protein encoded by gnd or portion thereof can also be purified using standard immunochromatography techniques. In such procedures, a solution containing the protein, such as the culture medium or a cell extract, is applied to a column having antibodies against the protein attached to the chromatography matrix. The protein is allowed to bind the immunochromatography column. Thereafter, the column is washed to remove non-specifically bound proteins. The specifically bound protein is then released from the column and recovered using standard techniques.

Further, gnd or portion thereof can be incorporated into expression vectors designed for use in purification schemes employing chimeric polypeptides. In such strategies, the coding sequence of gnd or portion thereof is inserted in frame with the gene encoding the other half of the chimera. The other half of the chimera may be β-globin or a nickel binding polypeptide encoding sequence. A chromatography matrix having antibody to β-globin or nickel attached thereto is then used to purify the chimeric protein. Protease cleavage sites can be engineered between the β-globin gene or the nickel binding polypeptide and the gnd cDNA such as enterokinase. Thus, the two polypeptides of the chimera can be separated from one another by protease digestion.

One useful expression vector for generating β-globin chimerics is pSG5 (Stratagene), which encodes rabbit β-globin. Intron II of the rabbit β-globin gene facilitates splicing of the expressed transcript, and the polyadenylation signal incorporated into the construct increases the level of expression. These techniques as described are well known to those skilled in the art of molecular biology. Standard methods are published in methods texts such as Davis et al., (*Basic Methods in Molecular Biology*, L. G. Davis, M. D. Dibner, and J. F. Battey, ed., Elsevier Press, NY, 1986) and many of the methods are available from Stratagene, Life Technologies, Inc., or Promega. Polypeptide may additionally be produced from the construct using in vitro translation systems, such as the In vitro Express™ Translation Kit (Stratagene).

In addition to isolating or purifying 6-PGD and fragments of 6-PGD by using recombinant DNA techniques, these molecules can be prepared by chemical synthesis methods (such as solid phase peptide synthesis) using methods known in the art such as those set forth by Merrifield et al., J. Am. Chem. Soc. 85:2149 (1964), Houghten et al., Proc. Natl. Acad. Sci. USA, 82:51:32 (1985), and Stewart and Young (solid phase peptide synthesis, Pierce Chem. Co., Rockford, Ill. (1984). Such polypeptides can be synthesized with or without a methionine on the amino terminus. Chemically synthesized 6-PGD and fragments of 6-PGD can be oxidized using methods set forth in these references to form disulfide bridges. 6-PGD and fragments of 6-PGD can be employed as biologically active or immunological substitutes for natural, purified 6-PGD and fragments of 6-PGD. Analogs of 6-PGD or fragments of 6-PGD include small molecules modeled on the peptides. These small molecules are also known as peptidomimetics. A peptidomimetic is a molecule that has the same effect as a peptide, usually because it has the same critical 'shape', but is not itself a peptide and hence is not broken down by proteases and is cheaper to produce. Thus, peptidomimetics that structurally and/or functionally resemble 6-PGD or fragments of 6-PGD can be made and evaluated for their ability to interact with 6-PGD in a 6-PGD characterization assay (e.g., inhibit the function of natural 6-PGD or fragment thereof) or induce an immune response in a subject. Several approaches to make peptidomimetics that resemble polypeptides are described in the art. A vast number of methods, for example, can be found in U.S. Pat. Nos. 5,288,707; 5,552,534; 5,811,515; 5,817,626; 5,817,879; 5,821,231; and 5,874,529, herein incorporated by reference in their entirety.

Following synthesis or expression and isolation or purification of the proteins encoded by gnd or a portion thereof, the isolated or purified proteins can be used to generate antibodies and tools for identifying agents that interact with 6-PGD and fragments of 6-PGD. Antibodies that recognize 6-PGD and fragments of 6-PGD have many uses including, but not limited to, biotechnological applications, therapeutic/prophylactic applications, and diagnostic applications. Such antibodies include, but are not limited to, polyclonal, monoclonal, chimeric, single chain, Fab fragments and fragments produced by a Fab expression library.

For the production of antibodies, various hosts including goats, rabbits, rats, mice, etc can be immunized by injection with 6-PGD or any portion, fragment or oligopeptide that retains immunogenic properties. Depending on the host species, various adjuvants can be used to increase immunological response. Such adjuvants include but are not limited to Freund's, mineral gels such as aluminum hydroxide, and surface active substances such as lysolecithin, pluronic polyols, polyanions, peptides, oil emulsions, keyhole limpet hemocyanin, and dinitrophenol. BCG (Bacillus Calmette-Guérin) and *Corynebacterium parvum* are potentially useful adjuvants.

Peptides used to induce specific antibodies can have an amino acid sequence consisting of at least three amino acids, preferably at least 10 or 15 amino acids that include a polymorphism as can be deduced from Table 1. Preferred antibodies, for example, include ones that specifically bind to a polypeptide having the T218I polymorphism or a nucleic acid having either the C653T or G654C but not 6-PGD or gnd that has the Thr218 or thymine or cytosine polymorphisms at nucleic acid positions 653 and 654, respectively. That is, preferred antibodies recognize an epitope that uniquely identifies the Iso218 polymorphism but not the Thr218 polymorphism or vice versa or the antibodies recognize an epitope that uniquely identifies a cytosine at nucleic acid position 653 and/or a guanine at nucleic acid position 654 or a thymine at position 653 and/or a cytosine at nucleic acid position 654. Desirably, short stretches of amino acids encoding fragments of 6-PGD are fused with those of another protein such as keyhole limpet hemocyanin and antibody is produced against the chimeric molecule. While antibodies capable of specifically recognizing 6-PGD can be generated by injecting into mice synthetic 3-mer, 10-mer, and 15-mer peptides that correspond to a protein sequence of 6-PGD, a more diverse set of antibodies can be generated by using recombinant or purified 6-PGD and fragments of 6-PGD.

To generate antibodies to 6-PGD and fragments of 6-PGD, substantially pure 6-PGD or a fragment of 6-PGD is isolated from a transfected or transformed cell. The concentration of the polypeptide in the final preparation is adjusted, for example, by concentration on an Amicon filter device, to the level of a few micrograms/ml. Monoclonal or polyclonal antibody to the polypeptide of interest can then be prepared as follows:

Monoclonal antibodies to 6-PGD or a fragment of 6-PGD can be prepared using any technique that provides for the production of antibody molecules by continuous cell lines in culture. These include but are not limited to the hybridoma technique originally described by Koehler and Milstein (Nature 256:495-497 (1975), the human B-cell hybridoma technique (Kosbor et al. Immunol Today 4:72 (1983); Cote et al Proc Natl Acad Sci 80:2026-2030 (1983), and the EBV-hybridoma technique Cole et al. Monoclonal Antibodies and Cancer Therapy, Alan R. Liss Inc, New York N.Y., pp 77-96 (1985). In addition, techniques developed for the production of "chimeric antibodies", the splicing of mouse antibody genes to human antibody genes to obtain a molecule with appropriate antigen specificity and biological activity can be used. (Morrison et al. Proc Natl Acad Sci 81:6851-6855 (1984); Neuberger et al. Nature 312:604-608 (1984); Takeda et al. Nature 314:452-454 (1985). Alternatively, techniques described for the production of single chain antibodies (U.S. Pat. No. 4,946,778) can be adapted to produce 6-PGD-specific single chain antibodies. Antibodies can also be produced by inducing in vivo production in the lymphocyte population or by screening recombinant immunoglobulin libraries or panels of highly specific binding reagents as disclosed in Orlandi et al., Proc Natl Acad Sci 86: 3833-3837 (1989), and Winter G. and Milstein C; Nature 349:293-299 (1991).

Antibody fragments that contain specific binding sites for 6-PGD can also be generated. For example, such fragments include, but are not limited to, the $F(ab')_2$ fragments that can be produced by pepsin digestion of the antibody molecule and the Fab fragments that can be generated by reducing the disulfide bridges of the $F(ab')_2$ fragments. Alternatively, Fab expression libraries can be constructed to allow rapid and easy identification of monoclonal Fab fragments with the desired specificity. (Huse W. D. et al. Science 256:1275-1281 (1989)).

By one approach, monoclonal antibodies to 6-PGD of fragments thereof are made as follows. Briefly, a mouse is repetitively inoculated with a few micrograms of the selected protein or peptides derived therefrom over a period of a few weeks. The mouse is then sacrificed, and the antibody producing cells of the spleen isolated. The spleen cells are fused in the presence of polyethylene glycol with mouse myeloma cells, and the excess unfused cells destroyed by growth of the system on selective media comprising aminopterin (HAT media). The successfully fused cells are diluted and aliquots of the dilution placed in wells of a microtiter plate where growth of the culture is continued. Antibody-producing clones are identified by detection of antibody in the supernatant fluid of the wells by immunoassay procedures, such as ELISA, as originally described by Engvall, E., Meth. Enzymol. 70:419 (1980), and derivative methods thereof. Selected positive clones can be expanded and their monoclonal antibody product harvested for use. Detailed procedures for monoclonal antibody production are described in Davis, L. et al. *Basic Methods in Molecular Biology* Elsevier, New York. Section 21-2.

Polyclonal antiserum containing antibodies to heterogenous epitopes of a single protein can be prepared by immunizing suitable animals with the expressed protein or peptides derived therefrom described above, which can be unmodified or modified to enhance immunogenicity. Effective polyclonal antibody production is affected by many factors related both to the antigen and the host species. For example, small molecules tend to be less immunogenic than others and may require the use of carriers and adjuvant. Also, host animals vary in response to site of inoculations and dose, with both inadequate or excessive doses of antigen resulting in low titer antisera. Small doses (ng level) of antigen administered at multiple intradermal sites appears to be most reliable. An effective immunization protocol for rabbits can be found in Vaitukaitis, J. et al. *J. Clin. Endocrinol. Metab.* 33:988-991 (1971).

Booster injections can be given at regular intervals, and antiserum harvested when antibody titer thereof, as determined semi-quantitatively, for example, by double immunodiffusion in agar against known concentrations of the antigen, begins to fall. See, for example, Ouchterlony, O. et al., Chap. 19 in: *Handbook of Experimental Immunology* D. Wier (ed) Blackwell (1973). Plateau concentration of antibody is usually in the range of 0.1 to 0.2 mg/ml of serum (about 12 µM). Affinity of the antisera for the antigen is determined by preparing competitive binding curves, as described, for example, by Fisher, D., Chap. 42 in: *Manual of Clinical Immunology*, 2d Ed. (Rose and Friedman, Eds.) Amer. Soc. For Microbiol., Washington, D.C. (1980). Antibody preparations prepared according to either protocol are useful in quantitative immunoassays that determine concentrations of antigen-bearing substances in biological samples; they are also used semi-quantitatively or qualitatively (e.g., in diagnostic embodiments that identify the presence of 6-PGD in biological samples).

Diagnostic and Screening Embodiments

Generally, the diagnostics and screening methods of the invention can be classified according to whether the embodiment is a nucleic acid or protein based assay. These assays preferably identify and distinguish the strain and extent of pathogenicity of an *E. coli* present in a biological sample (e.g., a sample from a patient, food source, or liquid source) by detecting the presence of one or more polymorphisms at the gnd locus. That is, several of the diagnostic and screening embodiments focus on the detection of one or more polymorphisms provided in Table 1 or that can be deduced from Table 1 in a nucleic acid or protein sample. Additionally, the manufacture of kits that incorporate the reagents and methods described in the following embodiments so as to allow for the rapid detection and identification of highly pathogenic O157:H7 *E. coli* are contemplated. The diagnostic kits can include a nucleic acid probe or an antibody or combinations thereof, which specifically detect the one or more polymorphisms described in Table 1 or that can be deduced from Table 1. The detection component of these kits will typically be supplied in combination with one or more of the following reagents. A support capable of absorbing or otherwise binding DNA, RNA, or protein will often be supplied. Available supports include membranes of nitrocellulose, nylon or derivatized nylon that can be characterized by bearing an array of positively charged substituents. One or more restriction enzymes, control reagents, buffers, amplification enzymes, and non-human polynucleotides like calf-thymus or salmon-sperm DNA can be supplied in these kits.

Useful nucleic acid-based diagnostic techniques include, but are not limited to, direct DNA sequencing, Southern Blot analysis, single-stranded confirmation analysis (SSCA), RNase protection assay, dot blot analysis, nucleic acid amplification, and combinations of these approaches. The starting point for these analysis is isolated or purified DNA from a biological sample. Most simply, fecal material is obtained from a subject to be tested or a food or water sample is provided. While the bacterial can be cultures to obtain a sufficient amount of DNA to test, in some embodiments, the bactrerial DNA is extracted from the sample and amplified by a DNA amplification technique such as PCR using primers that correspond to regions of the gnd locus and/or the gnd/rjb cluster, preferably regions having a polymorphism listed in Table 1.

Several methods can be used to detect a polymorphism in a biological sample. Direct DNA sequencing, either manual sequencing or automated fluorescent sequencing can detect such sequence variations. Another approach is the single-stranded confirmation polymorphism assay (SSCA) (Orita et al., *Proc. Natl. Acad. Sci. USA* 86:2776-2770 (1989), herein incorporated by reference). This method, however, does not detect all sequence changes, especially if the DNA fragment size is greater than 200 base pairs, but can be optimized to detect most DNA sequence variation. The reduced detection sensitivity is a disadvantage, but the increased throughput possible with SSCA makes it an attractive, viable alternative to direct sequencing for mutation detection. The fragments which have shifted mobility on SSCA gels are then sequenced to determine the exact nature of the DNA sequence variation. Other approaches based on the detection of mismatches between the two complimentary DNA strands include clamped denaturing gel electrophoresis (CDGE) (Sheffield et al., *Am. J. Hum. Genet.* 49:699-706 (1991)), heteroduplex analysis (HA) (White et al., *Genomics* 12:301-306 (1992)), and chemical mismatch cleavage (CMC) (Grompe et al., *Proc. Natl. Acad. Sci. USA* 86:5855-5892 (1989)). A review of currently available methods of detecting DNA sequence variation can be found in Grompe, *Nature Genetics* 5:111-117 (1993).

A rapid preliminary analysis to detect polymorphisms and DNA sequences can be performed by looking at a series of Southern Blots of DNA cut with one or more restriction enzymes preferably with a large number of restriction enzymes. Each block contains lanes of DNA from uninfected individuals and the DNA to be tested. Southern Blots displaying hybridizing fragments when probed with sequences corresponding to one or more polymorphisms described in Table 1 indicate the presence of the specific *E. coli* strain. The detection of point mutations can also be accomplished by amplifying the DNA directly from the sample using primers corresponding to the regions flanking one or more polymorphisms described in Table 1 by standard PCR techniques and sequencing the amplicons, as will be discussed in greater detail below.

Seven well-known nucleic acid-based methods for confirming the presence of one or more polymorphisms described in Table 1 are provided below. Provided for exemplary purposes only and not intended to limit any aspect of the invention, these methods include:

(1) single-stranded confirmation analysis (SSCA) (Orita et al.);

(2) denaturing gradient gel electrophoresis (DGGE) (Wartell et al., *Nucl. Acids Res.* 18:2699-2705 (1990) and Sheffield et al., *Proc. Natl. Acad. Sci. USA* 86:232-236 (1989)), both references herein incorporated by reference;

(3) RNase protection assays (Finkelstein et al., *Genomics* 7:167-172 (1990) and Kinszler et al., *Science* 251:1366-1370 (1991)) both references herein incorporated by reference;

(4) the use of proteins which recognize nucleotide mismatches, such as the *E. Coli* mutS protein (Modrich, Ann. Rev. Genet. 25:229-253 (1991), herein incorporated by reference;

(5) allele-specific PCR (Rano and Kidd, Nucl. Acids Res. 17:8392 (1989), herein incorporated by reference), which involves the use of primers that hybridize at their 3' ends to a polymorphism and, if the polymorphism is not present, an amplification product is not observed; and (6) Amplification Refractory Mutation System (ARMS), as disclosed in European Patent Application Publication No. 0332435 and in Newton et al., *Nucl. Acids Res.* 17:2503-2516 (1989), both references herein incorporated by reference; and (7) temporal temperature gradient gel electrophoresis (TTGE), as described by Bio-Rad in U.S./E.G. Bulletin 2103, herein incorporated by reference.

In SSCA, DGGE, TTGE, and RNase protection assay, a new electrophoretic band appears when the polymorphism is present. SSCA and TTGE detect a band that migrates differentially because the sequence change causes a difference in single-strand, intramolecular base pairing, which is detectable electrophoretically. RNase protection involves cleavage of the mutant polynucleotide into two or more smaller fragments. DGGE detects differences in migration rates of sequences compared to less pathogenic strain gnd sequences, using a denaturing gradient gel. In an allele-specific oligonucleotide assay (ASOs) (Conner et al., *Proc. Natl. Acad. Sci. USA* 80:278-282 (1983)), an oligonucleotide is designed that detects a specific sequence, and an assay is performed by detecting the presence or absence of a hybridization signal. In the mutS assay, the protein binds only to sequences that contain a nucleotide mismatch in a heteroduplex between polymorphic and non-polymorphic sequences. Mismatches, in this sense of the word refers to hybridized nucleic acid duplexes in which the two strands are not 100% complementary. The lack of total homology results from the presence of one or more polymorphisms in an amplicon obtained from a biological sample, for example, that has been hybridized to a non-polymorphic strand. Mismatched detection can be used to detect point mutations in the gnd gene or in its mRNA product. While these techniques are less sensitive than sequencing, they are easily performed on a large number of biological samples and are amenable to array technology.

In preferred embodiments, the nucleic acid embodiments of the present invention are attached to a support in an ordered array wherein a plurality of nucleic acid probes are attached to distinct regions of the support that do not overlap with each other. Preferably, such an ordered array is designed to be "addressable" where the distinct locations of the probe are recorded and can be accessed as part of an assay procedure. In some embodiments, addressable nucleic acid arrays comprise a plurality of nucleic acid probes that complement a plurality of polymorphisms listed in Table 1. These probes are joined to a support in different known locations. The knowledge of the precise location of each nucleic acid probe makes these "addressable" arrays particularly useful in binding assays. The nucleic acids from a preparation of several biological samples are then labeled by conventional approaches (e.g., radioactivity or fluorescence) and the labeled samples are applied to the array under conditions that permit hybridization. If a nucleic acid in the samples hybridizes to a probe on the array, then a signal will be detected at a position on the support that corresponds to the location of the hybrid. Since the identity of each labeled sample is known and the region of the support on which the labeled sample was applied is known, an identification of the presence and polymorphic variant (i.e., the strain of *E. coli*) can be rapidly determined. Conventional methods in DNA amplification, as will be discussed below, can also be incorporated so as to detect the presence of less than 10 bacterial cells. These approaches are easily automated using technology known to those of skill in the art of high throughput diagnostic or detection analysis.

Additionally, an opposite approach to that presented above can be employed. Nucleic acids present in biological samples can be disposed on a support so as to create an addressable array. Preferably, the samples are disposed on the support at known positions that do not overlap. The presence of nucleic acids having a desired polymorphism in each sample is determined by applying labeled nucleic acid probes that complement nucleic acids that encode the polymorphism and detecting the presence of a signal at locations on the array that correspond to the positions at which the biological samples were disposed. Because the identity of the biological sample and its position on the array is known, the identification of the polymorphic variant can be rapidly determined. As above, conventional methods in DNA amplification can be incorporated so as to detect the presence of very few bacterial cells. These approaches are also easily automated using technology known to those of skill in the art of high throughput diagnostic analysis.

Any addressable array technology known in the art can be employed with this aspect of the invention. One particular embodiment of polynucleotide arrays is known as Genechips™, and has been generally described in U.S. Pat. No. 5,143,854; PCT publications WO 90/15070 and 92/10092. These arrays are generally produced using mechanical synthesis methods or light directed synthesis methods, which incorporate a combination of photolithographic methods and solid phase oligonucleotide synthesis. (Fodor et al., *Science,* 251:767-777, (1991)). The immobilization of arrays of oligonucleotides on solid supports has been rendered possible by the development of a technology generally identified as "Very Large Scale Immobilized Polymer Synthesis" (VL-SIPS™) in which, typically, probes are immobilized in a high density array on a solid surface of a chip. Examples of VLSIPS™ technologies are provided in U.S. Pat. Nos. 5,143, 854 and 5,412,087 and in PCT Publications WO 90/15070, WO 92/10092 and WO 95/11995, which describe methods for forming oligonucleotide arrays through techniques such as light-directed synthesis techniques. In designing strategies aimed at providing arrays of nucleotides immobilized on solid supports, further presentation strategies were developed to order and display the oligonucleotide arrays on the chips in an attempt to maximize hybridization patterns and diagnostic information. Examples of such presentation strategies are disclosed in PCT Publications WO 94/12305, WO 94/11530, WO 97/29212, and WO 97/31256.

A wide variety of labels and conjugation techniques are known by those skilled in the art and can be used in various nucleic acid assays. There are several ways to produce labeled nucleic acids for hybridization or PCR including, but not limited to, oligolabeling, nick translation, end-labeling, or PCR amplification using a labeled nucleotide. Alternatively, a nucleic acid encoding 6-PGD, or any portion of it, can be cloned into a vector for the production of an mRNA probe. Such vectors are known in the art, are commercially available, and can be used to synthesize RNA probes in vitro by addition of an appropriate RNA polymerase such as T7, T3 or SP6 and labeled nucleotides. A number of companies such as Pharmacia Biotech (Piscataway N.J.), Promega (Madison Wis.), and U.S. Biochemical Corp (Cleveland Ohio) supply commercial kits and protocols for these procedures. Suitable reporter molecules or labels include those radionuclides, enzymes, fluorescent, chemiluminescent, or chromogenic agents, as well as, substrates, cofactors, inhibitors, magnetic particles and the like.

An example of a mismatch cleavage technique that is amenable to array technology is the RNase protection method. In practice, the method involves the use of a labeled riboprobe which is complementary to a gnd sequence having a polymorphism (e.g., the C653T and G654C polymorphism that distinguishes highly pathogenic O157:H7 and O55:H7 from less pathogenic *E. coli* strains). The riboprobe and either mRNA or DNA isolated and amplified from a biological sample are annealed (hybridized) and subsequently digested with the enzyme RNase A, which is able to detect mismatches in a duplex RNase structure. If a mismatch is detected by RNase A, the polymorphic variant is not present in the sample and the enzyme cleaves at the site of the mismatch and destroys the riboprobe. Thus, when the annealed RNA is separated on a electrophoretic gel matrix, if a mismatch has been detected and cleaved by RNase A, an RNA product will be seen which is much smaller than the full length duplex RNA for the riboprobe and the mRNA or DNA. Alternatively, complements to the riboprobe can be dispersed on an array and stringently probed with the products from the Rnase A digestion after denaturing any remaining hybrids. In this case, if a mismatch is detected and probe destroyed by Rnase A, the complements on the array will not anneal with the degraded RNA under stringent conditions. A plurality of riboprobes can be employed to screen for multiple polymorphisms in this manner so long as care is taken that the probes and complements do not cross hybridize. Panels having such arrays that screen several loci are particularly useful for the development of *E. coli* pathogen profiles, as described above. In a similar fashion, DNA probes can be used to detect mismatches, through enzymatic or chemical cleavage. See, e.g., Cotton, et al., *Proc. Natl. Acad. Sci. USA* 85:4397 (1988); Shenk et al., *Proc. Natl. Acad. Sci. USA* 72:989 (1975); and Novack et al., *Proc. Natl. Acad. Sci. USA* 83:586 (1986).

Alternatively, mismatches can be detected by shifts in the electrophoretic ability of mismatched duplexes relative to matched duplexes. (See, e.g., Cariello, Human *Genetics* 42:726 (1988), herein incorporated by reference). With either riboprobes or DNA probes, the cellular mRNA or DNA that corresponds to regions of gnd containing polymorphisms can be amplified by PCR before hybridization. DNA sequences isolated from biological samples which have been amplified by use of PCR can then be screened using allele-specific probes. These probes are nucleic acid oligomers, each of which contains a region including one or more polymorphisms present in Table 1. For example, one oligomer may be about 30 nucleotides in length and corresponds to the C653T and G654C polymorphism. By use of a battery of such allele-specific probes, PCR amplification products can be screened to identify the presence of specific polymorphisms. Of course, the most definitive test for the presence of a highly pathogenic *E. coli* in a sample is to directly compare nucleotide or protein sequences isolated from a biological sample with one or more of the polymorphisms present in Table 1.

A variety of PCR techniques are familiar to those skilled in the art. For a review of PCR technology, see Molecular Cloning to Genetic Engineering White, B. A. Ed. in *Methods in Molecular Biology* 67: Humana Press, Totowa (1997), the disclosure of which is incorporated herein by reference in its entirety and the publication entitled "PCR Methods and Applications" (1991, Cold Spring Harbor Laboratory Press), the disclosure of which is incorporated herein by reference in its entirety. For amplification of mRNAs, it is within the scope of the present invention to reverse transcribe mRNA into cDNA followed by PCR (RT-PCR); or, to use a single enzyme for both steps as described in U.S. Pat. No. 5,322,770, the disclosure of which is incorporated herein by reference in its entirety, or, to use Reverse Transcriptase Asymmetric Gap Ligase Chain Reaction (RT-AGLCR), as described by Marshall R. L. et al. (*PCR Methods and Applications* 4:80-84, 1994), the disclosure of which is incorporated herein by reference in its entirety.

In each of these amplification procedures, primers on either side of the sequence to be amplified are added to a suitably prepared nucleic acid sample along with dNTPs and a thermostable polymerase such as Taq polymerase, Pfu polymerase, or Vent polymerase. The nucleic acid in the sample is denatured and the primers are specifically hybridized to complementary nucleic acid sequences in the sample. The hybridized primers are extended. Thereafter, another cycle of denaturation, hybridization, and extension is initiated. The cycles are repeated multiple times to produce an amplified fragment containing the nucleic acid sequence between the primer sites. PCR has further been described in several patents including U.S. Pat. Nos. 4,683,195, 4,683,202 and 4,965,188, the disclosure of which is incorporated herein by reference in its entirety.

The primers are selected to be substantially complementary to a portion of the sequence of gnd DNA or mRNA and a portion of the sequence that complements the sequence of gnd DNA or mRNA, thereby allowing the sequences between the primers to be amplified. The length of the primers for use with this aspect of the invention is identical to most of the lengths of the nucleic acid embodiments provided previously. That is, primer length can be less than or equal to 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, 1000, 1100, 1200, 1300, and 1406 nucleotides. Preferably, however primers are 16, 17, 18, 19, 20, 21, 22, 23, 24, 25, 26, 27, 28, 29 and 30 nucleotides in length. Shorter primers tend to lack specificity for a target nucleic acid sequence and generally require cooler temperatures to form sufficiently stable hybrid complexes with the template. Longer primers are expensive to produce and can sometimes self-hybridize to form hairpin structures. The formation of stable hybrids depends on the melting temperature (Tm) of the DNA. The Tm depends on the length of the primer, the ionic strength of the solution and the G+C content. The higher the G+C content of the primer, the higher is the melting temperature because G:C pairs are held by three H bonds whereas A:T pairs have only two. The G+C content of the amplification primers of the present invention preferably ranges between 10 and 75%, more preferably between 35 and 60%, and most preferably between 40 and 55%. The appropriate length for primers under a particular set of assay conditions may be empirically determined by one of skill in the art.

The spacing of the primers determines the length of the segment to be amplified. In the context of the present invention amplified segments carrying nucleic acid sequence encoding fragments of 6-PGD can range in size from at least about 25 bp to 35 kb. Amplification fragments from 25-1407 bp are typical, fragments from 50-1000 bp are preferred and fragments from 100-600 bp are highly preferred. It will be appreciated that amplification primers for the gnd genes of the invention can be of any sequence that allows for specific amplification of a region of the gnd genes disclosed in SEQ. ID. Nos. 22, 16, 18, 24, 26, 20, 42, 28, 30, 40, 32, 36, 38, and 34 and can, for example, include modifications such as restriction sites to facilitate cloning.

In a preferred embodiment, highly pathogenic O157:H7 *E. coli* are identified and differentiated from less pathogenic *E. coli* by employing PCR amplification with two sets of primers. A first set of primers is designed to produce an amplicon containing at least the C653T and G654C polymorphisms, which distinguish the highly pathogenic O157:H7 and O55:H7 *E. coli* from less pathogenic strains. A second set of primers is designed to produce an amplicon that is unique to the O55:H7 parasite, e.g., the primer pair: 5'GCGTTCT-TAAAGAGTCCTGC3' (SEQ. ID. No. 13) and 5'TGC-CCGCTACATCTCCTC3' (SEQ. ID. No. 8), which correspond to the 3' end of gnd and downstream regions yield a 6.5 kb amplicon from the DNA of 11 *E. coli* O55 strains but not *E. coli* O157:H7. By using SSCP or TTGE and simple gel electrophoresis, one of skill can rapidly identify the presence of the C653T and G654C polymorphism and determine whether or not the polymorphic variant detected is O157:H7 or O55:H7. In a similar fashion, primers and combinations of primers that uniquely identify other polymorphisms, as described in Table 1, can be employed to identify and differentiate other *E. coli* strains.

The presence of a 6-PGD protein of the invention can also be detected by using conventional assays. For example, monoclonal antibodies immunoreactive with a polymorphism found on a specific 6-PGD sequence can be used to screen biological samples for the presence of a particular strain of *E. coli* and can be used to distinguish one strain from another. Because the T218I polymorphism can distinguish highly pathogenic O157:H7 and O55:H7 from less pathogenic O157:H7, diagnostic and screening assays that comprise reagents and methods that involve the detection of the presence or absence of the T218I polymorphism are preferred embodiments. These diagnostic assays can also include a reagent that specifically differentiates the O55:H7 and O157:H7 parasites, for example, an antibody directed to an epitope found in a region of the O55:H7 6-PGD protein that is not homologous to the 6-PGD protein from an O157:H7 parasite. Such immunological assays can be done in many convenient formats.

In one embodiment, antibodies are used to immunoprecipitate the 6-PGD of the invention from solution and, in another embodiment, antibodies are used to react with 6-PGD on Western or Immuneblots of a polyacrylamide gel. Favored embodiments for detecting 6-PGD include enzyme-linked immunosorbant assays (ELISA), radioimmunoassays (RIA), immunoradiometric assays (IRMA) and immunoenzymatic assays (IEMA), including sandwich assays using monoclonal and/or polyclonal antibodies. Exemplary sandwich assays are described by David et al., in U.S. Pat. Nos. 4,376,110 and 4,486,530, hereby incorporated by reference. Other embodiments employ aspects of the immune-strip technology disclosed in U.S. Pat. Nos. 5,290,678; 5,604,105; 5,710,008; 5,744,358; and 5,747,274, herein incorporated by reference, which allow for the rapid, visual identification of the presence of multiple analytes in a sample. These teachings can be readily adapted to allow for the rapid detection of the 6-PGD polymorphisms that can be deduced from Table 1.

In preferred protein-based diagnostic and/or detection embodiments, antibodies of the present invention are attached to a support in an ordered array wherein a plurality of antibodies are attached to distinct regions of the support that do not overlap with each other. As with the nucleic acid-based arrays, the protein-based arrays are ordered arrays that are designed to be "addressable" such that the distinct locations are recorded and can be accessed as part of an assay procedure.

In some embodiments, addressable antibody arrays comprise a plurality of antibodies that recognize the 6-PGD polymorphisms that can be deduced from Table 1. These probes are joined to a support in different known locations. The knowledge of the precise location of each probe makes these "addressable" arrays particularly useful in binding assays. For example, an addressable array can comprise a support having several regions to which are joined a plurality of antibody probes that recognize the 6-PGD polymorphisms that can be deduced from Table 1. Proteins obtained from biological samples are labeled by conventional approaches (e.g., radioactivity, calorimetrically, or fluorescently) and the labeled samples are applied to the array under conditions that permit binding. If a protein in the sample binds to an antibody probe on the array, then a signal will be detected at a position on the support that corresponds to the location of the antibody-protein complex. Since the identity of each labeled sample is known and the region of the support on which the labeled sample was applied is known, an identification of the presence, concentration, and/or expression level is rapidly determined. That is, by employing labeled standards of a known concentration of 6-PGD, an investigator can accurately determine the protein concentration of 6-PGD in a sample and from this information can assess the expression level of 6-PGD. Conventional methods in densitometry can also be used to more accurately determine the concentration or expression level of 6-PGD. These approaches are easily automated using technology known to those of skill in the art of high throughput diagnostic analysis.

In another embodiment, an opposite approach to that presented above can be employed. Proteins present in biological samples can be disposed on a support so as to create an addressable array. Preferably, the protein samples are disposed on the support at known positions that do not overlap. The presence of a protein encoding a specific form of 6-PGD in each sample is then determined by applying labeled antibody probes that recognize epitopes of 6-PGD that correspond to the polymorphisms that can be deduced from Table 1 and detecting a signal at locations on the array that correspond to the positions at which the biological samples were disposed. Because the identity of the biological sample and its position on the array is known, an identification of the presence, concentration, and/or expression level of a particular 6-PGD can be rapidly determined. That is, by employing labeled standards of a known concentration of 6-PGD, an investigator can accurately determine the concentration of 6-PGD in a sample and from this information can assess the expression level of 6-PGD. Conventional methods in densitometry can also be used to more accurately determine the concentration or expression level of 6-PGD. These approaches are also easily automated using technology known to those of skill in the art of high throughput diagnostic analysis. As detailed above, any addressable array technology known in the art can be employed with this aspect of the invention and display the protein arrays on the chips in an attempt to maximize antibody binding patterns and diagnostic information.

As discussed above, the presence or detection of one or more polymorphisms in 6-PGD can provide a diagnosis of a subject's disease or indicate the contamination of a food or water supply. Additional embodiments include the preparation of diagnostic kits comprising detection components such as antibodies specific for one or more polymorphisms of 6-PGD. The detection component will typically be supplied in combination with one or more of the following reagents. A support capable of absorbing or otherwise binding RNA or protein will often be supplied. Available supports for this purpose include, but are not limited to, membranes of nitrocellulose, nylon or derivatized nylon that can be characterized by bearing an array of positively charged substituents, and Genechips™ or their equivalents. One or more enzymes, such as Reverse Transcriptase and/or Taq polymerase, can be furnished in the kit, as can dNTPs, buffers, or non-human polynucleotides like calf-thymus or salmon-sperm DNA. Results from the kit assays can be interpreted by a healthcare provider or a diagnostic laboratory. Alternatively, diagnostic kits are manufactured and sold to private individuals for self-diagnosis.

Example 1 below describes an approach that can be used to identify other regions in the rjb/gnd gene cluster that have polymorphisms useful to identify and distinguish *E. Coli* strains.

Example 1

With reference to FIG. 3, discriminating sequences flanking the gnd locus can be found by using restriction mapping and PCR cloning techniques. As shown in FIG. 3, restriction site "A" is present in fragment "B-G" (i.e., "$A_1$, $A_2$, and $A_3$"), defined below. "B" corresponds to the left-hand border of a pathogenicity or antigenicity island and "G" corresponds to the right hand border of this element. "$A_1$" is the first restriction site A site to the left of B, and "$A_2$" is the first restriction site A site to the right of G. If the sequence of fragment B-G is known e.g., gnd, the BG island flanking this sequence can be determined by using inverse PCR. Primers "C", "D", "E", and "F" are derived from the sequence of the unique pathogenicity/antigenicity island. Actual sequence is derived from the raw data, depicted in the 5' to 3' direction, as indicated under the line shown in FIG. 3. The primers are in the same (primer D, primer F) or opposite orientation (primer C and primer E).

Next, *E. coli* DNA is digested to completion with enzyme A. Ligase is then added and the resulting fragments are re-circularized. Primers are added in separate tubes with a heat stable polymerase and PCR is conducted to obtain amplicons. The amplicons are cloned and sequenced. This approach identifies sequences beyond the 5' and 3' ends of the known pathogenicity/antigenicity islands and primers derived from these sequences are used to amplify this region in a variety of pathogens and non-pathogens, as was performed for the gnd allele. The resulting amplicons are then sequenced to identify differentiating polymorphisms.

Although the invention has been described with reference to embodiments and examples, it should be understood that various modifications can be made without departing from the spirit of the invention. Accordingly, the invention is limited only by the following claims. All references cited herein are hereby expressly incorporated by reference.

What is claimed is:

1. A method for detecting the presence of *E. coli* O157:H7 and/or *E. coli* O157:NM in a sample comprising the steps of:
   (a) contacting said sample, under hybridization conditions, with a nucleic acid probe comprising at least 9 consecutive nucleotides of SEQ ID NO:20 or SEQ ID NO:22 or a sequence complementary thereto that specifically hybridizes to a target sequence comprised by a portion of the gnd gene of *E. coli* O157:H7 to form a hybridization complex, said nucleic acid probe comprising the polymorphism A393G or complement thereto; and
   (b) detecting formation of said hybridization complex as an indication of the presence of the polymorphism A393G, wherein the presence of the polymorphism A393G is indicative of *E. coli* O157:H7 and/or *E. coli* O157:NM in the sample.

2. A method of detecting *E. coli* O157:H7 and/or *E. coli* O157:NM in a sample comprising the steps of:
   (a) contacting the sample with a pair of primers capable of amplifying a target sequence within the gnd gene of *E. coli* O157:H7, and amplifying the target sequence under conditions permitting amplification of the target sequence, wherein each of said pair of primers comprises at least 9 consecutive nucleotides of SEQ ID NO:20 or SEQ ID NO:22, or a sequence complementary thereto, and wherein said target sequence comprises nucleotide position 393 of the gnd gene, and
   (b) contacting the amplified target sequence with a probe that specifically hybridizes to the polymorphism A393G or complement thereto for specifically detecting the presence of the polymorphism A393G or complement thereto in the amplified target sequence,
   wherein detection of the polymorphism A393G or complement thereto indicates the presence of *E. coli* O157:H7 and/or *E. coli* O157:NM in the sample.

3. The method of claim 1, wherein said portion further comprises polymorphism G453A.

4. The method of claim 1, wherein said portion further comprises polymorphism C653T.

5. The method of claim 1, wherein said portion further comprises polymorphism G654C.

6. The method of claim 2, wherein said target sequence further comprises polymorphism G453A.

7. The method of claim 2, wherein said target sequence further comprises polymorphism C653T.

8. The method of claim 2, wherein said target sequence further comprises polymorphism G654C.

9. A method of detecting *E. coli* O157:H7 and/or *E. coli* O157:NM in a sample comprising the steps of:
   (a) contacting the sample with a pair of primers for allele-specific amplification of a target sequence within the gnd gene of *E. coli* O157:H7, and amplifying the target sequence under conditions permitting allele-specific amplification of the target sequence, wherein each of said pair of primers comprises at least 9 consecutive nucleotides of SEQ ID NO:20 or SEQ ID NO:22, or a sequence complementary thereto, and wherein at least one of said primers comprises the polymorphism A393G or complement thereto at its 3' end, (b) detecting the amplified target sequence, wherein detection of the amplified target sequence indicates the presence of the polymorphism, thereby indicating the presence of *E. coli* O157:H7 and/or *E. coli* O157:NM in the sample.

* * * * *